US012642561B2

(12) United States Patent
Weisman et al.

(10) Patent No.:  US 12,642,561 B2
(45) Date of Patent:        Jun. 2, 2026

(54) EXTERNAL FIXATOR APPARATUS AND METHOD

(71) Applicant: Chip Shot Partner LLC, Weston, CT (US)

(72) Inventors: Tedd L. Weisman, Weston, CT (US); David Rechberger, Niwot, CO (US); Randall Allard, Golden, CO (US); Craig W. Lynn, Tucson, AZ (US); Caleb Pridey, Laramie, WY (US)

(73) Assignee: Chip Shot Partners LLC, Weston, CT (US)

( * ) Notice: Subject to any disclaimer, the term of this patent is extended or adjusted under 35 U.S.C. 154(b) by 0 days.

(21) Appl. No.: 18/771,164

(22) Filed: Jul. 12, 2024

(65) Prior Publication Data

US 2024/0366267 A1      Nov. 7, 2024

Related U.S. Application Data

(63) Continuation of application No. PCT/US2023/010859, filed on Jan. 16, 2023.

(Continued)

(51) Int. Cl.
*A61B 17/64*        (2006.01)
*A61B 17/66*        (2006.01)
*A61B 17/00*        (2006.01)

(52) U.S. Cl.
CPC ........ *A61B 17/645* (2013.01); *A61B 17/6416* (2013.01); *A61B 17/66* (2013.01); *A61B 2017/0092* (2013.01)

(58) Field of Classification Search
CPC ... A61B 17/645; A61B 17/6416; A61B 17/66; A61B 2017/0092
(Continued)

(56) References Cited

U.S. PATENT DOCUMENTS 4,628,919 A    12/1986  Clyburn
5,545,162 A     8/1996  Huebner
(Continued)

FOREIGN PATENT DOCUMENTS

CA          2121085 A1    10/1994
FR          2805147 A1 *   8/2001    ............. A61B 17/60
(Continued)

OTHER PUBLICATIONS

PE2E translation of FR-2805147-A1 (Year: 2001).*
(Continued)

*Primary Examiner* — Eduardo C Robert
*Assistant Examiner* — David C Comstock
(74) *Attorney, Agent, or Firm* — BrainSpark Associates, LLC

(57) ABSTRACT

An improved external fixator assembly for fixating fractures that includes a proximal frame assembly, a distal frame assembly and a polyaxial joint. The polyaxial joint comprises articulating components that engage to have multi-axial or polyaxial translational motion to allow for distraction/reduction and adjustment of flexion/extension, radial/ulnar deviation, pronation/supination of the wrist to an optimal wrist position. The polyaxial joint may be lockable. Fixation screws are also provided for engaging the patient's bone tissue on opposite sides of a fracture.

20 Claims, 56 Drawing Sheets

Related U.S. Application Data

(60) Provisional application No. 63/367,390, filed on Jun. 30, 2022, provisional application No. 63/299,490, filed on Jan. 14, 2022.

(58) Field of Classification Search
USPC ............................................. 606/54, 57, 59
See application file for complete search history.

(56) References Cited

U.S. PATENT DOCUMENTS

| | | | | |
|---|---|---|---|---|
| 5,620,442 | A | * | 4/1997 | Bailey ................ A61B 17/6416 |
| | | | | 606/57 |
| 5,707,370 | A | * | 1/1998 | Berki ................. A61B 17/6425 |
| | | | | 606/55 |
| 5,709,681 | A | * | 1/1998 | Pennig ................... A61B 17/60 |
| | | | | 606/57 |
| 5,951,556 | A | * | 9/1999 | Faccioli ............. A61B 17/6458 |
| | | | | 606/65 |
| 6,793,655 | B2 | | 9/2004 | Orsak |
| 6,840,939 | B2 | | 1/2005 | Venturini et al. |
| 7,147,640 | B2 | | 12/2006 | Heubner et al. |
| 8,366,710 | B2 | | 2/2013 | Hirata et al. |
| 2004/0097944 | A1 | | 5/2004 | Koman et al. |
| 2004/0133200 | A1 | | 7/2004 | Ruch et al. |
| 2013/0110110 | A1 | * | 5/2013 | Waisman ........... A61B 17/6458 |
| | | | | 606/59 |
| 2016/0038184 | A1 | * | 2/2016 | Erickson ............ A61B 17/6425 |
| | | | | 606/59 |
| 2021/0068800 | A1 | * | 3/2021 | McCormick ....... A61B 17/0206 |

FOREIGN PATENT DOCUMENTS

| | | | | |
|---|---|---|---|---|
| WO | 2004010893 | A3 | 2/2004 | |
| WO | WO-2015183226 | A2 | * 12/2015 | ............. A61B 17/66 |

OTHER PUBLICATIONS

Synthes, Distal Radius Fixator Technique Guide, Instructions for Use, 1998, pp. 1-7, Synthes, United States.

Acumed, Stableloc External Fixator System Surgical Technique, Instructions for Use, Dec. 2017, pp. 1-16, Acumed, United States.

United States International Search Authority (ISA/US), International Search Report and Written Opinion, Jul. 7, 2023, pp. 1-12, United States.

\* cited by examiner

365

95

95

95

340a    340b 355a    355b

370

375

25

25

25

380c

380b

380a

25

395a
400a
385a
387
395b
400b
385b
400c
385c
395c 390a
387
390b
390c 400a    400b 400c 385a    385b

385c

25

400b    400c

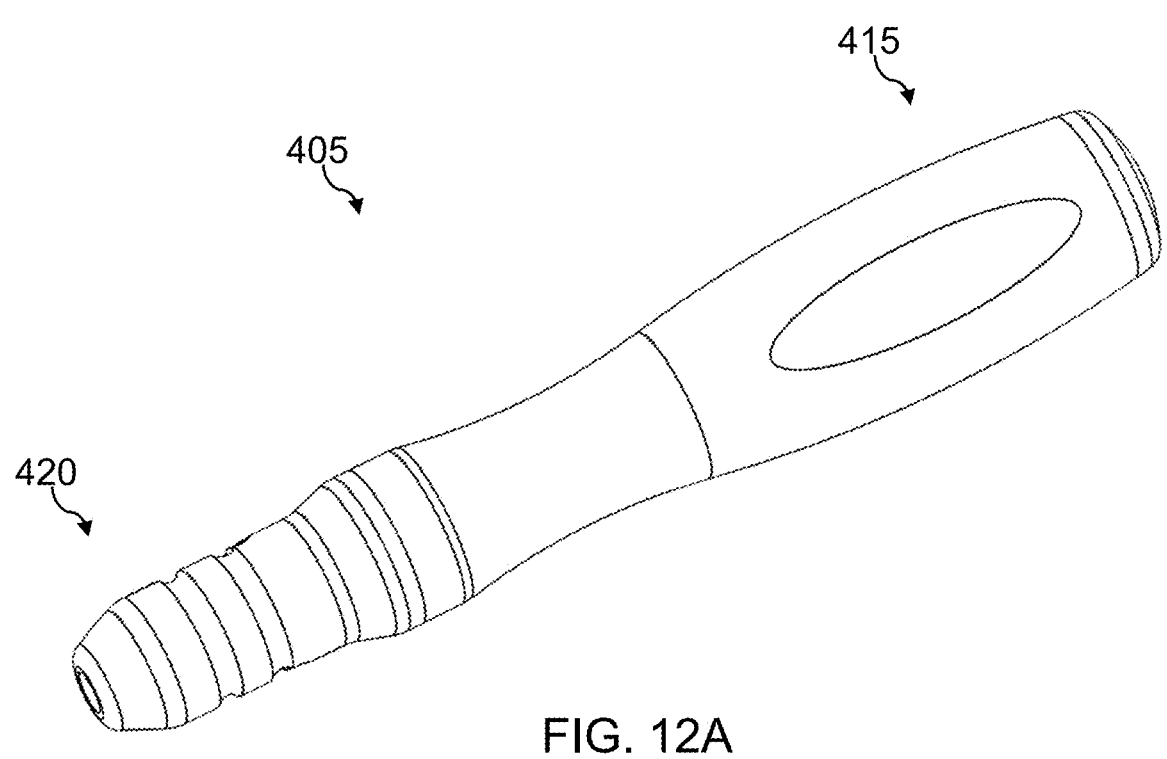
FIG. 12A
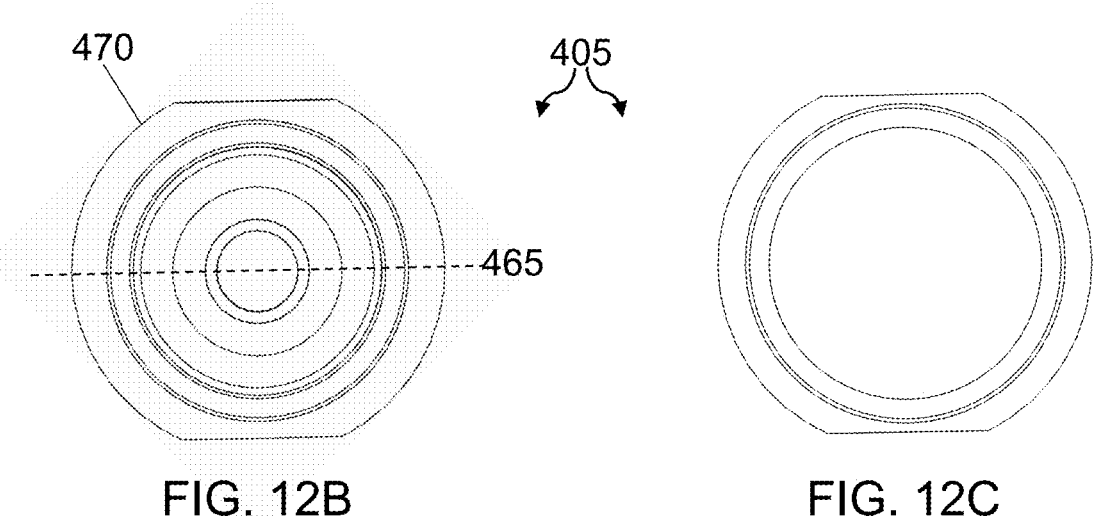
FIG. 12B                    FIG. 12C

473 ⤵

410 ⤵

475 ⤵

480 ⤵

478 ⤵

485 ⤵

410 ⤵

490

410 ⤵

485 ⤵

555
40
560
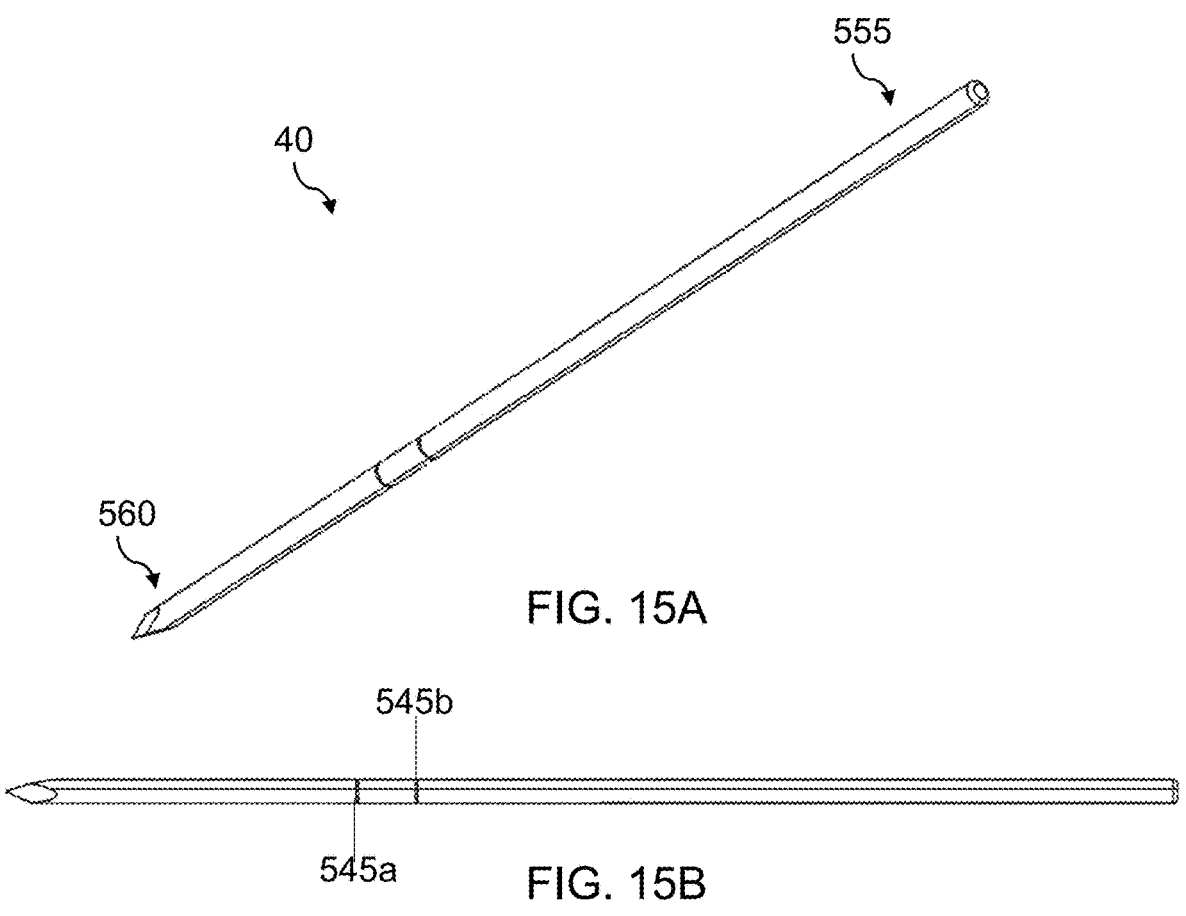
FIG. 15A
545b
545a
FIG. 15B
550
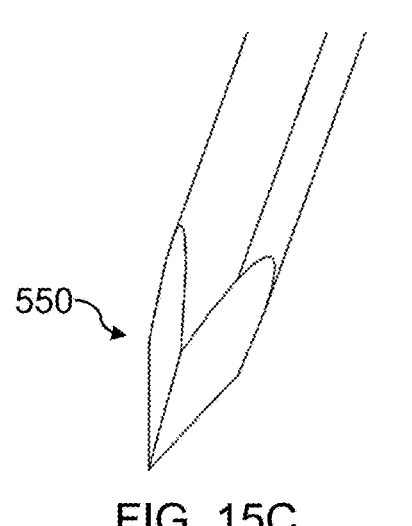
FIG. 15C
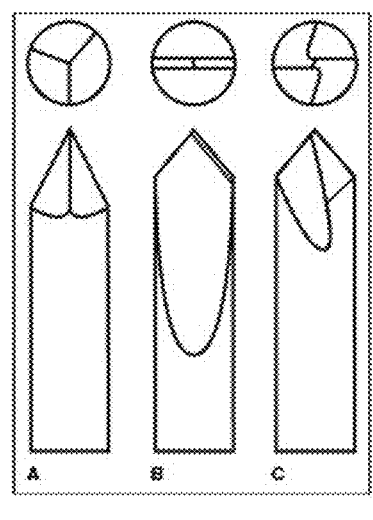
FIG. 15D

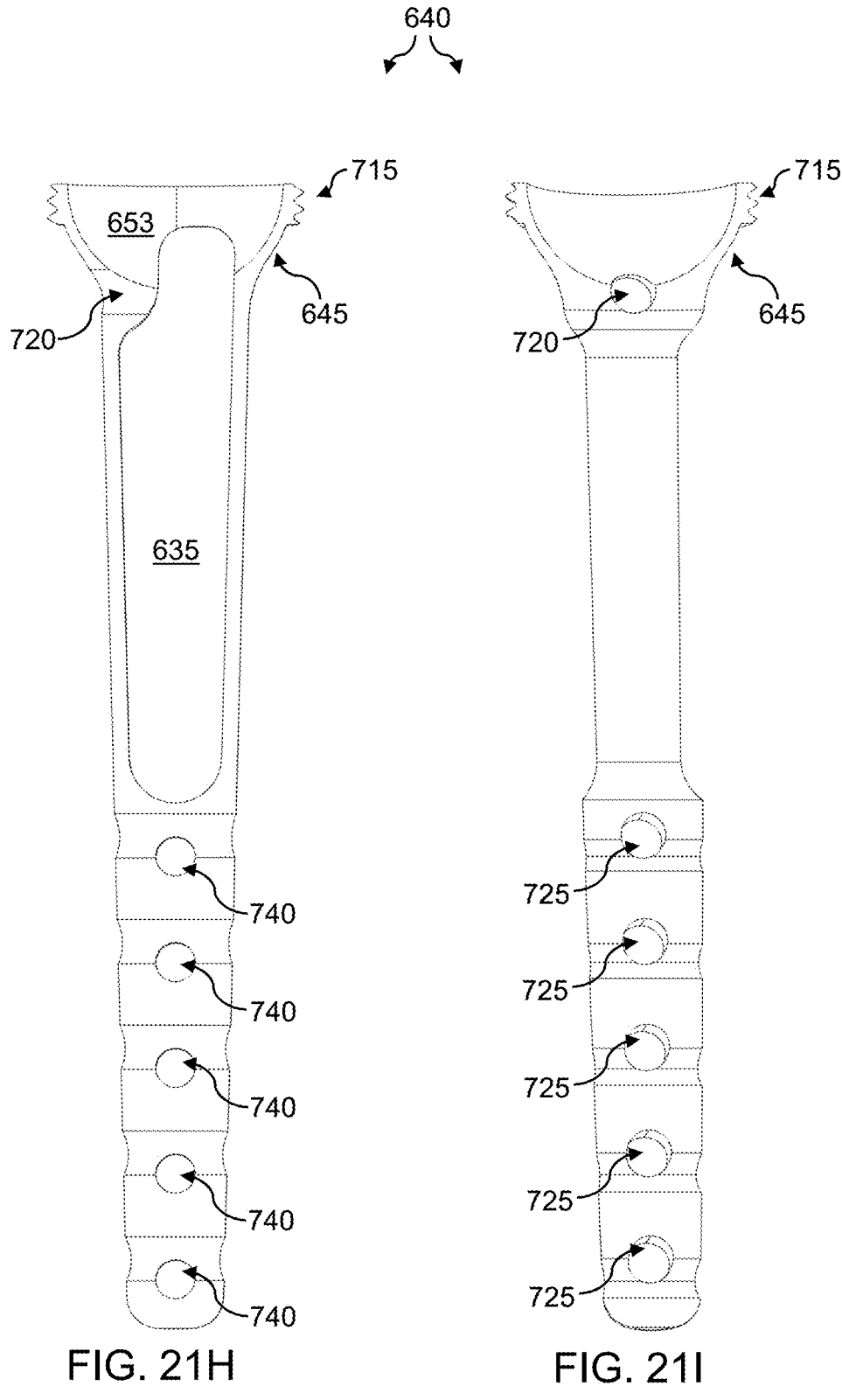
FIG. 21H                    FIG. 21I

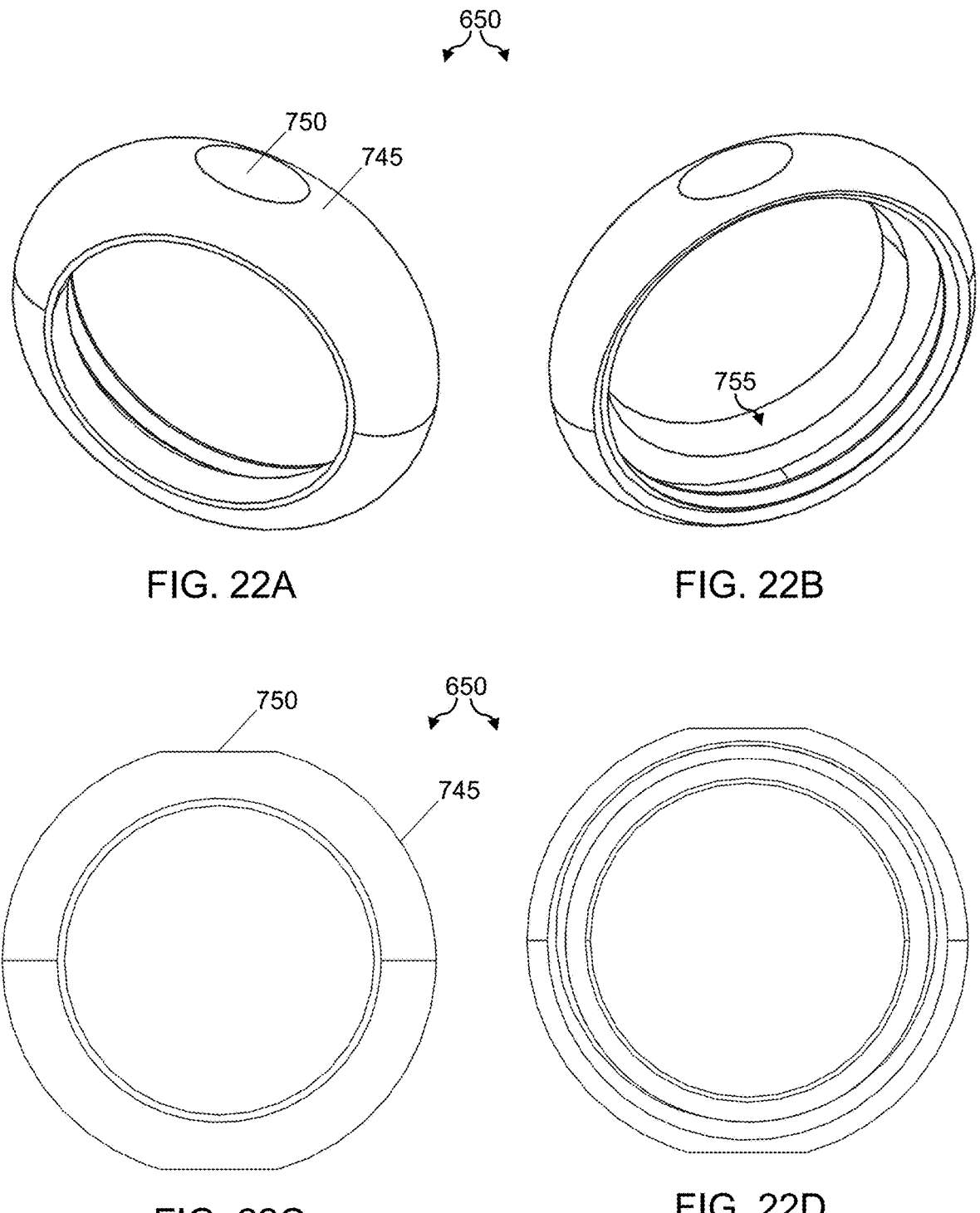
FIG. 22A                    FIG. 22B
FIG. 22C                    FIG. 22D

650

650

865

855

840a

840b

855

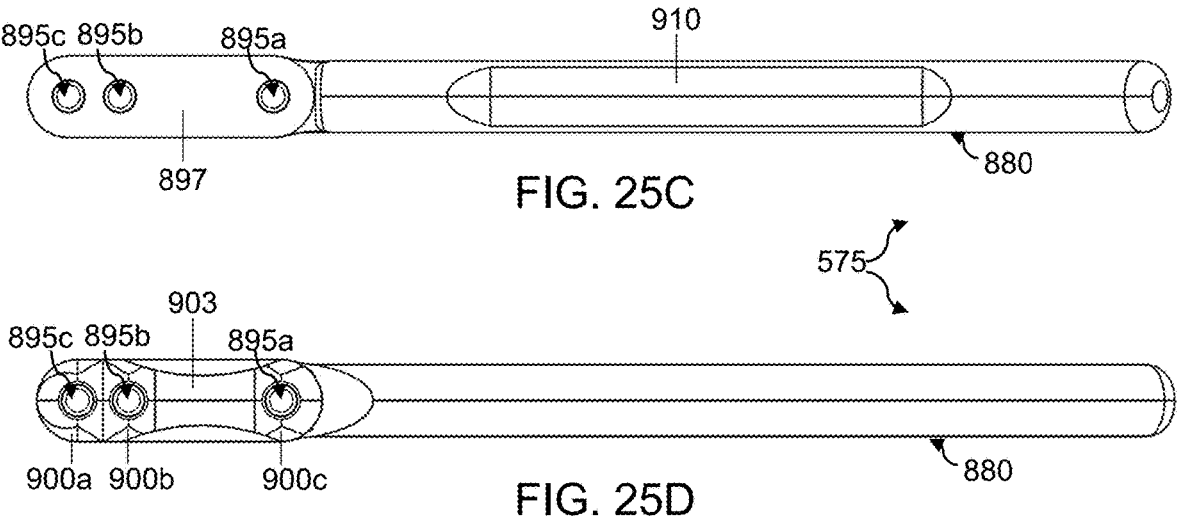
895c 895b          895a          910
897
FIG. 25C
880
575
903
895c 895b          895a
880
900a 900b          900c
FIG. 25D
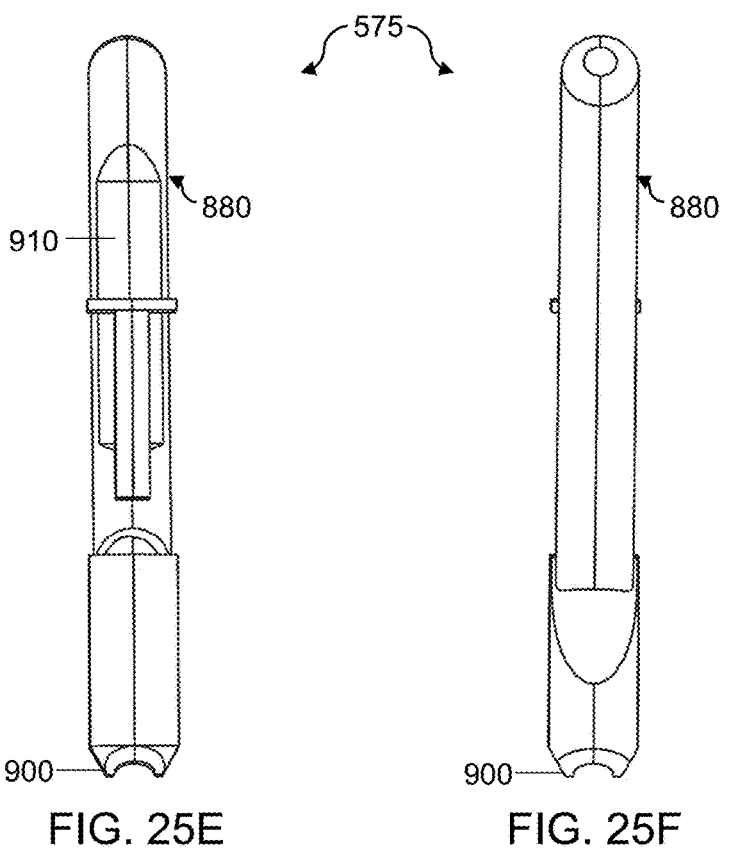
575
910          880          880
900          900
FIG. 25E          FIG. 25F

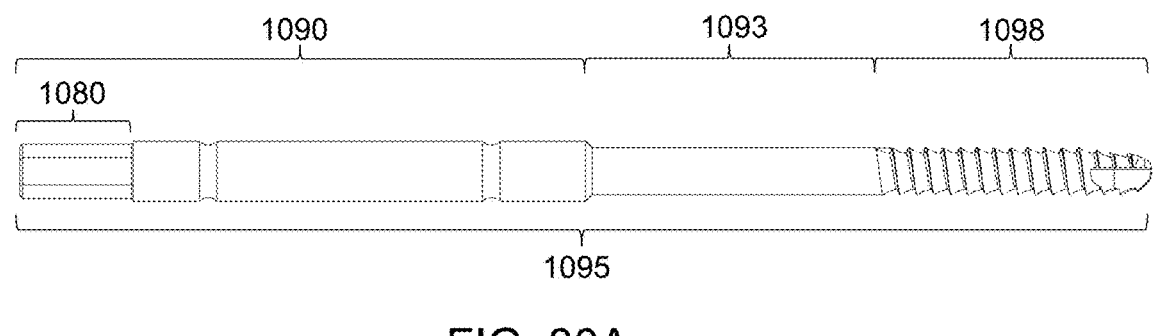
FIG. 30A
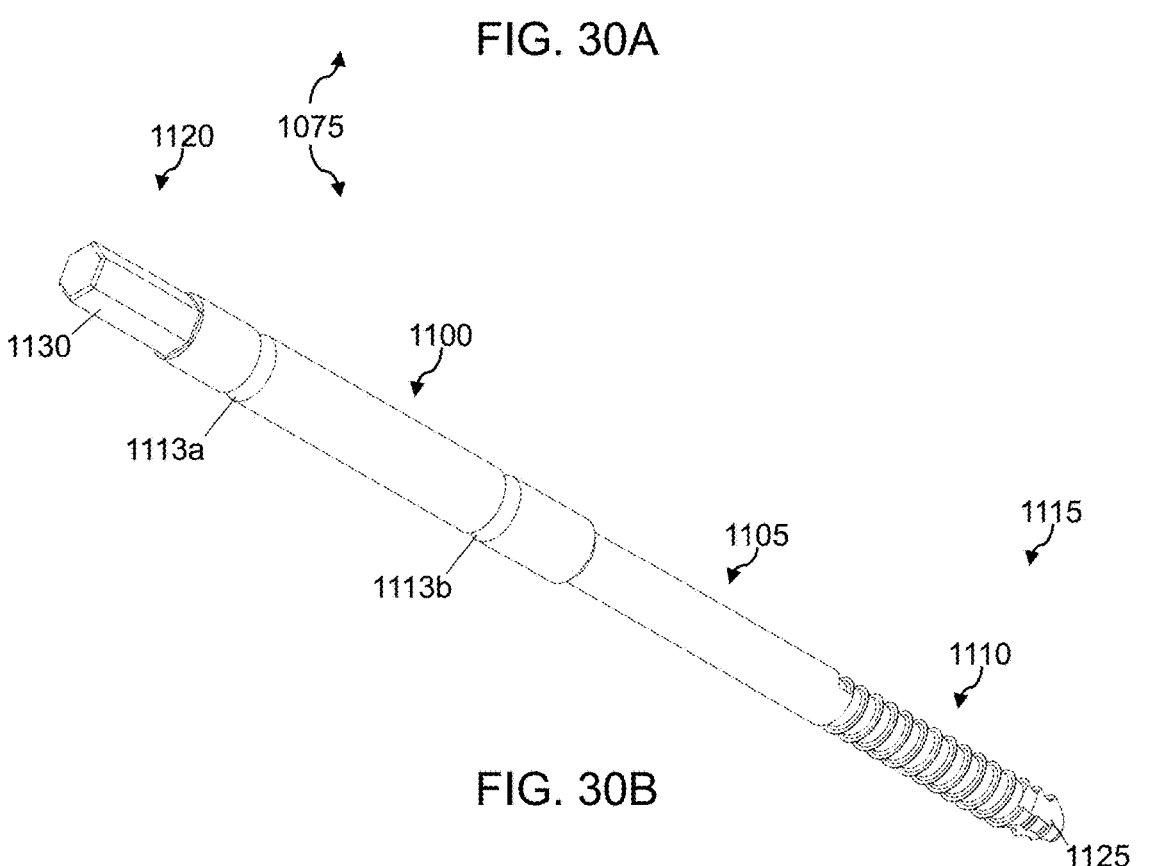
FIG. 30B
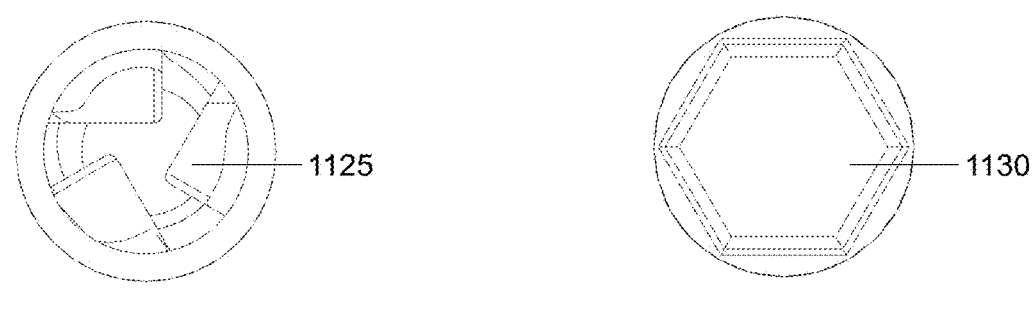
FIG. 30C                    FIG. 30D

EXTERNAL FIXATOR APPARATUS AND METHOD

CROSS-REFERENCE TO RELATED APPLICATIONS

This application is a continuation of International Appl. No. PCT/US2023/010859, filed Jan. 16, 2023, entitled "External Fixator Apparatus and Method," which claims priority benefit to Prov. Appl. No. 63/299,490, filed on Jan. 14, 2022, entitled "External Fixator Apparatus & Method", and Prov. Appl. No. 63/367,390, filed on Jun. 30, 2022, entitled "External Fixator Apparatus & Method," which are incorporated herein by reference in their entireties.

TECHNICAL FIELD

The invention relates to methods, devices, and systems for an improved external fixator adapted for distal radius fractures. More specifically, the improved external fixator relates to a reduced profile external fixator with or without multi-axial translational motion to achieve an optimal outcome and anatomical position.

BACKGROUND OF THE INVENTION

Distal radius fractures (DRF) are a common type of acute traumatic fracture. Among an array of options, traditional external fixation is a popular treatment method of DRF for the reduction and stabilization of DRFs. External fixation usually involves reduction (putting the broken bone back into position) and immobilizing the wrist with metal pins or fixation screws that are driven into bone, generally via small skin incisions, on either side of the fracture (e.g., "bridging" the fracture). These pins or screws are then fixed and/or secured externally into the frame of a traditional external fixator. The external fixator holds the bony fragments in position while the bone heals. Unfortunately, the traditional external fixator designs are usually large, bulky, heavy, stiff, and are accompanied with various complications, including failure to optimally restore bone joint alignment and/or motion, failure to maintain reduction, visualization and/or failures occurring at the bone-pin interface (e.g., too heavy).

BRIEF SUMMARY OF THE INVENTION

As a result, an improved external fixator is desired that reduces the weight, the overall profile, improves visualization of the fractured region and provides for multi-axial translational motion to easily permit reduction of fractured bones and adjustment of flexion/extension, supination/pronation, radial/ulnar deviation, and/or any combination thereof during surgery and post-procedure follow-ups of the involved extremity to potentially restore bone alignment and/or motion. Furthermore, the improved external fixator may also include one or more quick release mechanisms to increase efficiency of installation and adjustments.

In one embodiment, the external fixator system comprising: a distal frame assembly, the distal frame assembly includes a distal frame and a distal compression bracket, the distal compression bracket being spaced apart and secured to the distal frame to create a distal elongated opening; a proximal frame assembly, the proximal frame assembly includes a proximal frame and a proximal compression bracket, the proximate compression bracket being spaced apart and secured to the proximal frame to create a proximal elongated opening; a lockable, multi-axial or polyaxial joint between the distal frame assembly and the proximal frame assembly; and a first fixation screw and a second fixation screw, each of the first and second fixation screws being sized and configured to be disposed within the elongated distal opening and elongated proximal opening, each of the first and second pins engaging a portion of bone on opposing sides of the fracture site; the at least a portion of the distal compression bracket being movable relative to the distal frame to compress the first fixation screw between the distal compression bracket and the distal frame into a fixed or locked position, and the at least a portion of the proximal compression bracket being movable relative to the proximal distal frame to compress the second fixation screw between the proximal compression bracket and the proximal frame into a fixed or locked position.

In another embodiment, the external fixator system comprising: a distal frame assembly, the distal frame assembly includes a distal frame and a distal compression bracket, the distal compression bracket being spaced apart and secured to the distal frame to create a distal elongated opening; a proximal frame assembly, the proximal frame assembly includes a proximal frame and a proximal compression bracket, the proximate compression bracket being spaced apart and secured to the proximal frame to create a proximal elongated opening; a lockable, multi-axial or polyaxial joint between the distal frame assembly and the proximal frame assembly; and a first fixation screw and a second fixation screw, each of the first and second fixation screws being sized and configured to be disposed within the elongated distal opening and elongated proximal opening, each of the first and second pins engaging a portion of bone on opposing sides of the fracture site; the at least a portion of the distal compression bracket having a first movement relative to the distal frame to release compression of the first fixation screw between the distal compression bracket and the distal frame into an unlocked position, and the at least a portion of the proximal compression bracket having a second movement relative to the proximal frame to release compression of the second fixation screw between the proximal compression bracket and the proximal frame into a unlocked position.

In another embodiment, the external fixator system comprising: a distal frame assembly, the distal frame assembly includes a distal frame and a distal compression bracket, the distal compression bracket being spaced apart and secured to the distal frame to create a distal elongated opening; a proximal frame assembly, the proximal frame assembly includes a proximal frame and a proximal compression bracket, the proximate compression bracket being spaced apart and secured to the proximal frame to create a proximal elongated opening, a lockable, multi-axial or polyaxial joint between the distal frame assembly and the proximal frame assembly; and a first fixation screw, the first fixation screw being sized and configured to be disposed within the elongated distal opening, a portion of the distal compression bracket being secured to a portion of the distal frame to compress the first fixation screw between the distal frame and the distal compression bracket and fix the first fixation screw to a first location; and a second fixation screw, the second fixation screw being sized and configured to be disposed within the elongated proximal opening, a portion of the proximal compression bracket being secured to a portion of the proximal frame to compress the second fixation screw between the proximal compression bracket and the proximal frame and fix the second fixation screw to a second location; the at least a portion of the distal compression bracket having a first movement relative to the distal frame from an unlocked position to a locked position, the unlocked position allows the distal compression bracket to release the first fixation screw from compression, and the locked position re-compresses the fixation screw between the distal compression bracket and the distal frame; the at least a portion of the proximal compression bracket having a second movement relative to the proximal frame from an unlocked position to a locked position, the unlocked position allows the proximal compression bracket to release the second fixation screw from compression, and the locked position re-compresses the fixation screw between the proximal compression bracket and the distal frame.

In another embodiment, the external fixator system comprising: a distal frame assembly, the distal frame assembly includes a distal frame and a distal compression bracket, the distal compression bracket being spaced apart and secured to the distal frame to create a distal elongated opening; a proximal frame assembly, the proximal frame assembly includes a proximal frame and a proximal compression bracket, the proximate compression bracket being spaced apart and secured to the proximal frame to create a proximal elongated opening; a lockable, multi-axial or polyaxial joint between the distal frame assembly and the proximal frame assembly, the polyaxial joint comprises a ball component and a socket component, the ball component is disposed within the socket component to allow poly axial motion, the ball component is movable between an unlocked position and a locked position which the ball component expands within the socket component to restrict polyaxial movement/motion; and a first fixation screw and a second fixation screw, each of the first and second fixation screws being sized and configured to be disposed within the elongated distal opening and elongated proximal opening, each of the first and second pins engaging a portion of bone on opposing sides of the fracture site; the at least a portion of the distal compression bracket being movable relative to the distal frame to compress the first fixation screw between the distal compression bracket and the distal frame into a fixed or locked position, and the at least a portion of the proximal compression bracket being movable relative to the proximal distal frame to compress the second fixation screw between the proximal compression bracket and the proximal frame into a fixed or locked position.

In another embodiment, the external fixator system comprising: a first or distal frame assembly, the distal frame assembly comprises a distal frame, a ball component and first or distal bracket, the ball component is disposed at one end of the distal frame, the first or distal bracket being spaced apart and secured to a portion of the distal frame that creates an elongated distal opening; a second or proximal frame assembly, the proximal frame assembly comprises a proximal frame, a socket component and second or proximal bracket, the socket component disposed at one end of the proximal frame, the second or proximal bracket being spaced apart and secured to a portion of the proximal frame to create an elongated proximal opening, the ball component of the distal frame assembly is disposed within the socket component of the proximal frame assembly to allow multi-axial or polyaxial translational motion of the distal frame assembly relative to the proximal frame assembly; and a plurality of fixation screws, each of the plurality of fixation screws being sized and configured to be disposed within the elongated distal opening and elongated proximal opening, the plurality of fixation screws engaging a portion of bone on opposing sides of the fracture site.

In another embodiment, the external fixator system comprising: a first or distal frame assembly, the distal frame assembly comprises a distal frame, a ball component and first or distal bracket, the ball component is disposed at one end of the distal frame, the first or distal bracket being spaced apart and secured to a portion of the distal frame that creates an elongated distal opening; a second or proximal frame assembly, the proximal frame assembly comprises a proximal frame, a socket component and second or proximal bracket, the socket component disposed at one end of the proximal frame, the second or proximal bracket being spaced apart and secured to a portion of the proximal frame to create an elongated proximal opening, the ball component of the distal frame assembly is disposed within the socket component of the proximal frame assembly to create a multi-axial or polyaxial joint that is movable from a first position that is unlocked to allow polyaxial motion of the distal frame assembly relative to the proximal frame assembly, to a second position that is a locked position which restricts the polyaxial motion of the proximal frame assembly relative to the distal frame assembly; and a plurality of fixation screws, the plurality of fixation screws being sized and configured to be disposed within the elongated distal opening and elongated proximal opening, the plurality of fixation screws engaging a portion of bone on opposing sides of the fracture site.

In another embodiment, the external fixator system comprising: a first or distal frame assembly, the distal frame assembly comprises a distal frame, a ball component and first or distal bracket, the ball component is disposed at one end of the distal frame, the first or distal bracket being spaced apart and secured to a portion of the distal frame that creates an elongated distal opening; a second or proximal frame assembly, the proximal frame assembly comprises a proximal frame, a socket component and second or proximal bracket, the socket component disposed at one end of the proximal frame, at least a portion of the socket component includes a notch that is positioned to be substantially aligned with the through-hole, the second or proximal bracket being spaced apart and secured to a portion of the proximal frame to create an elongated proximal opening, the ball component of the distal frame assembly is disposed within the socket component of the proximal frame assembly to create a multi-axial or polyaxial joint that is movable from a first position that is unlocked to allow polyaxial motion of the distal frame assembly relative to the proximal frame assembly, to a second position that is a locked position which restricts the polyaxial motion of the proximal frame assembly relative to the distal frame assembly; and a first fixation screw and a second fixation screw, each of the first and second fixation screws being sized and configured to be disposed within the elongated distal opening and elongated proximal opening, each of the first and second pins engaging a portion of bone on opposing sides of the fracture site; the at least a portion of the distal bracket being movable relative to the distal frame to compress the first fixation screw between the distal bracket and the distal frame into a fixed or locked position, and the at least a portion of the proximal bracket being movable relative to the proximal distal frame to compress the second fixation screw between the proximal bracket and the proximal frame into a fixed or locked position.

In another embodiment, the external fixator system comprising: a first or distal frame assembly, the distal frame assembly comprises a distal frame, a ball component and first or distal bracket, the ball component is disposed at one end of the distal frame, the first or distal bracket being secured to a portion of the frame to leave an elongated distal opening, the distal bracket slidably moves relative to the distal frame; a second or proximal frame assembly, the proximal frame assembly comprises a proximal frame, a socket component and second or proximal bracket, the socket component disposed at one end of the proximal frame, the second or proximal bracket being secured to a portion of the proximal frame to leave an elongated proximal opening, the second or proximal bracket slidably moves relative to the proximal frame; the ball component of the distal frame assembly is disposed within the socket component of the proximal frame assembly to create a multi-axial or polyaxial joint that is movable from a first position that is unlocked to allow polyaxial motion of the distal frame assembly relative to the proximal frame assembly, to a second position that is a locked position which restricts the polyaxial motion of the proximal frame assembly relative to the distal frame assembly; a first fixation screw, the first fixation screw being sized and configured to be disposed within the elongated distal opening, a portion of the distal compression bracket being coupled to a portion of the distal frame to compress the first fixation screw between the distal frame and the distal compression bracket and fix the first fixation screw to a first location; and a second fixation screw, the second fixation screw being sized and configured to be disposed within the elongated proximal opening, a portion of the proximal bracket being coupled to a portion of the proximal frame to compress the second fixation screw between the proximal bracket and the proximal frame and fix the second fixation screw to a second location; the at least a portion of the distal bracket including a first quick release movement relative to the distal frame from an unlocked position to a locked position, the unlocked position allows the distal bracket to release the first fixation screw from compression, and the locked position re-compresses the fixation screw between the distal compression bracket and the distal frame; the at least a portion of the proximal bracket including a second quick release movement relative to the proximal frame from an unlocked position to a locked position, the unlocked position allows the proximal bracket to release the second fixation screw from compression, and the locked position re-compresses the fixation screw between the proximal bracket and the proximal frame.

In another embodiment, the external fixator system comprises: a distal frame assembly, the distal frame assembly comprises a distal frame, a distal compression bracket, the distal compression bracket; a proximal frame assembly, the proximal frame assembly comprises a proximal frame, the proximal frame includes longitudinal axis, a first end, a second end, a window, a first row of openings and a second row of openings, the first row of openings and the second row of openings disposed onto the proximal frame, the first row of openings comprises a first plurality of openings, each of the first plurality of openings are spaced along the longitudinal axis of the proximal frame, the second row of openings comprises a second plurality of openings, each of the second plurality of openings are spaced along the longitudinal axis of the proximal frame; and a polyaxial joint between the distal frame assembly and the proximal frame assembly, the polyaxial joint comprises a ball component, a socket component and a locking collar, the ball component engages with the socket component to create the polyaxial joint, the polyaxial joint is movable from an unlocked position to a locked position, the unlocked position allows the ball component to be movable relative to the socket component to create polyaxial motion, and the locked position prevents the ball component to be movable relative to the socket component. The external fixator system comprises a disposable, a sterilizable, and/or a disposable and sterilizable external fixator system.

In another embodiment, the method to reduce distal radius fractures comprises the steps of: obtaining an external fixation system, the external fixation system comprises a proximal frame assembly, a distal frame assembly, and a polyaxial joint between the proximal frame assembly and the distal frame assembly, one or more proximal fixation screws and one or more distal fixation screws; securing the one or more proximal fixation screws to a first bone position with the proximal frame assembly; inserting one or more distal fixation screws in a second bone position; aligning the distal frame assembly over the one or more distal fixation screws at the second bone position, the distal frame assembly comprising a distal frame, a distal compression bracket, and one or more fasteners; performing one or more first adjustments of at least one fracture; securing the one or more distal fixation screws at the second bone position between the distal frame and distal compression bracket to prevent movement of the one or more distal fixation screws; performing one or more secondary adjustments of the at least one fracture to obtain an optimal wrist position; and locking a polyaxial joint of the external fixator assembly at the optimal wrist position.

BRIEF DESCRIPTION OF THE SEVERAL VIEWS OF THE DRAWINGS

FIGS. 12A-12E depict various plan views of one embodiment of a driving tool handle;

FIG. 12F depicts a cross-sectional view of the driving tool handle of FIG. 12D;

FIGS. 15A-15D depicts various plan views of one embodiment of a drill wire;

FIGS. 21A-21I depicts various plan views of an alternate embodiment of a proximal frame;

FIGS. 22A-22F depicts various plan views of one embodiment of a locking collar;

FIGS. 25A-25G depict various plan views of an alternate embodiment of a guide tool;

FIG. 25H depicts a cross-sectional view of the guide tool of FIGS. 25A-25G;

Figures 29A, 29B, 29C, 29D, 29E:
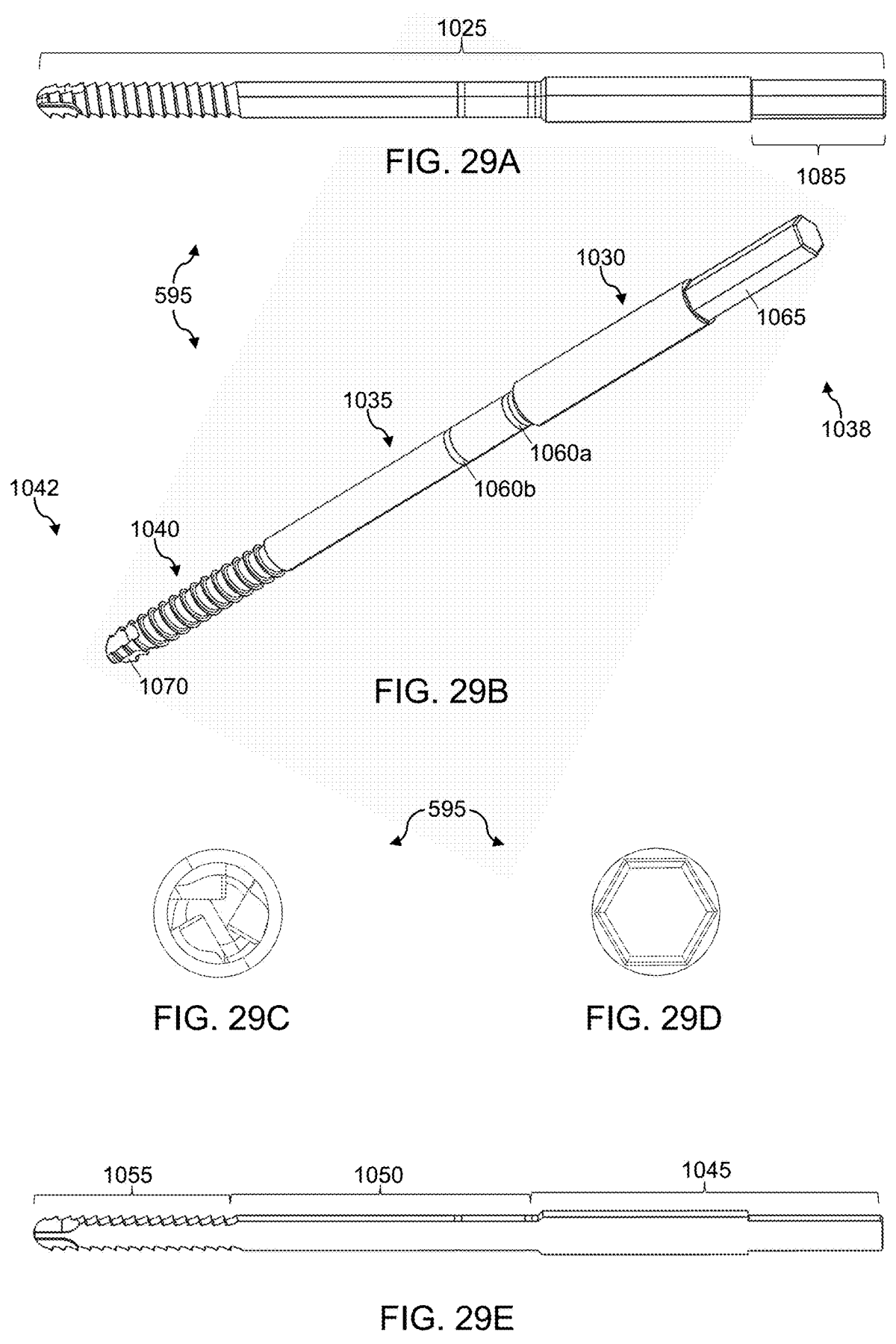

FIGS. 29A-29D depicts various plan views of an alternate embodiment of a fixation screw;

FIG. 29E depicts a cross-sectional view of the alternate embodiment of a fixation screw of FIGS. 29A-29D; and FIGS. 30A-30D depicts various plan views of an alternate embodiment of a fixation screw;

DETAILED DESCRIPTION OF THE INVENTION

Figure 1:
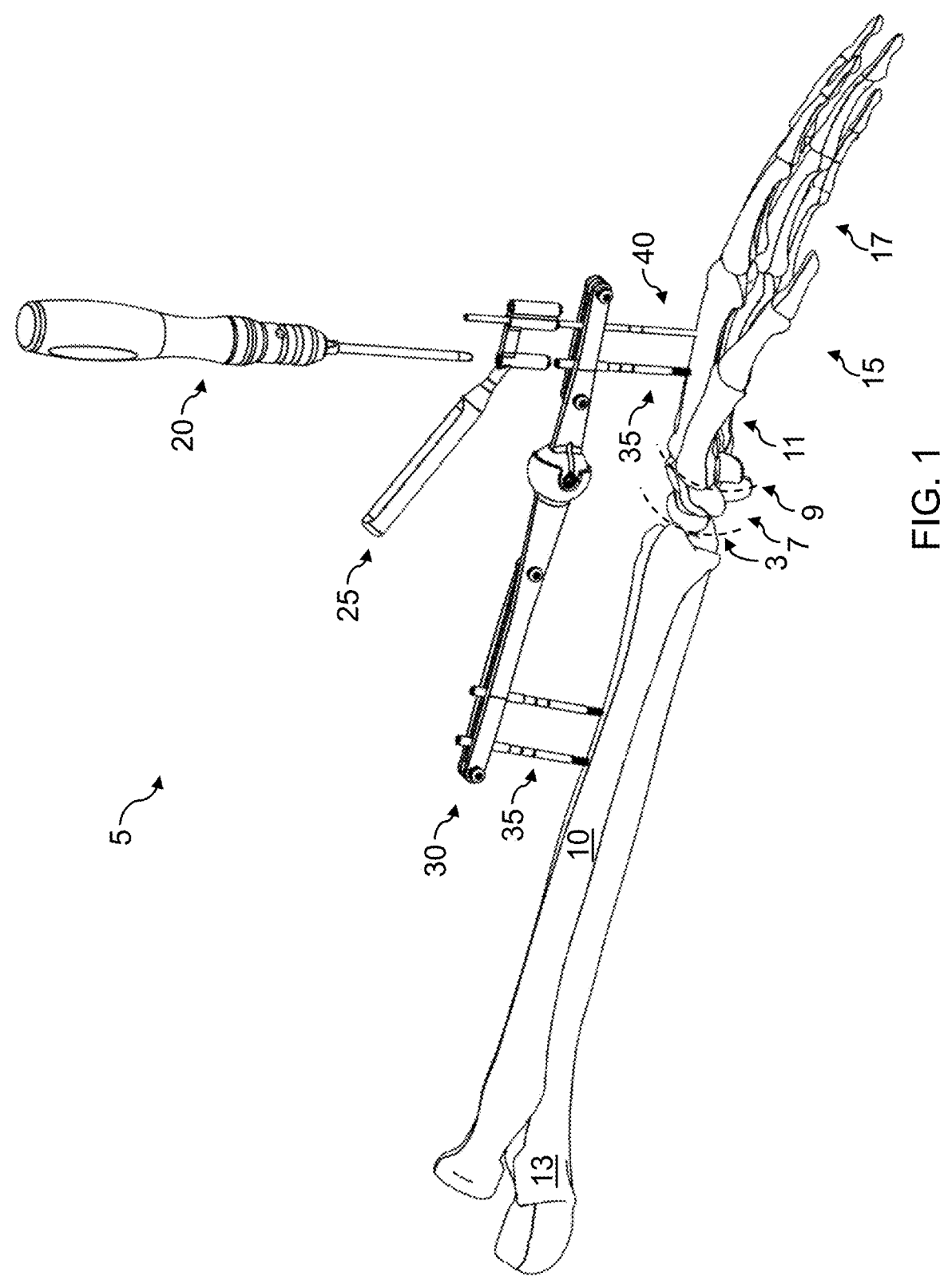
FIG. 1 depicts an isometric view of one embodiment of an external fixator system.
Figures 2A, 2B:
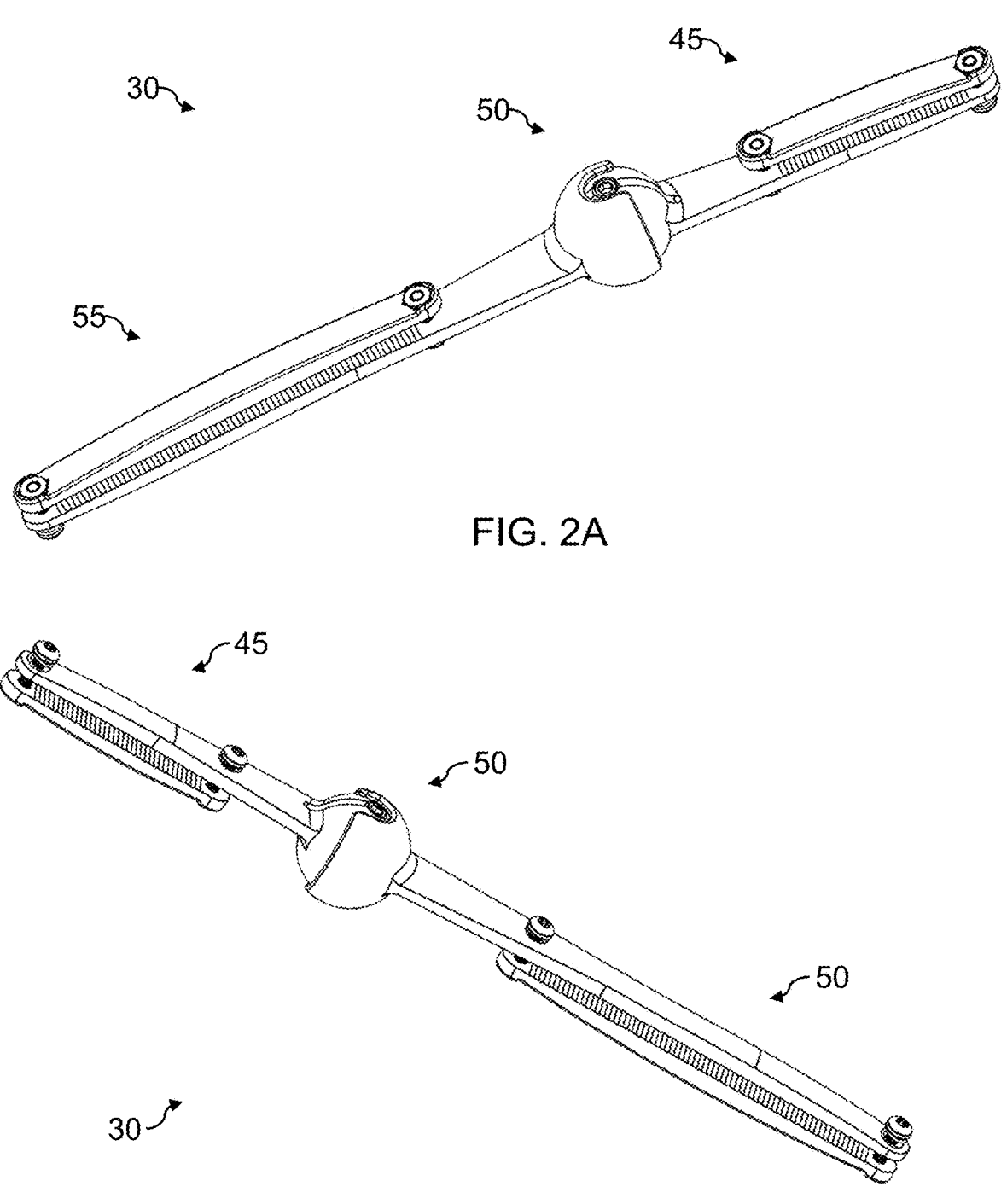
FIGS. 2A-2F depicts various plan views of one embodiment of an external fixator assembly.
Figures 2C, 2D:
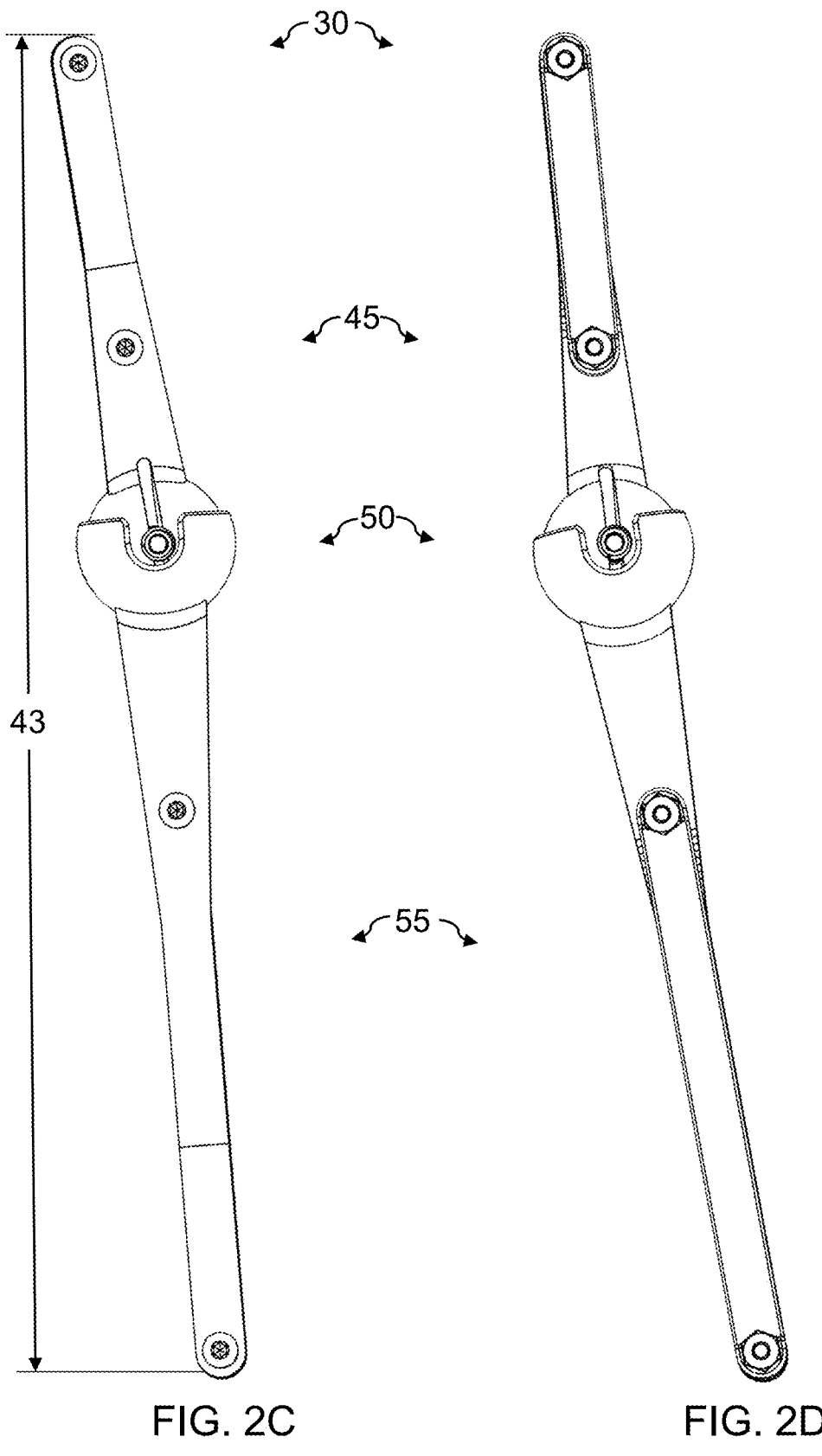
Figures 2E, 2F:
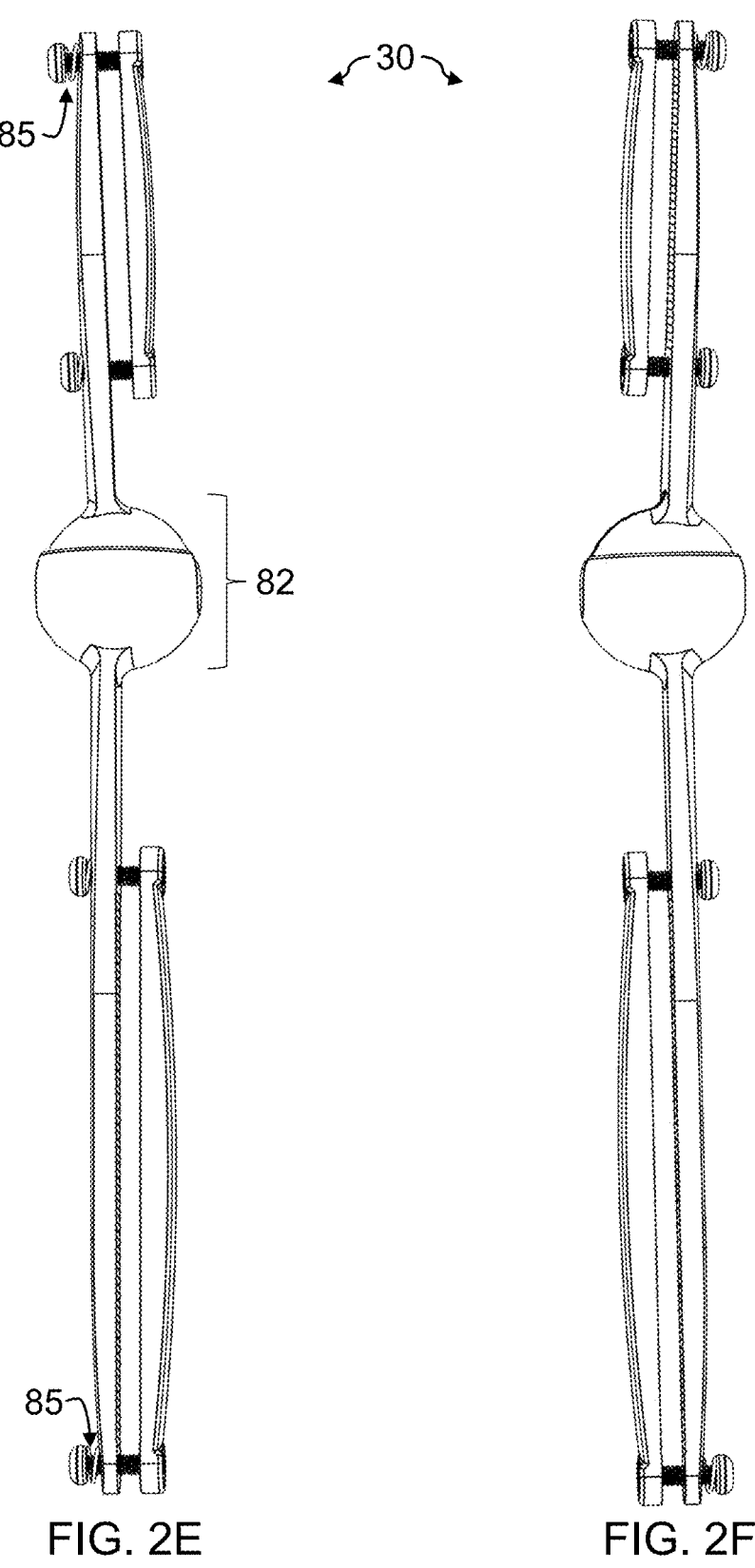

FIGS. 1, 16, 17A-17B, 30A-30B, 31A-31B and 32 depicts an isometric view of different embodiments of an external fixator system 5, 565. The external fixator system 5, 565 may be utilized for the application of reducing distal radius fractures. The external fixation system 5, 565 may involve the reduction (putting the broken bone(s) back into position) and immobilization of the wrist with fixation screws 35, 595, 1075 that are driven into the hand bones 15 (e.g., metacarpals) and the radius 10, which are on either side of the fracture (e.g., "bridging" or straddling the fracture). The bone model includes forearm bones, a wrist and a hand 15. The forearm bones include the ulna 10 and the radius 13. The wrist includes the radiocarpal joint 3, one or more carpal bones 7, and the carpometacarpal joint 9 and/or the trapeziometacarpal joint (not shown). The hand 15 includes the metacarpals 11 and the phalanges 17. However, the external fixator system 5, 565 may be adapted to correct other fractures in other bones of a patient's anatomy, as well as be used to augment fracture fixation using K-wires, volar plate, dorsal plate, additional fixation screws, and/or any combination thereof.

The external fixator assemblies 30, 570, 1140 are desirably designed to reduce the weight compared to traditional commercially available external fixator assemblies. The external fixator assemblies 30, 570, 1140 and/or a portion of the external fixator assembly 30, 570, 1140 may comprise light-weight materials, including lightweight metals and/or polymers. Furthermore, the external fixator assembly 30, 570, 1140 may comprise and/or a portion of the external fixator assembly 30, 570, 1140 may comprise a window 635,1225 that removes a portion of the material to further reduce the weight of the external fixator assemblies. Placing a window 30,570,1140 in the distal assembly 45, 605, 1160 and/or the proximal assembly 55,610,1145 is counterintuitive due to the required strength that is required to neutralize the magnitude and physiological loads on the distal radius.

The external fixator assemblies 30, 570, 1140 are desirably designed to reduce the overall profile compared to traditional commercially available external fixator assemblies. Due to the unique design of the external fixator assemblies 30, 570, 1140, the external fixator assemblies 30, 570, 1140 can be positioned close to the skin to increase the stability against bending loads by reducing the lever arm from the neutral joint axis. The clearance distance above the skin may comprise at least 3 mm and/or a range of 3 mm to 5 mm.

the external fixator assemblies 30, 570, 1140 may comprise enhanced visualization features compared to traditional commercially available external fixator assemblies. The enhanced visualization features allow for visualization of the fracture site, the distended or reduced fracture site, and/or the radiocarpal joint 3, during surgery. The enhanced visualization features incorporated into the external fixator assemblies 30, 570, 1140 should not interfere with standard imaging. In one embodiment, the enhanced visualization features may comprise radiotranslucent materials, a window 635,1225 and/or decreased polyaxial joint 50, 600, 1150 profile. In one embodiment, at least a portion of the external fixator assemblies 30, 570, 1140 may comprise a translucent or radiotransparent material or substantially translucent or radiotransparent material. The translucent or radiotransparent material would allow radiation or X-rays to pass more freely through the external fixator assemblies 30, 570, 1140 during imaging, resulting in the appearance black features on the exposed film. In another embodiment, the external fixator assemblies 30, 570, 1140 may comprise a window 635,1225 that extends along its longitudinal axis and at least a portion of the window 635,1225 is positioned over the fracture site and/or the distended/reduced fracture site. In another embodiment, the polyaxial joint 30, 570, 1140 may comprise a polyaxial joint width 82, 602, 1152 that is low-profile. The polyaxial joint width 82, 602, 1152 is smaller than the wrist distance 22 between the radiocarpal joint 3 and the carpometacarpal joint 9 to prevent obstruction of the fracture site and/or the distended/reduced fracture site. The polyaxial joint width 82, 602, 1152 is smaller than the smallest wrist distance 22 between the radiocarpal joint 3 and the carpometacarpal joint 9 to prevent obstruction of the fracture site and/or the distended/reduced fracture site. Alternatively, the polyaxial joint width 82, 602, 1152 is positioned over the carpals away from and/or adjacent to the fracture site and/or the distended/reduced fracture site to prevent obstruction of the fracture site and/or the distended/reduced fracture site.

The external fixator assembly 30, 570, 1140 comprises universal adjustability or polyaxial adjustability. The external fixator assembly 30, 570, 1140 comprises a multi-axial or polyaxial joint 5050, 600, 1150 that allows for polyaxial manipulation, alignment and reduction of the fracture(s) from 0 degrees to 360 degrees and/or from 0 degrees to 270 degrees. This allows for multi-axial translational motion for better access to the injury site for wound care, permit adjustments of the bones and/or wrist joint, and mobilization of the involved extremity and/or wrist joint during surgery and post-operative care. More specifically, the adjustments may comprise an optimal wrist position through the manipulation of flexion, extension, the radial deviation, ulnar deviation, the pronation, supination and/or any combination thereof using the polyaxial joint 50, 600, 1150. The polyaxial joint 50, 600, 1150 may further comprise a lockable polyaxial joint 50, 600, 1150.

The polyaxial joint 50, 600, 1150 comprises a ball component 105, 665,1180 and a socket component 70, 645, 1215. The ball component 105, 665,1180 is disposed within the socket component 70, 645, 1215 to allow polyaxial or multi-axial translational motion. The polyaxial motion includes motion of at least 90 degrees or greater. In another embodiment, the ball component 105, 665,1180 of the distal frame assembly 45, 605, 1160 is disposed within the socket component 70, 645, 1215 of the proximal frame assembly 55, 610, 1145 to create a multi-axial or polyaxial joint 50, 600, 1150 that is movable from an unlocked position to a locked position, the unlocked position allows the ball component 105, 665,1180 to be movable relative to the socket component 70, 645, 1215 to create polyaxial motion and the locked position that rotates the ball component 105, 665, 1180 within the socket component 70, 645, 1215 to contact or engage a portion of an inner diameter surface of the locking collar 650,1205 to create an interference fit that locks the ball component 105, 665,1180 to the socket component 70, 645, 1215. In another embodiment, the ball component 105, 665,1180 of the distal frame assembly 45, 605, 1160 is disposed within the socket component 70, 645, 1215 of the proximal frame assembly 55, 610, 1145 to create a multi-axial or polyaxial joint 50, 600, 1150 that is movable from an unlocked position to a locked position, the unlocked position allows the ball component 105, 665,1180 to be movable relative to the socket component 70, 645, 1215 to create polyaxial motion and the locked position occurs when the locking fasteners 625,1230 contact a portion of the ball component 105, 665, 1180 to create friction and prevent movement.

The improved external fixator assembly 30, 570, 1140 further increases surgical efficiency and post-operative care than compared to traditional commercially available external fixator assemblies. The external fixator assembly 30, 570, 1140 may comprise quick release mechanisms 85 that allows the surgeon to compress and/or distract relevant bones without loosening the fasteners on the external fixator assembly 30, 570, 1140. The surgeon may compress the quick release mechanisms 85 on the proximal assembly 55, 610, 1145 and/or the distal assembly 45, 605, 1160 to release the pressures placed on the fixation screws 35 to allow the surgeon to manually distract or compress the relevant portions of the bones, thus allowing the fixation screws 35, 595, 1075 to slide in desired directions along or substantially along the longitudinal axis of the external fixator assembly 30, 570, 1140. The quick release mechanisms 85 may comprise a spring-loaded mechanism, a push-pull pin, a positive-locking pin, a ball-lock pin, push-button pin, detent pins, and/or any combination thereof. The spring-loaded mechanism may further comprise a compression spring.

The external fixator assembly 45, 605, 1160 reduces the total number of components needed for the surgical technique. The improved external fixator assembly 30 may also comprise a "one-size fits all." The external fixator assembly 30, 570, 1140 may be available in a single length 43, 615, 1165 for fracture positioning and patient needs rather than have multiple lengths available compared to traditional fixator assemblies. Alternatively, the external fixator assembly 30, 570, 1140 may comprise multiple lengths to accommodate the patient's anatomy. Multiple lengths may include small, medium and large.

Different Embodiments of the External Fixator System and Assemblies

The external fixator system 5, 565 comprises the external fixator assembly 30, 570, 1140 and at least two fixation screws 35, 595, 1075. The external fixator system 5, 565 may further comprise at least one or more of the following: a guide tool 25, 575, a guide insert 580, a driving tool 20, 590, and a drill wire 40, and/or any combination thereof. The external fixator assembly 30, 570, 1140 comprises a proximal frame assembly 55, 610, 1145 a distal frame assembly 45, 605, 1160, a polyaxial joint 50, 600, 1150 disposed between the proximal frame assembly 55, 610, 1145 and the distal frame assembly 45, 605, 1160.

FIGS. 2A-2F depict various plan views of one embodiment of an external fixator assembly 30. The external fixator assembly 30 comprises a distal frame assembly 45, a proximal frame assembly 55, and a polyaxial or multi-axial joint 50. The polyaxial joint 50 is positioned between the distal frame assembly 45 and the proximal frame assembly 55. At least a portion of the external fixator assembly 30 is secured over the radius 13 and extends across the carpal bones of the wrist 7 and at least a portion of the external fixator assembly 30 is secured onto the metacarpals 11. The polyaxial joint 50 should be disposed between the radiocarpal joint 3 and the carpometacarpal joint 9 and/or the trapeziometacarpal joint (not shown). Additionally, the polyaxial joint 50 comprises a total joint width 82, 602, 1152 that is equal to or less that the area of the carpal bones 7 of the wrist and/or an average joint distance 22 that is defined as the distance between the radiocarpal joint 3 and the carpometacarpal joint 9 and/or the trapeziometacarpal joint (not shown).

Figure 3:
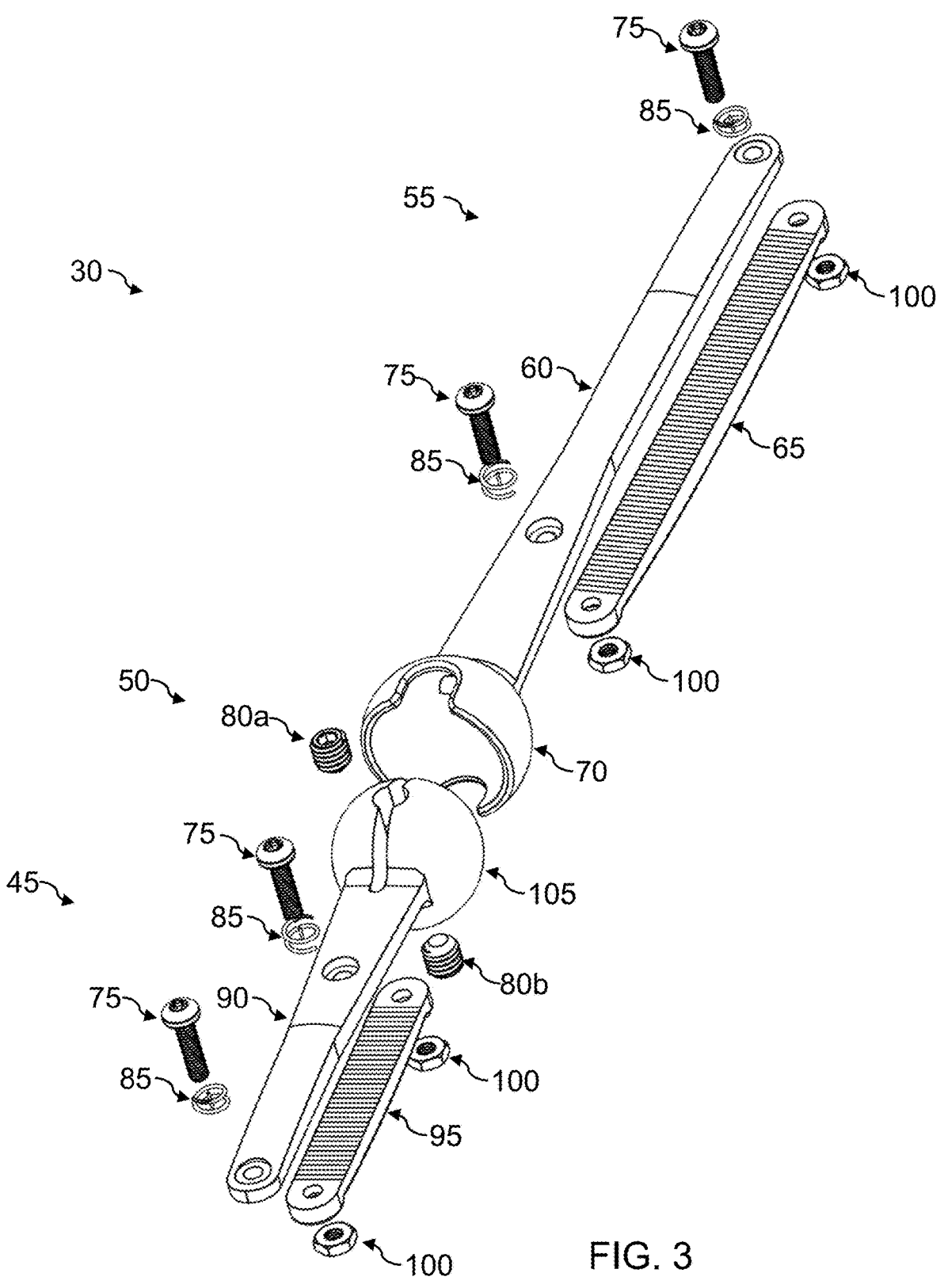
FIG. 3 depicts an exploded view of one embodiment of an external fixator assembly.

FIG. 3 depicts an exploded view of one embodiment of an external fixator assembly 30. The external fixator assembly 30 comprises a distal frame assembly 45, a proximal frame assembly 55, and a polyaxial or multi-axial joint 50. The polyaxial joint 50 is positioned between the distal frame assembly 45 and the proximal frame assembly 55. The distal frame assembly 45 comprises a distal frame 90, a distal compression bracket 95, a first plurality of fasteners 75 and a second plurality of fasteners 80a, 80b. The proximal frame assembly 55 may comprise a proximal frame 60, a proximal compression bracket 65, and a plurality of fasteners 75. The distal frame assembly 45 and/or the proximal frame assembly 55 may further comprise one or more quick release mechanisms 85.

Figure 4A:
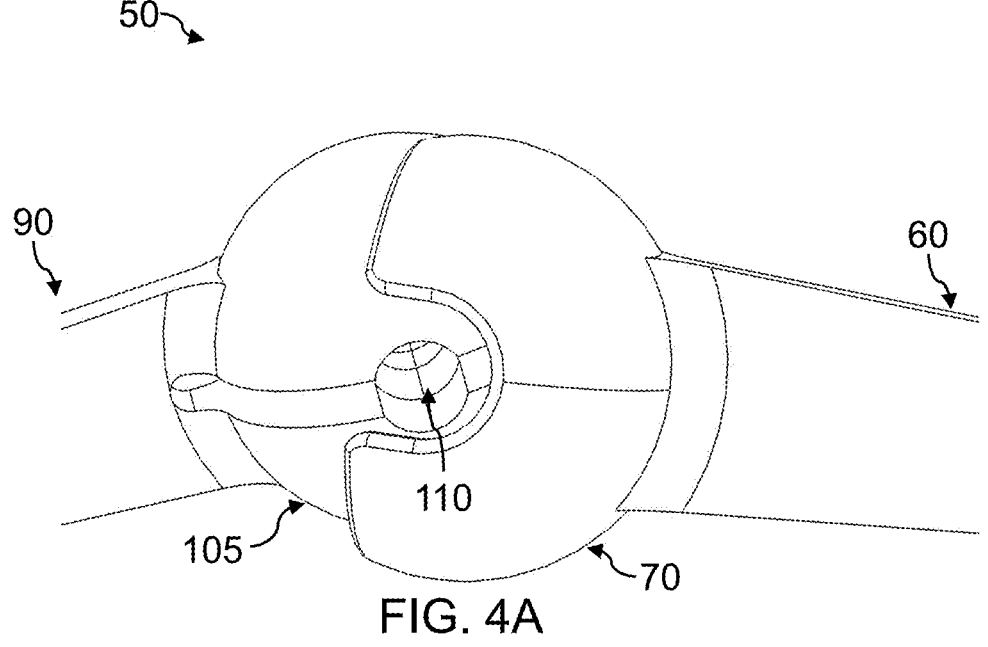
FIGS. 4A-4B depicts isometric views of one embodiment of the lockable polyaxial joint of the external fixator assembly.
Figure 4B:
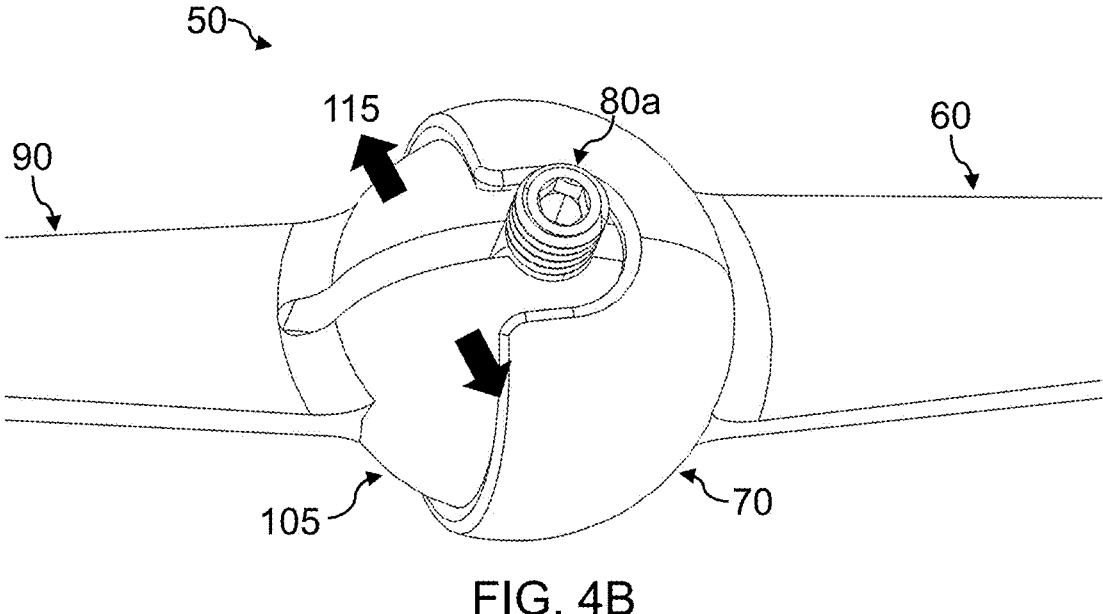

In one embodiment, the external fixator assembly 30 comprises a polyaxial or multi-axial joint 50. The polyaxial joint 50 allows for translational motion in different axis for adjustment and alignment of the relevant portions of the bone(s) while reducing the fracture as shown in FIGS. 4A-4B. The polyaxial joint 50 comprises a ball component 105 and a socket component 70. The ball component 105 is disposed within the socket component 70 to allow polyaxial or multiaxial translational motion from 0 degrees to 360 degrees and/or 0 degrees to 270 degrees. The ball component 105 is disposed and/or positioned on at least one end of the distal frame 90. The socket component 70 is disposed on at least one end of the proximal frame 60.

In another embodiment, the ball component 105 is movable relative to the socket component 70. The ball component 105 is movable from a first position to a second position, which the second position allows the threading or rotation of the at least one locking fastener 80a, 80b to drive the ball component diameter to expand and contact and engage an inner surface of the socket component 70 to cause an increase of friction to restrict or eliminate any polyaxial translational motion. In another embodiment, the ball component 105 is movable relative to the socket component 70. The ball component 105 is movable from a first position to a second position, which the second position allows the at least one locking fastener 80a, 80b to be inserted into the at least one tapered opening 110 to expand the ball component diameter to contact and engage an inner surface of the socket component 70 to cause an increase of friction to restrict or eliminate any polyaxial translational motion.

Figure 5A:
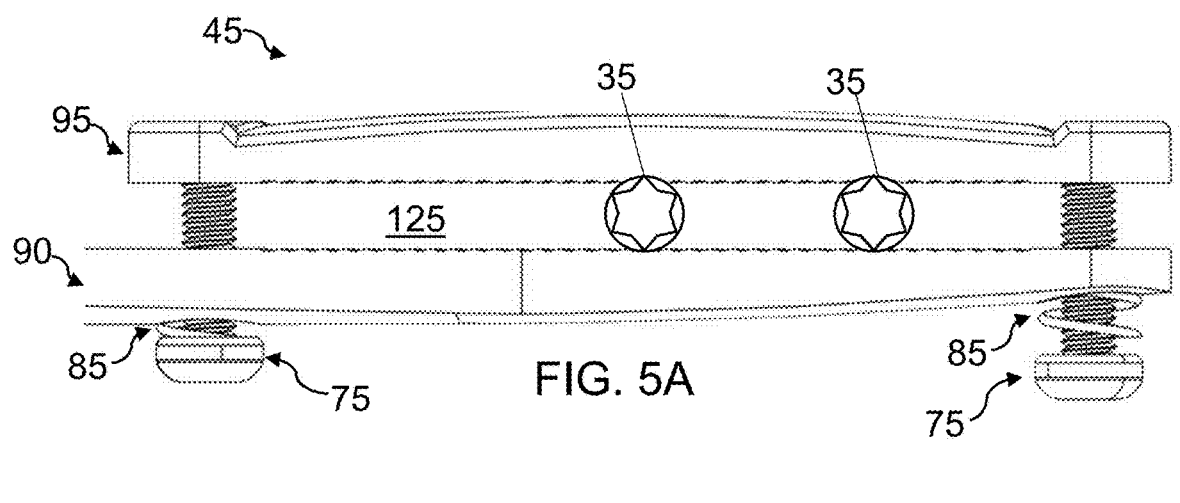
FIGS. 5A-5C depicts top views of one embodiment of the distal frame assembly and its relevant motions.
Figure 5B:
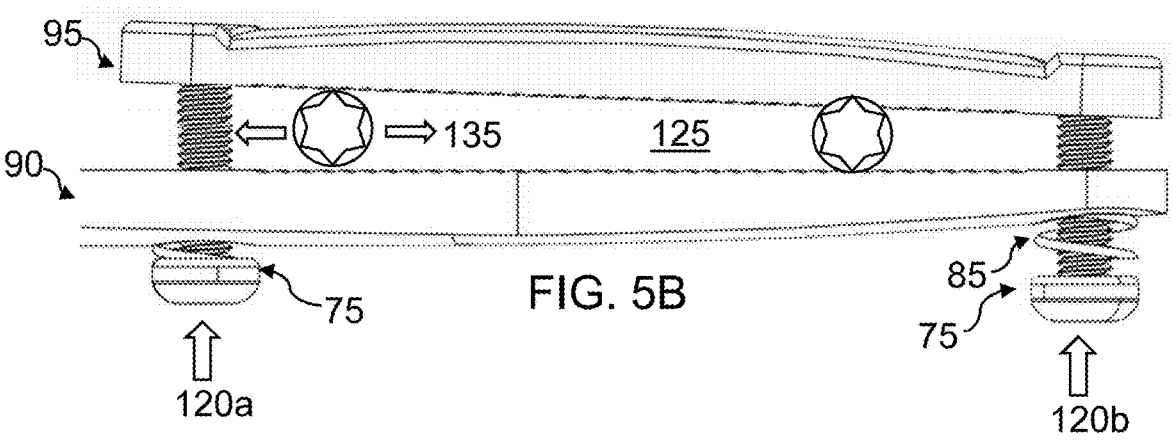

In another embodiment, the external fixator assemblies 30 comprises at least one quick release feature or mechanism 85 that allows the surgeon to adjust alignment, length, compression/distractions, and/or any other procedural requirements for each patient without removing or loosening the fasteners 75 as shown in FIGS. 5A-5B. As described herein, each of the proximal frame assembly 55 and the distal frame assembly 45 comprises a frame 60, 90, a compression bracket 65, 95, and at least one fastener 75. Each of the proximal frame assembly 55 and the distal frame assembly 45 further comprises one or more of at least one quick release mechanism 85, at least one fixation screw 35, at least one hex nut 100, and/or any combination thereof. The at least one quick release mechanism 85 may comprise a spring-loaded mechanism, a push-pull pin, a positive-locking pin, a ball-lock pin, push-button pin, detent pins, and/or any combination thereof. The spring-loaded mechanism comprises a compression spring.

In another embodiment, the proximal frame assembly 55 further comprises at least one fastener 75 that is used to couple the proximal compression bracket or proximal bracket 65 to the proximal frame 60. The proximal frame assembly 55 further comprises at least one quick release mechanism 85, the at least one quick release mechanism 85 is positioned to be concentrically aligned with the at least one fastener 75. The proximal frame assembly 55 further comprises at least one hex nut 100. The at least one hex nut 100 is concentrically aligned with the at least one fastener 75 and is used to secure the at least one fastener 75 to the proximal frame 60 and the proximal bracket 65.

In another embodiment, the proximal frame assembly 55 comprises a proximal frame 60 and a proximal compression bracket or a proximal bracket 65. The proximal frame assembly 55 further comprises at least two fasteners 75 that is used to couple the proximal compression bracket or proximal bracket 65 to the proximal frame 60. The proximal frame assembly 55 further comprises at least two quick release mechanisms 85, the at least two quick release mechanisms 85 is positioned to be concentrically aligned with the at least two fasteners 75. The proximal frame assembly 55 further comprises at least two hex nuts 100. Each of the at least two hex nuts 100 are concentrically aligned with the at least two fasteners 75 and is used to secure the at least two fasteners 85 to the proximal frame 60 and the proximal bracket 65.

In another embodiment, the external fixator assembly 30 comprises a distal frame assembly 45. The distal frame assembly 45 comprises a distal frame 90 and a distal compression bracket or a distal bracket 95. The distal frame assembly 45 further comprises at least one fastener 75 that is used to couple the distal compression bracket or distal bracket 95 to the distal frame 90. The distal frame assembly 45 further comprises at least one quick release mechanism 85, the at least one quick release mechanism 85 is positioned to be concentrically aligned with the at least one fastener 75. The distal frame assembly 45 further comprises at least one hex nut 100. The at least one hex nut 100 is concentrically aligned with the at least one fastener 75 and is used to secure the at least one fastener 75 to the distal frame 90 and the distal bracket 95.

In another embodiment, the distal frame assembly 45 comprises a distal frame 90 and a distal compression bracket or a distal bracket 95. The distal frame assembly 45 further comprises at least two fasteners 75 that are used to couple the distal compression bracket or distal bracket 95 to the distal frame 90. The distal frame assembly 45 further comprises at least two quick release mechanisms 85, the at least two quick release mechanisms 85 is positioned to be concentrically aligned with the at least two fasteners 75. The distal frame assembly 45 further comprises at least two hex nuts 100. The at least two hex nuts 100 are concentrically aligned with the at least two fasteners 75 and is used to secure the at least two fasteners 75 to the distal frame 90 and the distal bracket 95.

Figure 5C:
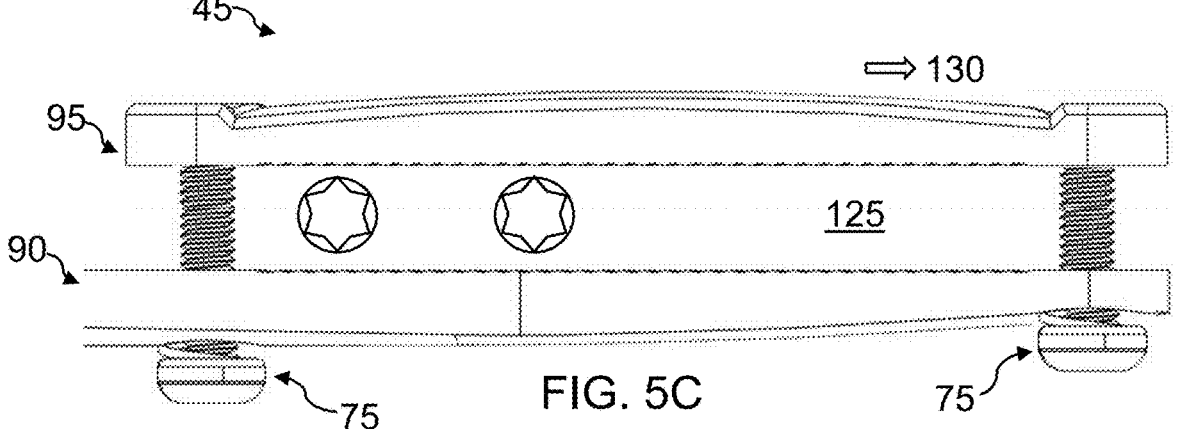
Figures 6A, 6B, 6C, 6D:
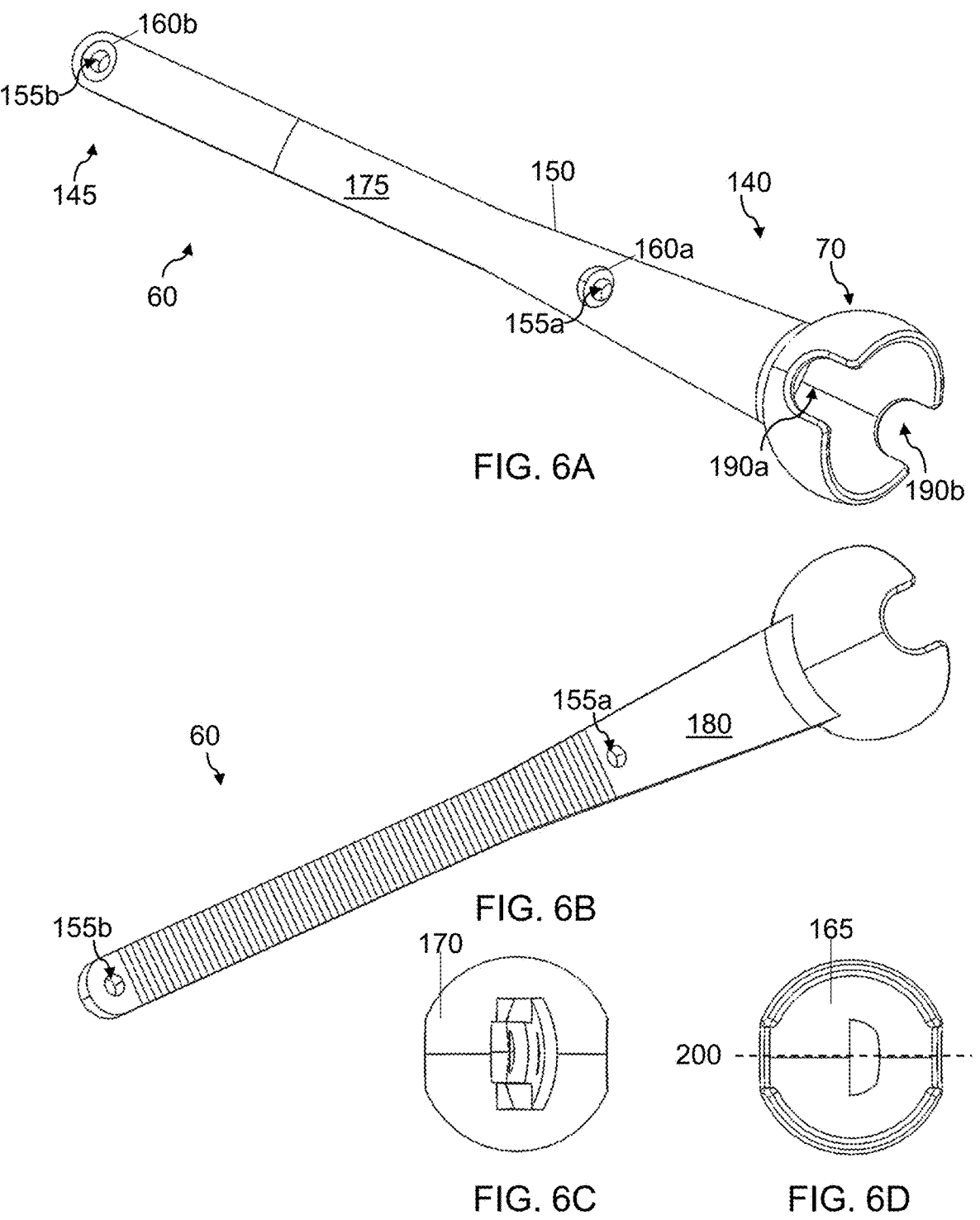
FIGS. 6A-6G depicts various plan views of one embodiment of a proximal frame.
Figures 6E, 6F, 6G:
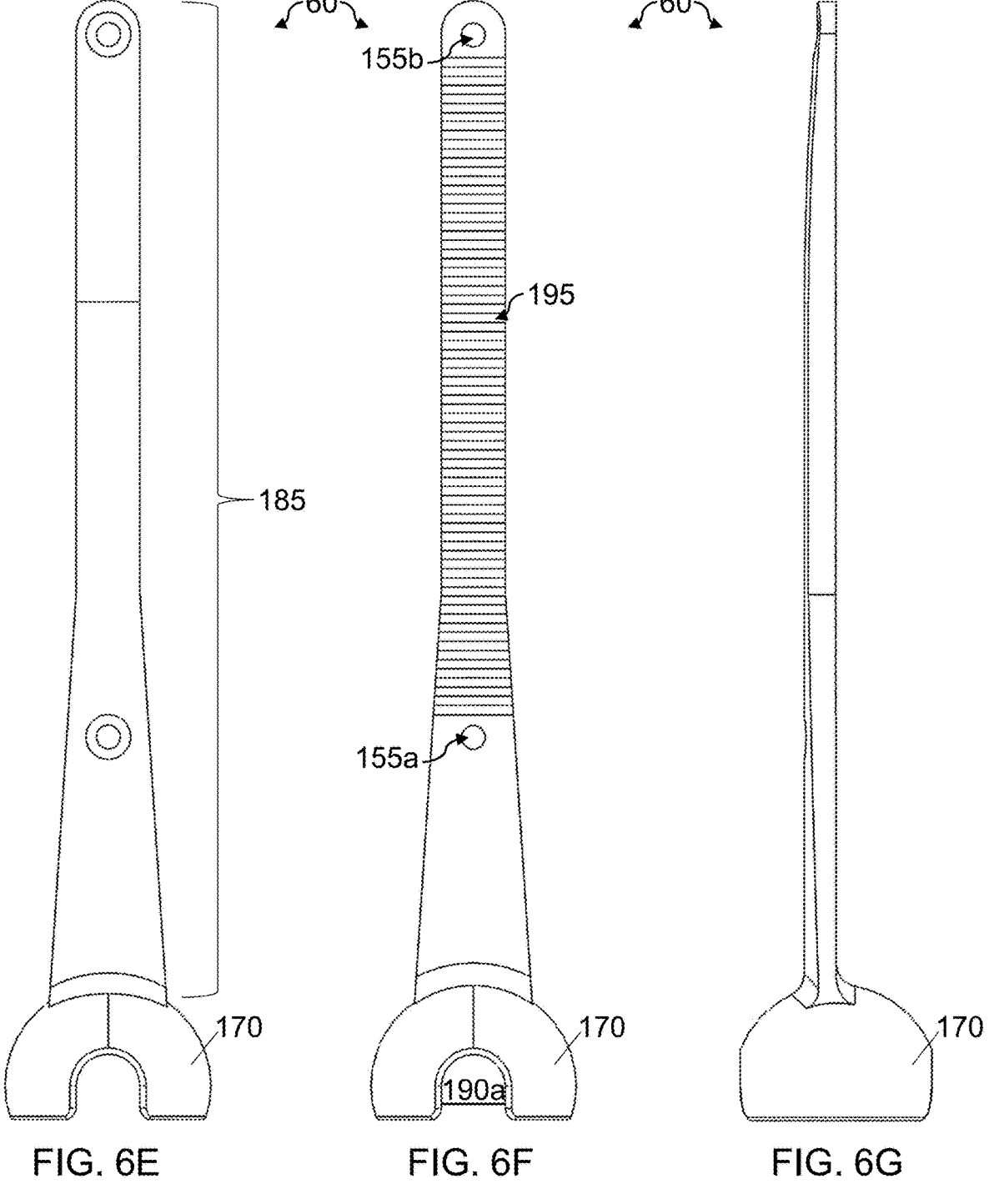

The compression bracket 65, 95 is secured to the frame 60, 90 with the at least one fastener 75. The compression bracket 65, 95 is spaced apart from the frame 60,90 to create an opening 125. The opening 125 is sized and configured to receive a portion of at least one fixation screw 35. Prior to tightening or securing, the opening 125 comprises an opening width that is equal to or larger than a diameter of a portion of the at least one fixation screw 35 to allow axial translation 135 of the at least one fixation screw 35 as shown in FIG. 5C. Once tightened, the opening width of the opening 125 is equal to and/or smaller than a portion of the diameter of the at least one fixation screw 35 to prevent any movement (e.g., axial, longitudinal or vertical) of the at least one fixation screw 35 as shown in FIG. 5A. Alternatively, at least one end may be compressed 120a, 120b to increase a portion of the opening width of the opening 125 resulting in a portion of the opening width of the opening 125 to be equal to or larger than the diameter of a portion of the at least one fixation screw 35 to allow axial translation 130 of the distal assembly 45 and/or the proximal assembly 55 relative to the at least one fixation screw 35 as shown in FIG. 5B.

More specifically, in preparation for tightening, the at least one quick release mechanism 85 is concentrically aligned with the at least one fastener 75. The at least one fastener 75 is disposed within the at least one quick release mechanism 85. The at least one fastener 75 and the at least one quick release mechanism 85 is inserted through frame 60, 90 and the compression bracket 65, 95 until the quick release mechanism 85 contacts a portion of the frame 60, 90. The at least one hex nut 100 is concentrically aligned with the at least two fasteners 85, and is positioned adjacent to the compression bracket 65, 95. The at least one hex nut 100 is used to secure the at least one fastener 85 to the frame 60, 90 and/or the compression bracket 65, 95, while squeezing, compressing or fixing the position of the at least one fixation screw 35. The at least one quick release mechanism 85 allows the surgeon to compress 120 a portion of the at least one fastener 75 until it contacts and engages the at least one quick release mechanism 85. The compression 120 of a portion of the at least one fastener 75 squeezes or compresses the quick release mechanism 85 while exerting an opposing force on the at least one hex nut 100 and making a portion of the frame 60,90 movable relative to the compression bracket 65, 95. Such movement increases a portion of the opening 125 to allow axial translation 135 of the at least one fixation screw and/or axial translation 130 of the proximal frame assembly 55 and/or the distal frame assembly. The at least one quick release mechanism 85 may comprise a spring-loaded mechanism, a push-pull pin, a positive-locking pin, a ball-lock pin, push-button pin, detent pins, and/or any combination thereof. The spring-loaded mechanism comprises a compression spring.

In another embodiment, the compression bracket 65, 95 is spaced apart from the frame 60,90 to create an opening 125 to accommodate at least two fixation screws 35. The opening 125 is sized and configured to receive a portion of at least two fixation screws 35 and/or a first fixation screw and a second fixation screw. Prior to tightening or securing, at least a portion of the opening 125 is equal to or larger than a diameter of at least one of the at least two fixation screws 35 and/or the first fixation screw or the second fixation screw to allow axial translation 135 of the at least one of the two fixation screws 35 and/or a first or second fixation screw 35 by distracting or compressing the relevant bones a shown in FIG. 5B (i.e., making one of the two fixation screws move relative to the remaining or fixed fixation screw). Alternatively, prior to tightening or securing, at least a portion of the opening 125 is equal to or larger than the diameter of the at least two fixation screws 35 and/or a first fixation screw and a second fixation screw to allow axial translation 130 of the distal assembly 45 and/or the proximal assembly 55 relative to the at least two fixation screws 35 and/or a first and second fixation screw as shown in FIG. 5C.

In another embodiment, in preparation for tightening, the at least two quick release mechanisms 85 are concentrically aligned with the at least two fasteners 75. The at least two fasteners 75 are disposed within the at least two quick release mechanisms 85. The at least two fasteners 75 and the at least two quick release mechanisms 85 are inserted through the frame 60, 90 and the compression bracket 65, 95 until the quick release mechanisms 85 contacts a portion of the frame 60, 90. The at least two hex nuts 100 are concentrically aligned with the at least two fasteners 85, and is positioned adjacent to the compression bracket 65, 95. The at least two hex nuts 100 is used to secure the at least two fastener 85 to the frame 60, 90 and/or the compression bracket 65, 95, while squeezing, compressing or fixing the position of the at least two fixation screws 35. The at least two quick release mechanism 85 allows the surgeon to compress 120 a portion of the at least one of the at least two fasteners 75 until it contacts and engages the at least one of the at least two quick release mechanisms 85. The compression 120 of the at least one of the two fasteners 75 squeezes or compresses at least one of the at least two quick release mechanisms 85 while exerting an opposing force on at least one of the at least two hex nuts 100 and making a portion of the frame 60,90 movable relative to the compression bracket

65, 95. Such movement increases a portion of the opening 125 to allow axial translation 135 of the at least one fixation screw relative to the second fixation screw. Also, such movement increases a portion of the opening to allow axial translation 130 of the proximal frame assembly 55 and/or the distal frame assembly relative to the at least two fixation screws 35.

The at least one and/or the at least two quick release mechanisms 85 on the proximal frame assembly 55 can have compression 120 independently or separately from the at least one and/or the at least two quick release mechanism on the distal frame assembly 45. Also, at least one of the at least two quick release mechanisms 85 on the proximal frame assembly 55 can include compression 120 independently or separately and/or at least one of the at least two quick release mechanisms 85 on the distal frame assembly 55 can operate independently or separately. Alternatively, the at least one and/or the at least two quick release mechanisms 85 on the proximal frame assembly 55 can include compression 120 dependently or together from the at least one and/or the at least two quick release mechanism on the distal frame assembly 45. Also, at least one of the at least two quick release mechanisms 85 on the proximal frame assembly 55 can include compression 120 dependently or together and/or at least one of the at least two quick release mechanisms 85 on the distal frame assembly 55 can operate dependently or together.

The at least one fixation screw 35 disposed within the distal frame assembly 45 can include axial translation 135 independently or separately from the at least one fixation screw 35 disposed within the proximal frame assembly 55. The at least two fixation screws 35 disposed within the distal frame assembly 45 can include axial translation 135 independently or separately from the at least two fixation screws 35 disposed within the proximal frame assembly 55. Also, at least one of the at least two fixation screws 35 disposed within the distal frame assembly 45 can include axial translation 135 independently or separately from the remaining fixation screw 35 (e.g., the second fixation screw). The least one of the at least two fixation screws 35 disposed within the proximal frame assembly 55 can include axial translation 135 independently or separately from the remaining fixation screw 35 (e.g., the second fixation screw). Alternatively, the first fixation screw disposed within the distal frame assembly 45 or the proximal frame assembly 55 can include axial translation 135 independently or separately from the second fixation screw 35 (e.g., the first fixation screw can include axial translation 135 relative to the second fixation screw).

Alternatively, the at least one fixation screw 35 disposed within the distal frame assembly 45 can include axial translation 135 dependently or together from the at least one fixation screw 35 disposed within the proximal frame assembly 55. The at least two fixation screws 35 disposed within the distal frame assembly 45 can include axial translation 135 dependently or together from the at least two fixation screws 35 disposed within the proximal frame assembly 55. Also, at least one of the at least two fixation screws 35 disposed within the distal frame assembly 45 can include axial translation 135 dependently or together from the remaining fixation screw 35 (e.g., the second fixation screw). The least one of the at least two fixation screws 35 disposed within the proximal frame assembly 55 can include axial translation 135 dependently or together from the remaining fixation screw 35 (e.g., the second fixation screw). Alternatively, the first fixation screw disposed within the distal frame assembly 45 or the proximal frame assembly 55 can include axial translation 135 dependently or together from the second fixation screw 35 (e.g., the first fixation screw can include axial translation 135 relative to the second fixation screw).

FIGS. 6A-6G depict various plan views of one embodiment of a proximal frame 60. In another embodiment, the proximal frame assembly 55 comprises a proximal frame 60 and a proximal compression bracket or a proximal bracket 65. The proximal frame 60 comprises an elongated arm 150 and the socket component 70. The elongated arm 150 includes a first end 140 and a second end 145. The proximal frame 60 comprises a first end 140 and a second end 145. The socket component 70 disposed at a first end 140 and/or a second end 145. The elongated arm 150 and/or the proximal frame 60 further comprises a first surface 175 and a second surface 180. The elongated arm 150 and/or the proximal frame 60 further comprises at least one opening 155a, 155b and/or it comprises at least two openings 155a, 155b. The at least one opening 155a, 155b and/or the at least two openings 155a, 155b extends through the first surface 175 and the second surface 180. The at least one opening 155a, 155b and/or the at least two openings 155a, 155b are sized and configured to receive a portion of one or more fasteners 75.

The proximal frame 60 and/or the proximal arm 150 further includes at least one counterbore 160a, 160b and/or at least two counterbores 160a, 160b. The at least one counterbore 160, 160b is concentrically aligned with the at least one opening 155a, 155b. Alternatively, the at least two counterbores 160a, 160b are concentrically aligned with each of the at least two openings 155a, 155b. The at least one counterbore 160a, 160b and/or at least two counterbores 160a, 160b comprises a larger diameter than a diameter of the opening 155a, 155b. The at least one counterbore 160a, 160b and/or at least two counterbores 160a, 160b is sized and configured to receive one or more quick release mechanisms 85. The at least one counterbore 160a, 160b and/or at least two counterbores 160a, 160b is sized and configured to receive a head of one or more of the fasteners 75. The at least one counterbore 160a, 160b and/or at least two counterbores 160a, 160b is sized and configured to receive a head of one or more of the fasteners 75 and one or more quick release mechanisms 85. The at least one counterbore 160a, 160b and/or the at least two counterbores 160a, 160b extend from a first surface 180 towards a portion of the second surface 180.

At least one of the surfaces 175, 180 of the proximal arm 150 and/or proximal frame 60 may comprise surface finish (not shown) or protrusions 195. The protrusions 195 may comprise threads, flutes, grooves, and/or teeth that may include various shapes. The various shapes may include tapered, stepped, conical and/or paralleled, flat, pointed, and/or rounded. The surface finishes may further comprise roughened surfaces or porous surfaces, including turned, blasting, sand blasting, acid etching, chemical etching, dual acid etched, plasma sprayed, anodized surfaces, and/or any combination thereof. The surface finishes may further include a polish surface finish or texture. Alternatively, at least a portion of one of the surfaces 175, 180 of the proximal arm 150 and/or the proximal frame 60 may comprise a surface finish or protrusions 195. In another embodiment, at least a portion of the first surface 175 or a portion of the second surface 180 comprises a surface finish or protrusions. Accordingly, at least a portion of the first surface 175 and a portion of the second surface 180 comprises a surface finish or protrusions.

The proximal arm 150 and/or the proximal frame 60 comprises a shape and a proximal length 185. The shape may be uniform or non-uniform. Accordingly, at least a portion of the shape may be uniform or non-uniform. The shape may include an elongated rectangle. The shape at a first end 140 or the second end 145 may include a taper. The shape at the first end 140 or the second end 145 may include a substantially rectangular shape and tapered at the opposing end.

The socket component 70 is disposed at a first end 140 and/or a second end 145. The socket component 70 is disposed at a first end 140. The socket component 70 is disposed at a second end 145. The socket component 70 extends outwardly from the first end 140 of the proximal arm 150 and/or proximal frame 60. The socket component 70 comprises an outer surface 170, and inner surface 165, and one or more notches 190a, 190b. The inner surface 165 of the socket component 70 contacts and engages with the outer surface 245 of the ball component 105. The one or more notches 190a, 190b extends through the socket component 70. Alternatively, the socket component 70 comprises a first notch 190a and a second notch 190b. The first notch 190a is spaced apart from the second notch 190b. The first notch 190a is aligned with the second notch 190b along the horizontal or axial axis 200. The first notch 190a is directly opposite of the second notch 190. The one or more notches 190a, 190b, the first notch 190a, and/or the second notch 190a aligns with the at least one fastener opening 110 of the ball component 105. The one or more notches 190a, 190b, the first notch 190a, and/or the second notch 190a substantially aligns with the at least one fastener opening 110 of the ball component 105.

The socket component 70 further comprises a shape. The shape may be a hemisphere. The shape may be a hollow hemisphere. The shape may further include a concave or arch shape. Furthermore, at least a portion of one of the surfaces 165, 170 may comprise a surface finish (not shown) or protrusions (not shown). The protrusions may comprise threads, flutes, grooves, and/or teeth that may include various shapes. The various shapes may include tapered, stepped, conical and/or paralleled, flat, pointed, and/or rounded. The surface finishes may further comprise roughened surfaces or porous surfaces, including turned, blasting, sand blasting, acid etching, chemical etching, dual acid etched, plasma sprayed, anodized surfaces, and/or any combination thereof. The surface finishes may further include a polish surface finish or texture.

FIGS. 7A-7G depict various plan views of one embodiment of a distal frame 90. In another embodiment, the distal frame assembly 45 comprises a distal frame 90 and a distal compression bracket or a distal bracket 95. The distal frame 90 comprises an elongated distal arm 215 and the ball component 105. The elongated distal arm 215 includes a first end 205 and a second end 210. The distal frame 90 comprises a first end 205 and a second end 210. The ball component 105 disposed at a first end 205 and/or a second end 210. The elongated arm 215 and/or the distal frame 90 further comprises a first surface 230 and a second surface 235. The elongated arm 215 and/or the distal frame 90 further comprises at least one opening 220a, 220b and/or it comprises at least two openings 220a, 220b. The at least one opening 220a, 220b and/or the at least two openings 220a, 220b extends through the first surface 230 and the second surface 235. The at least one opening 220a, 220b and/or the at least two openings 220a, 220b are sized and configured to receive a portion of one or more fasteners 75.

The at least one opening 220a, 220b and/or the at least two openings 220a, 220b further includes at least one counterbore 225a, 225b and/or at least two counterbores 225a, 225b. The at least one counterbore 225a, 225b is concentrically aligned with the at least one opening 225a, 225b. Alternatively, the at least two counterbores 225a, 225b are concentrically aligned with each of the at least two openings 220a, 220b. The at least one counterbore 225a, 225b and/or at least two counterbores 225a, 225b comprises a larger diameter than a diameter of the opening 220a, 220b. The at least one counterbore 225a, 225b and/or at least two counterbores 225a, 225b is sized and configured to receive one or more quick release mechanisms 85. The at least one counterbore 225a, 225b and/or at least two counterbores 225a, 225b is sized and configured to receive a head of one or more of the fasteners 75. The at least one counterbore 225a, 225b and/or at least two counterbores 225a, 225b is sized and configured to receive a head of one or more of the fasteners 75 and one or more quick release mechanisms 85. The at least one counterbore 225a, 225b and/or the at least two counterbores 225a, 225b extend from a first surface 230 towards a portion of the second surface 235.

At least one of the surfaces 230, 235 of the distal arm 215 and/or distal frame 90 may comprise surface finish (not shown) or protrusions 240. The protrusions 240 may comprise threads, flutes, grooves, and/or teeth that may include various shapes. The various shapes may include tapered, stepped, conical and/or paralleled, flat, pointed, and/or rounded. The surface finishes may further comprise roughened surfaces or porous surfaces, including turned, blasting, sand blasting, acid etching, chemical etching, dual acid etched, plasma sprayed, anodized surfaces, and/or any combination thereof. The surface finishes may further include a polish surface finish or texture. Alternatively, at least a portion of one of the surfaces 230, 235 of the distal arm 215 and/or the distal frame 90 may comprise a surface finish or protrusions 240. In another embodiment, at least a portion of the first surface 230 or a portion of the second surface 235 comprises a surface finish or protrusions 240. Accordingly, at least a portion of the first surface 230 and a portion of the second surface 235 comprises a surface finish or protrusions 240. At least a portion of the first surface 230 and a portion of the second surface 235 may be a flat surface or may be a curved surface.

The distal arm 215 and/or the distal frame 90 comprises a shape and a distal length 225. The shape may be uniform or non-uniform. Accordingly, at least a portion of the shape may be uniform or non-uniform. The shape may include an elongated rectangle and/or a hemispherical shape. The shape at a first end 205 and/or the second end 210 may include a taper. The shape at the first end 205 or the second end 210 may include a substantially rectangular shape and tapered at the opposing end. The length 185 of the proximal arm 150 and/or the proximal frame 60 is longer or larger than the length 255 of the distal arm 215 and/or the distal frame 90. The distal arm 215 and/or the distal frame 90 may be solid or hollow.

The ball component 105 is disposed at a first end 205 and/or a second end 210. The ball component 105 is disposed at a first end 205. The ball component 105 is disposed at a second end 210. The ball component 105 extends outwardly from the first end 205 of the distal arm 215 and/or distal frame 90. The ball component 105 comprises an outer surface 245, and inner surface 270, one or more fastener openings 110, and/or a channel 250. The outer surface 245 of the ball component 105 contacts and engages with the inner surface 165 of the socket component 70. The one or more fastener openings 110 extends through the ball component 105. The one or more fastener openings 110 is positioned substantially perpendicular or perpendicular to the longitudinal axis 260 of the distal arm 215 and/or the distal frame 90. The one or more fastener openings 110 is positioned parallel or substantially parallel to the horizontal axis 265 of the distal arm 215 and/or the distal frame 90.

Figures 7A, 7B, 7C, 7D:
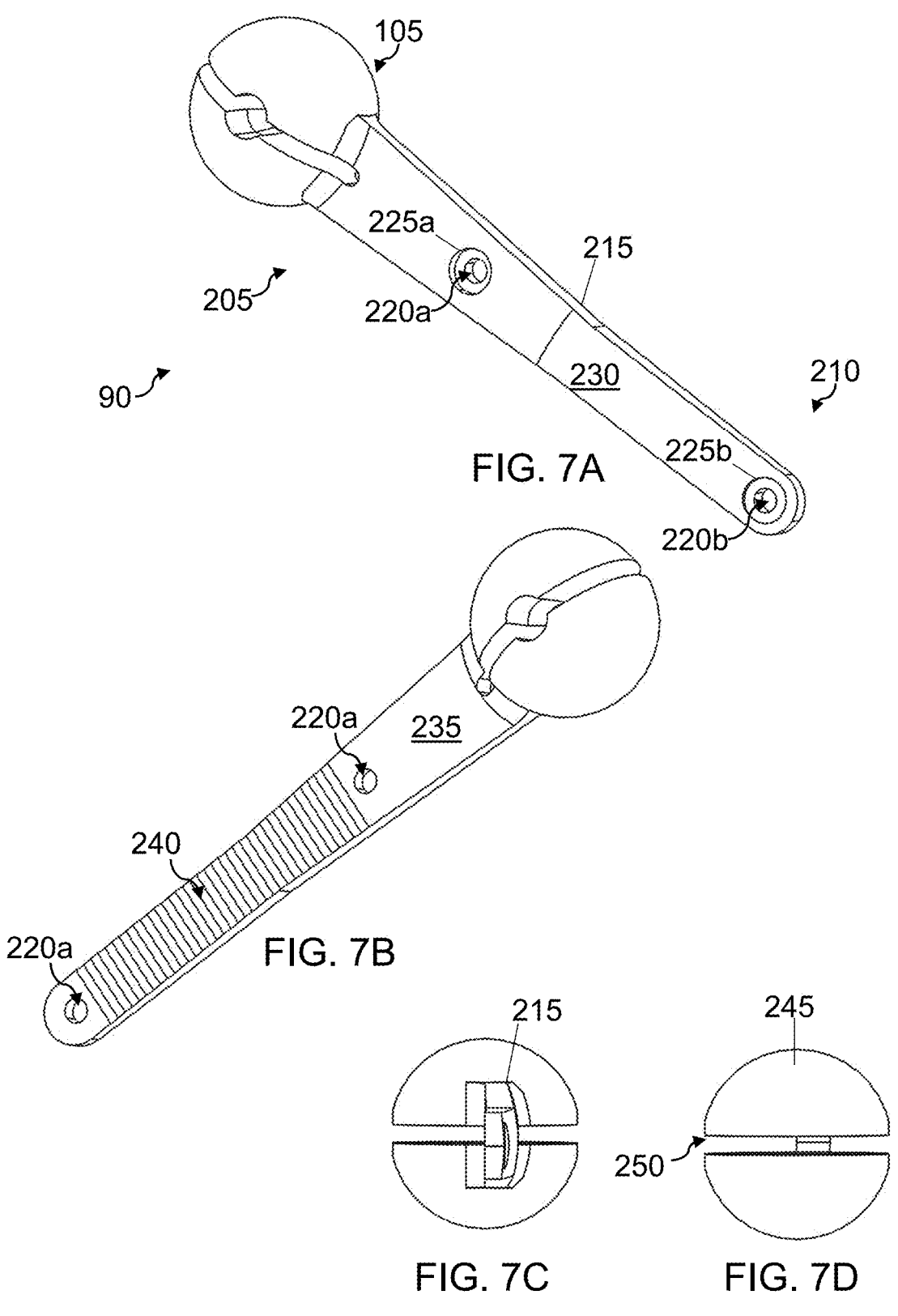
FIGS. 7A-7G depicts various plan views of one embodiment of a distal frame.
Figures 7E, 7F, 7G, 7H:
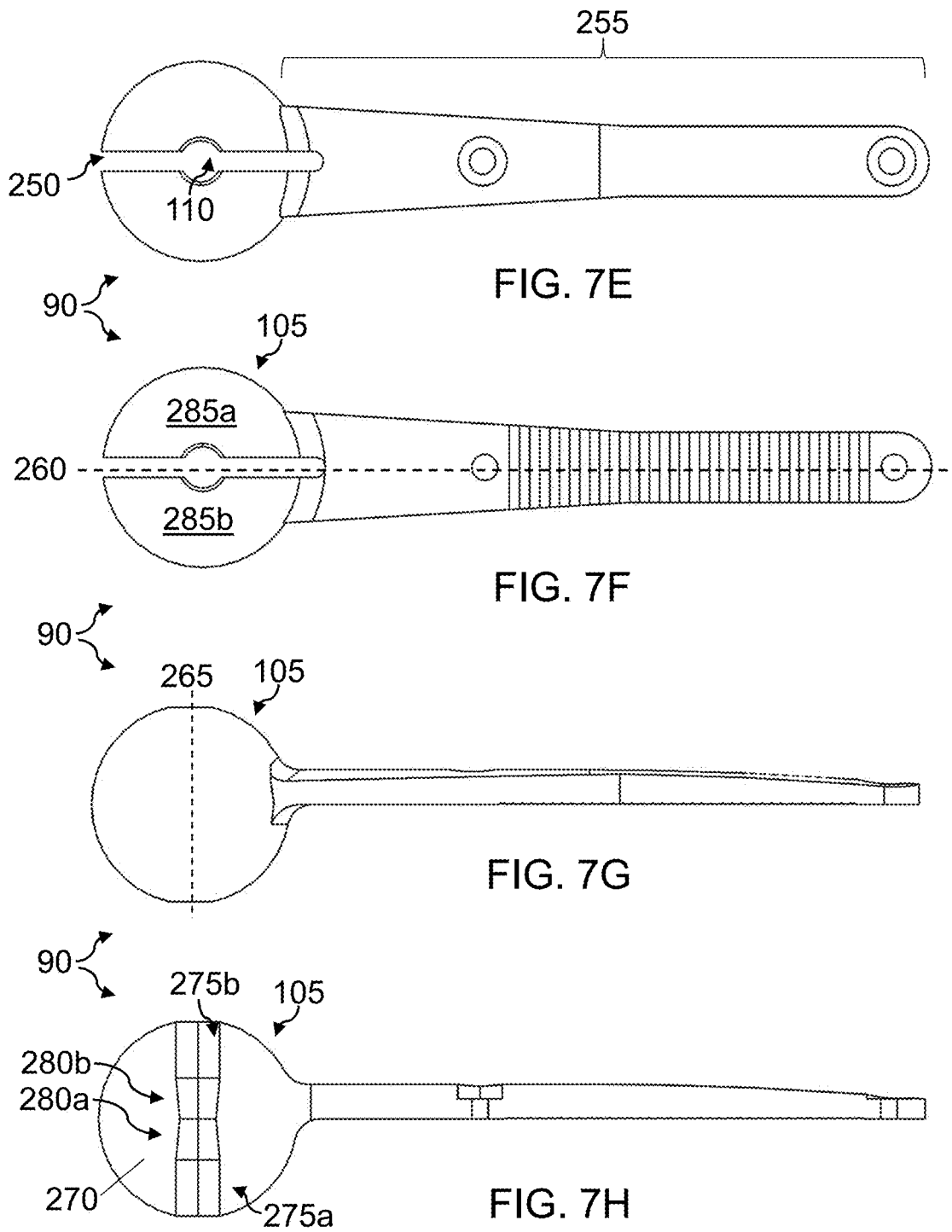
FIG. 7H depicts a cross-sectional view of the distal frame of FIG. 7F.
Figures 8A, 8B, 8C:
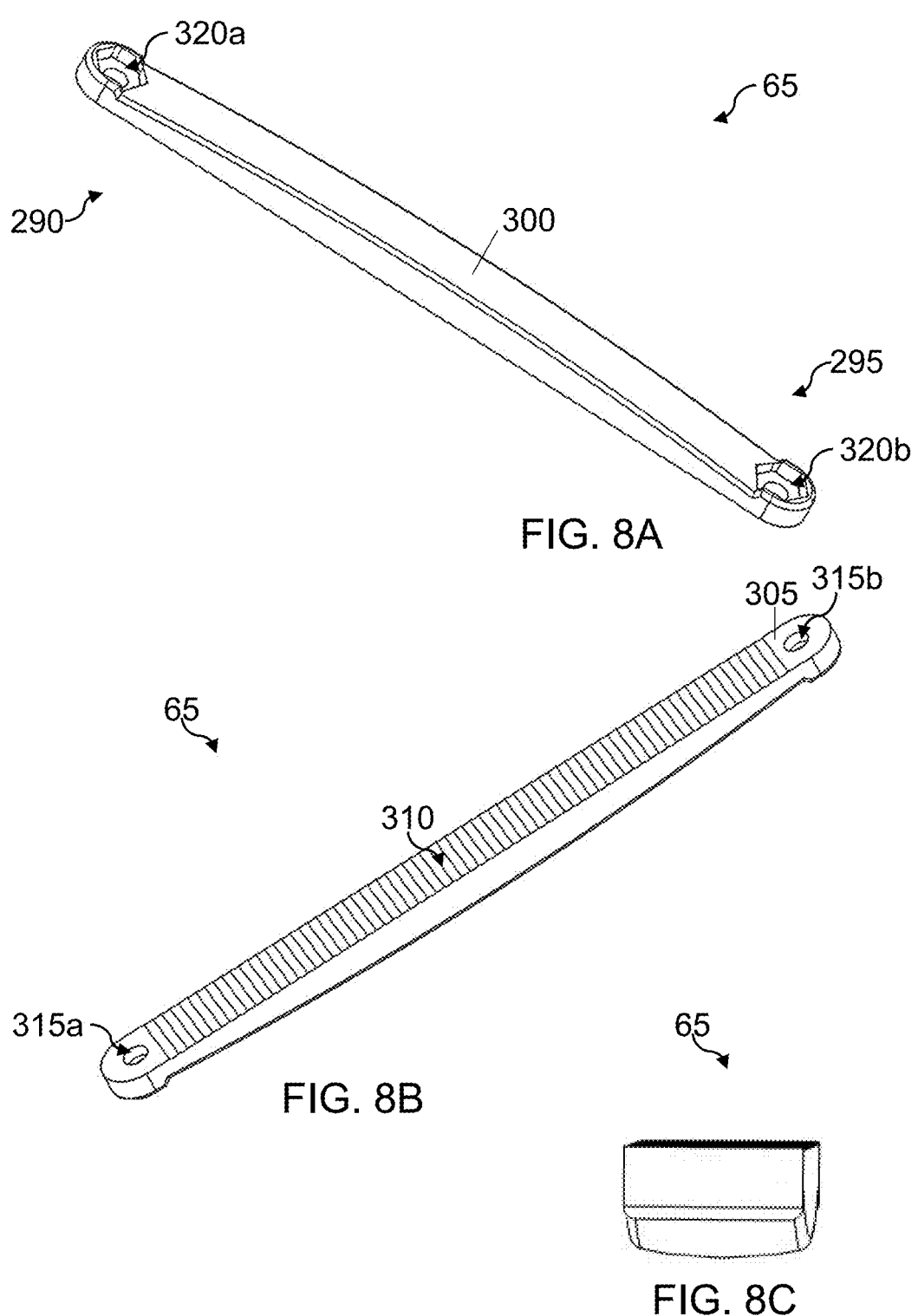
FIGS. 8A-8F depicts various plan views of one embodiment of a proximal compression bracket.
Figures 8D, 8E, 8F, 8G:
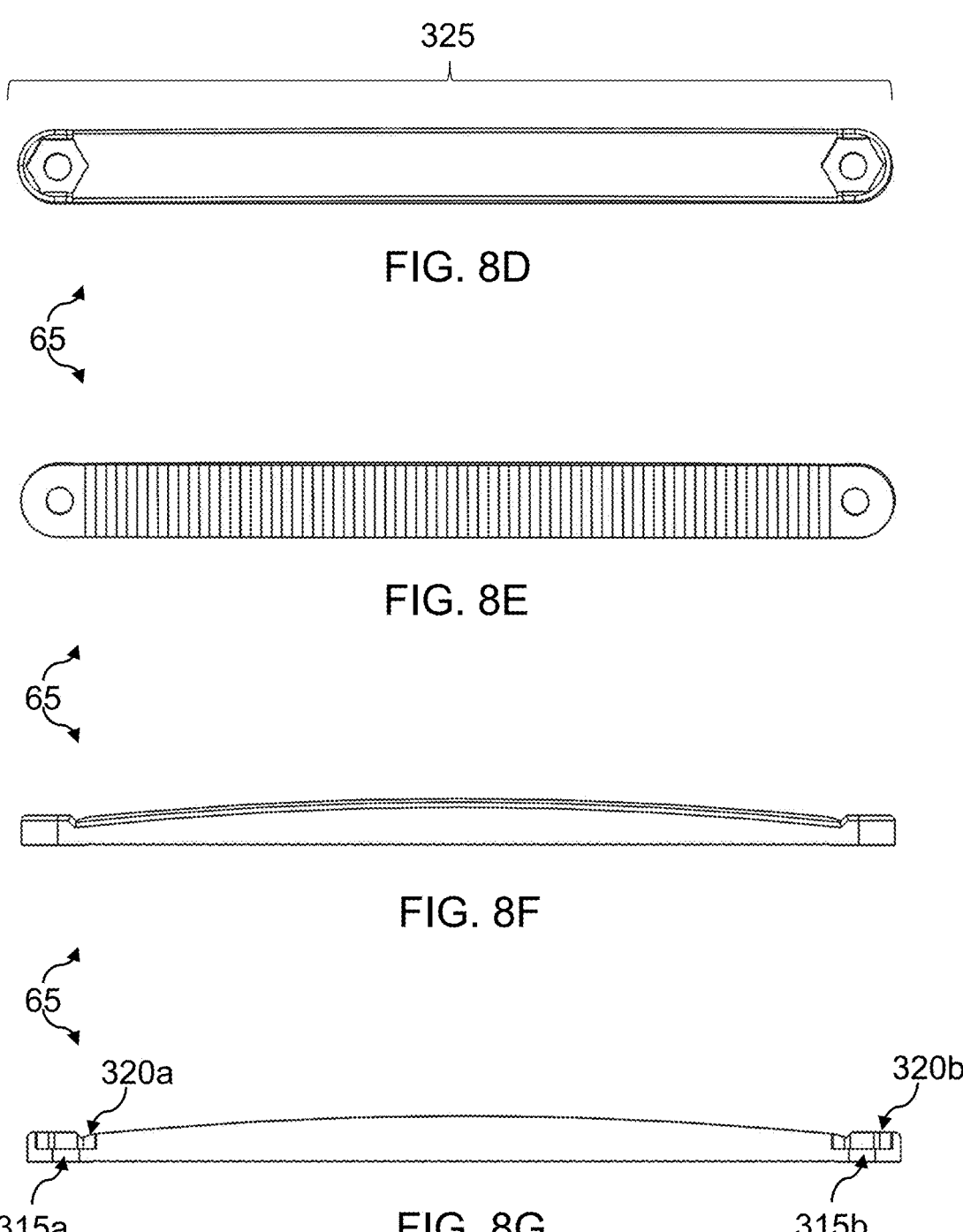
FIG. 8G depicts a cross-sectional view of the proximal compression bracket of FIG. 8F.
Figure 9A:
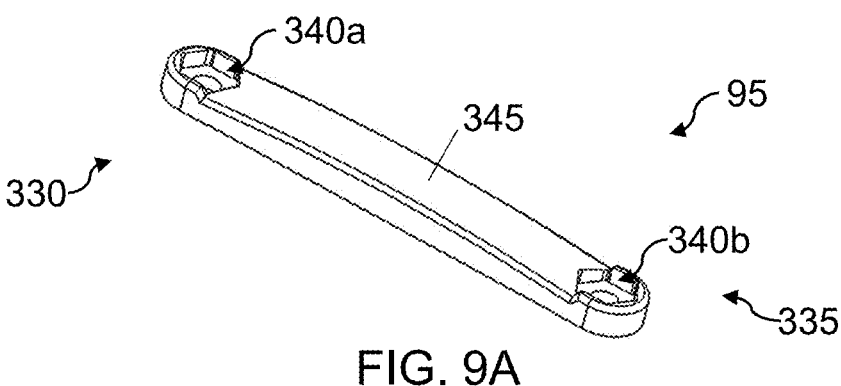
FIGS. 9A-9F depicts various plan views of one embodiment of a distal compression bracket.
Figure 9B:
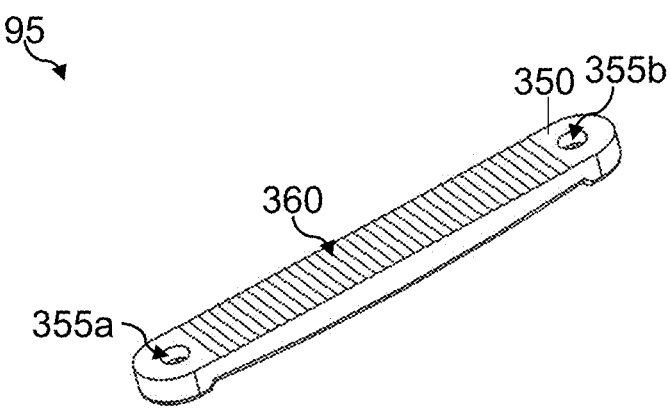
Figure 9C:
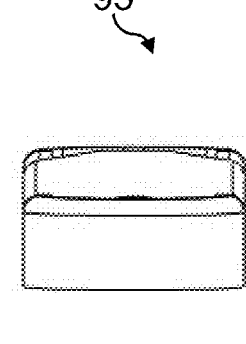
Figure 9D:
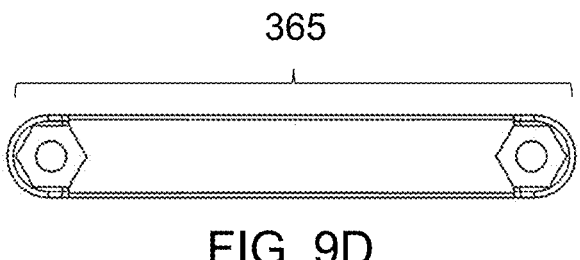
Figure 9E:
Figure 9E:
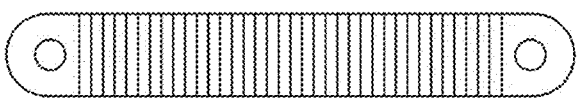
Figure 9F:
Figure 9F:
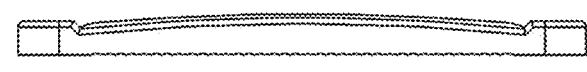
Figure 9G:
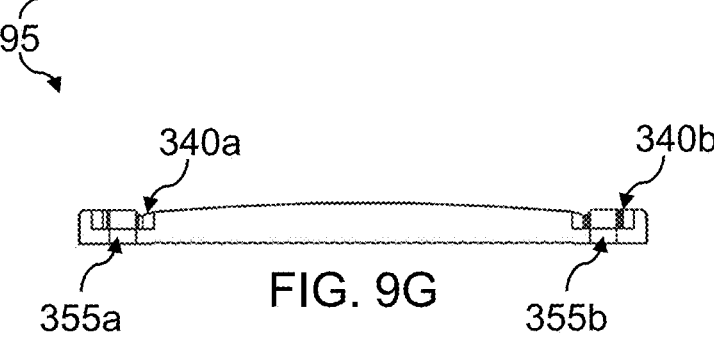
FIG. 9G depicts a cross-sectional view of the distal compression bracket of FIG. 9F.

The one or more fastener openings 110 comprises a first portion 275a, 275b and a second portion 280a, 280b as shown in the cross-sectional view of FIG. 7H. The first portion 275a, 275b of the one or more fastener openings 110 is sized and configured to receive a one or more locking fasteners 80a, 80b. The first portion 275a is spaced apart from the first portion 275b. The first portion 275a is diametrically opposed to the first portion 275b. The first portion 275a, 275b may further comprise threads. The first portion 275a, 275 may comprise a uniform shape. Alternatively, the second portion 280a, 280b comprises a non-uniform shape, the non-uniform shape includes a taper or frustum shape. The second portion 280a is diametrically opposed to the second portion 280b. The second portion 280a, 280b may further comprise threads.

In one embodiment, a first locking fastener 80a is disposed within a first side of the one or more openings 110. The first locking fastener 80a will enter the first portion 270a of the one or more openings 110 by using a driver 20 with little to no resistance. As the surgeon continues to drive the first locking fastener 80a into the second portion 280a of the one or more openings 110, at least a portion of the ball component 105 outer diameter will expand to contact the inner surface 165 of the socket component 70 to restrict or eliminate any polyaxial motion. Alternatively, a second locking fastener 80b is disposed within a second side of the one or more openings 110. The second locking fastener 80b will enter the first portion 270b of the one or more openings 110 by using a driver 20 with little to no resistance. As the surgeon continues to drive the second locking fastener 80b into the second portion 280b of the one or more openings 110, at least a portion of the ball component 105 outer diameter will expand to contact the inner surface 165 of the socket component 70 to restrict or eliminate any polyaxial motion. Accordingly, a first locking fastener 80a is disposed on first side of the one or more openings 110 and a second locking fastener 80b is disposed on a second side of the one or more openings. The first locking fastener 80a would enter the first portion 270b and the second locking fastener 80b will enter the first portion 270b of the one or more openings 110 by using a driver 20 with little to no resistance. As the surgeon continues to drive the first locking fastener 80a into the second portion 280a and the second locking fastener 80b into the second portion 280b of the one or more openings 110, the entire ball component 105 outer diameter will expand to contact the inner surface 165 of the socket component 70 to restrict or eliminate any polyaxial motion.

Alternatively, the ball component 105 comprises a channel 250. The channel 250 is aligned along the longitudinal axis 260 of the distal frame 90 and/or the distal arm 215. The channel 250 extends partially through the ball component 105. The channel 250 is substantially perpendicular or perpendicular to the one or more openings 110 and/or the horizontal axis 265 of the distal frame 90 and/or the distal arm 215. The channel 250 is disposed in the center of the ball component 105 and splits the ball component into a first portion 285a and a second portion 285b. The channel 250 allows the first portion 285a of the ball component 105 and the second portion 285b of the ball component to move relative to each other when the one or more locking fasteners 80a, 80b are disposed, inserted and/or engages with the one or more openings 110 of the ball component 105.

Accordingly, the channel 250 allows the first portion 285a of the ball component 105 and the second portion 285b of the ball component to move relative to each other away from the longitudinal axis 260 when the one or more locking fasteners 80a, 80b are disposed, inserted and/or engages with the one or more openings 110 of the ball component 105. The moving away or change in position allows the ball component 105, a first portion 285a and/or a second portion 285b of the ball component to expand and the outer surface 245 of the ball component 105 contacts and engages the inner surface 165 of the socket component 70 to cause an increase in friction and restrict polyaxial movement. Alternatively, the first portion 285a of the ball component 105 and/or the second portion 285b of the ball component 105 moves from unlocked position to a locked position, by having the first portion 285a and/or second portion 285b move away from the longitudinal axis 260 when the at least one locking fastener 80a, 80b is inserted into the one or more openings 110 to expand the outer diameter of the ball component 105 and engage the inner surface 165 of the socket component 70 to increase the friction and restrict polyaxial movement. The first portion 285b may move independent of the second portion 285b.

FIGS. 8A-8G, 9A-9G, 19, 24A-24H, 31A-31B and 32 depict various plan views of a proximal compression bracket 65 and different embodiments of a distal compression bracket 95,660,1165. In another embodiment, the distal frame assembly 45,605,1160 comprises a distal frame 90,655,1175 and a distal compression bracket or a distal bracket 95,660,1165 and the proximal frame assembly 55,610,1145 comprises a proximal frame 60,640,1210. The proximal frame assembly 55,610,1145 further comprises a proximal compression bracket 65. Each of the distal brackets 95,660,1165 and/or the proximal brackets 65 includes a first end 290,330,845, a second end 295,335,850 and a length 325,365,870,1285. Each of the distal brackets 95,660, 1165 and/or the proximal bracket 65 further comprises a first surface 300, 345,865,1290 and a second surface 305,350, 860,1295. Each of the proximal bracket 65 and/or the distal brackets 95,660,1165 further comprises at least one opening 315a,315b,355a,355b, 840a,840b,1200a,1200b and/or it comprises at least two openings 315a, 315b, 355a, 355b, 840a,840b,1200a,1200b disposed at a first end 290,330,845 and/or a second end 295,335,850. The at least one opening and/or the at least two openings 315a,315b,355a,355b,840a, 840b, 1200a,1200b extends through the first surface 300, 345,865,1290 and the second surface 305, 350,860,1295. The at least one opening 315a,315b,355a,355b,840a,840b, 1200a,1200b are sized and configured to receive a portion of one or more fasteners 75, 620,1170. The length 325 of the proximal bracket 65 is longer than the length 365,870,1285 of the distal bracket 95,660,1165.

The at least one opening and/or the at least two openings 315a, 315b, 355a, 355b, 840a,840b,1200a,1200b further includes at least one counterbore 320a, 320b, 340a, 340b, and/or at least two counterbores 320a, 320b, 340a, 340b. The at least one counterbore 320a, 320b, 340a, 340b is concentrically aligned with the at least one opening 315a, 315b, 355a, 355b. Alternatively, the at least two counterbores 320a, 320b, 340a, 340b are concentrically aligned with each of the at least two openings 315a, 315b, 355a, 355b, 840a, 840b,1200a,1200b. The at least one counterbore 320a, 320b, 340a, 340b and/or at least two counterbores 320a, 320b, 340a, 340b comprises a larger diameter than a diameter of the opening 315a,315b,355a,355b,840a,840b, 1200a,1200b. The at least one counterbore 320a, 320b, 340a, 340b and/or at least two counterbores 320a, 320b, 340a, 340b is sized and configured to receive one or more hex nuts 100 and/or a washer. The at least one counterbore 320a, 320b, 340a, 340b and/or the at least two counterbores 320a, 320b, 340a, 340b extend from a first surface 300,345, 865,1290 towards a portion of the second surface 305,350, 860, 1295.

At least one of the surfaces 300,305,345,350,860,865, 1290,1295 of the distal bracket 95,660,1165 and/or proximal bracket 65 may comprise surface finish (not shown) or protrusions 310,360,855,1195. The protrusions 310,360, 855,1195 may comprise threads, flutes, grooves, and/or teeth that may include various shapes. The various shapes may include tapered, stepped, conical and/or paralleled, flat, pointed, and/or rounded. The surface finishes may further comprise roughened surfaces or porous surfaces, including turned, blasting, sand blasting, acid etching, chemical etching, dual acid etched, plasma sprayed, anodized surfaces, and/or any combination thereof. The surface finishes may further include a polish surface finish or texture. Alternatively, at least a portion of one of the surfaces 300,305,345, 350,300,305,345, 350,860,865,1290,1295 of the distal bracket 95,660,1165 and/or proximal bracket 65 may comprise a surface finish or protrusions 310,360,855,1195. In another embodiment, at least a portion of the first surface 300,345,865,1290 or a portion of the second surface 305, 350,860, 1290 comprises a surface finish or protrusions 310,360,855,1195. Accordingly, at least a portion of the first surface 300,345,865,1290 and a portion of the second surface 305,350,860, 1290 comprises a surface finish or protrusions 310,360,855,1195. The protrusions 310,360, 855, 1195 contact at least a portion of the fixation screws 35, 595,1075 to prevent migration and/or contacts at least a portion of an outer diameter 540 of the fixation screws 35,595,1075 to prevent migration.

Figures 10A, 10B, 10C:
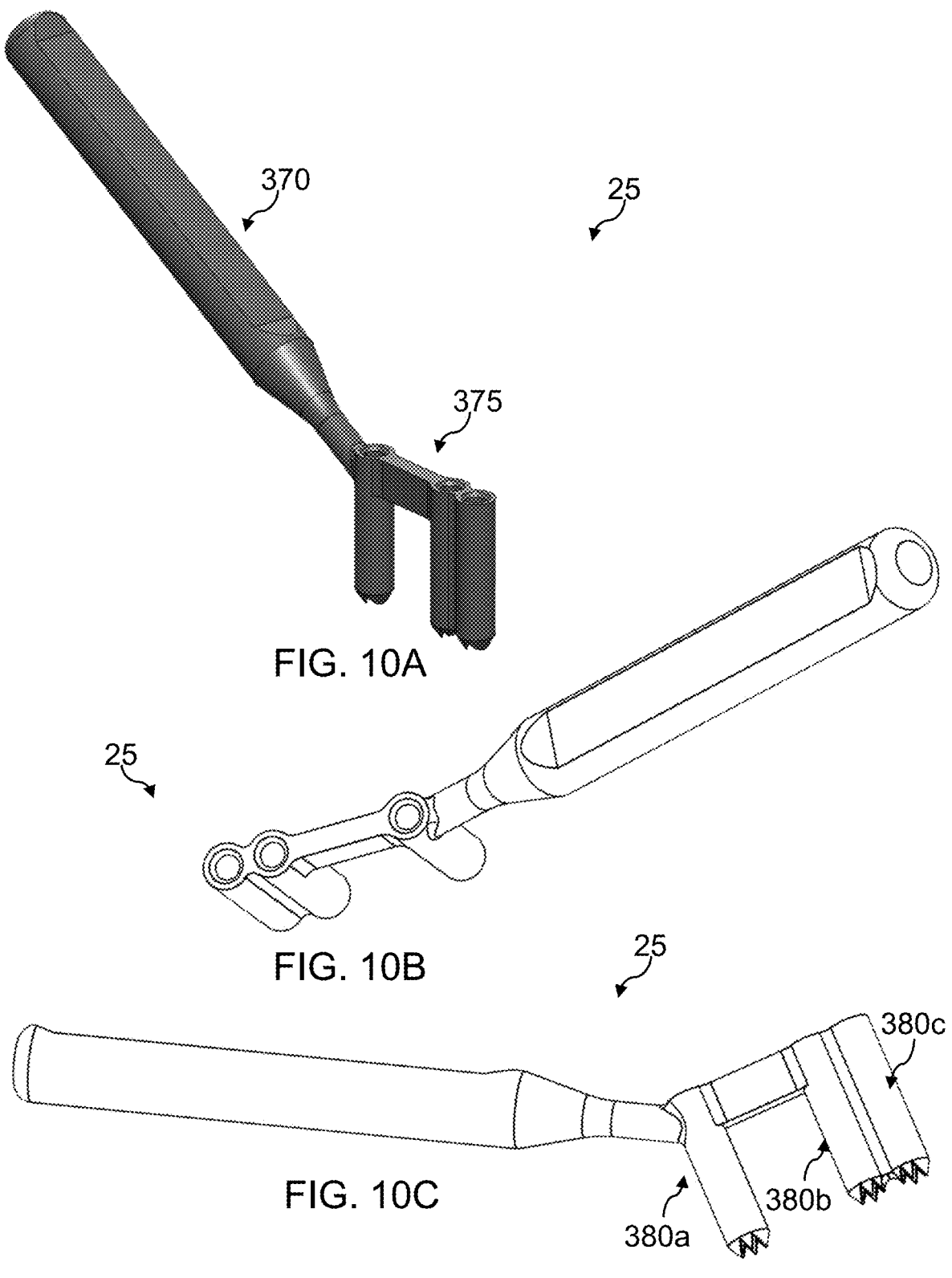
FIGS. 10A-10F depict various plan views of one embodiment of a guide tool.
Figures 10D, 10E:
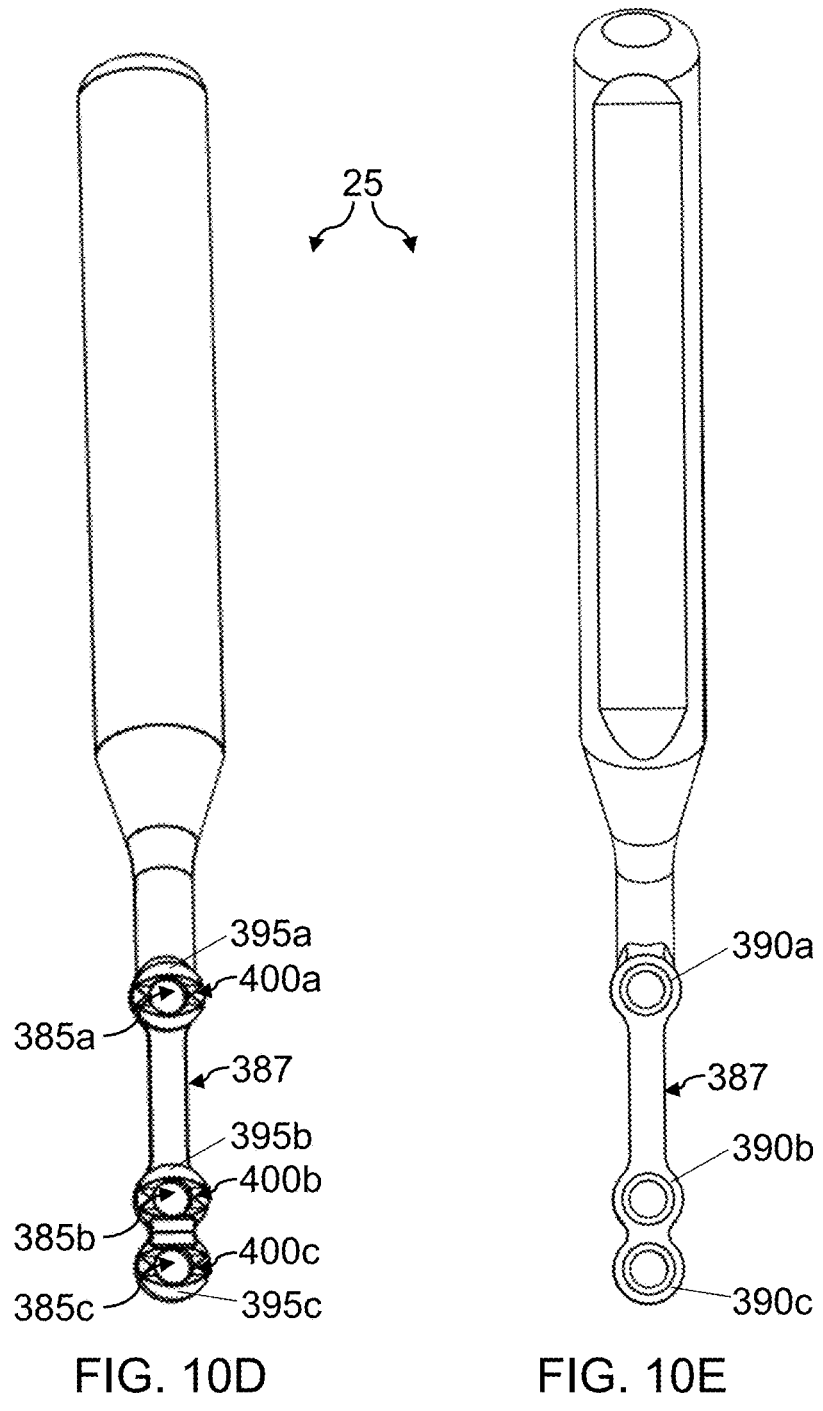
Figures 10F, 10G, 10H:
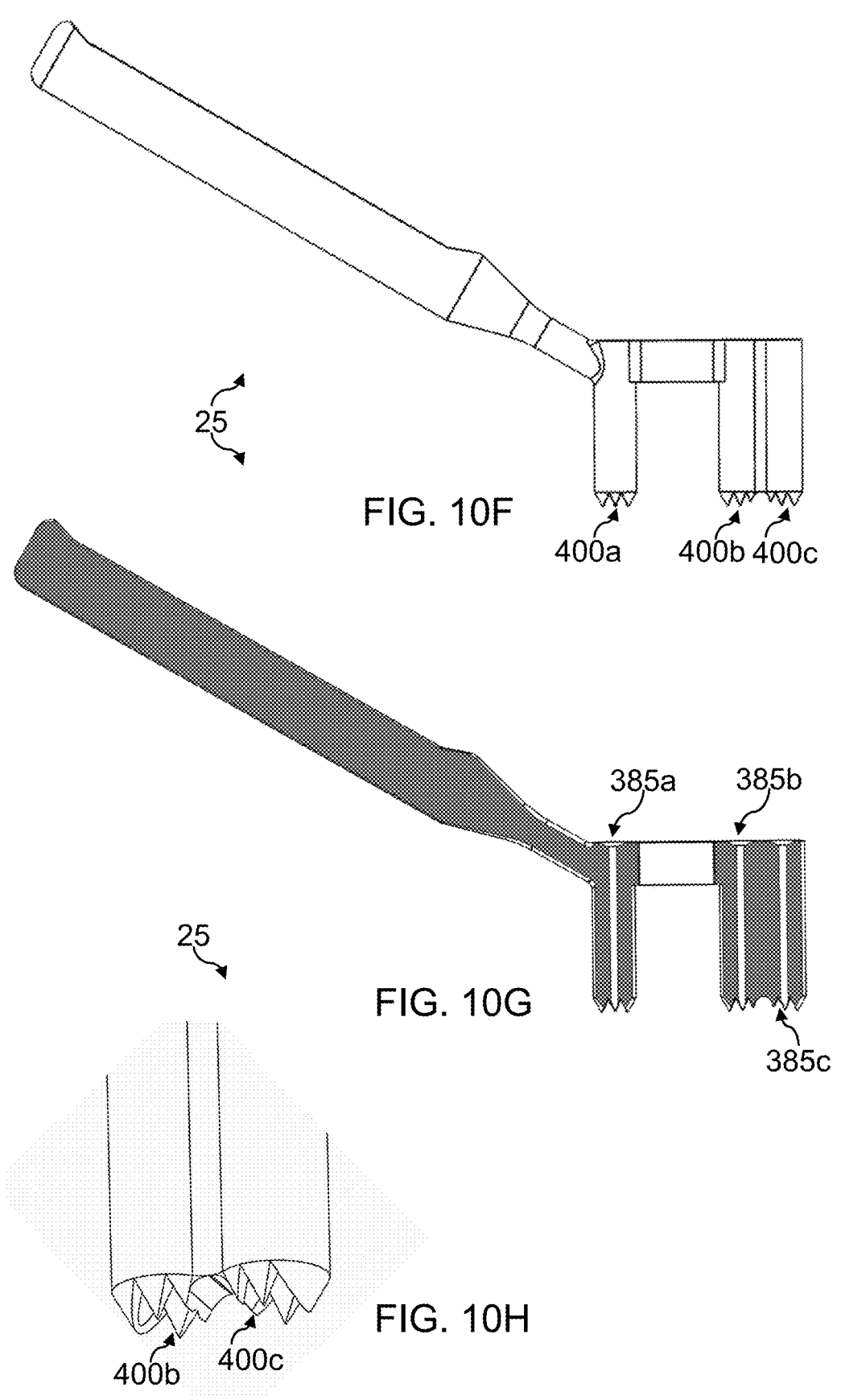
FIGS. 10G-10H depict a cross-sectional view and an exploded view of the guide tool of FIGS. 10A-10F.
Figures 11A, 11B:
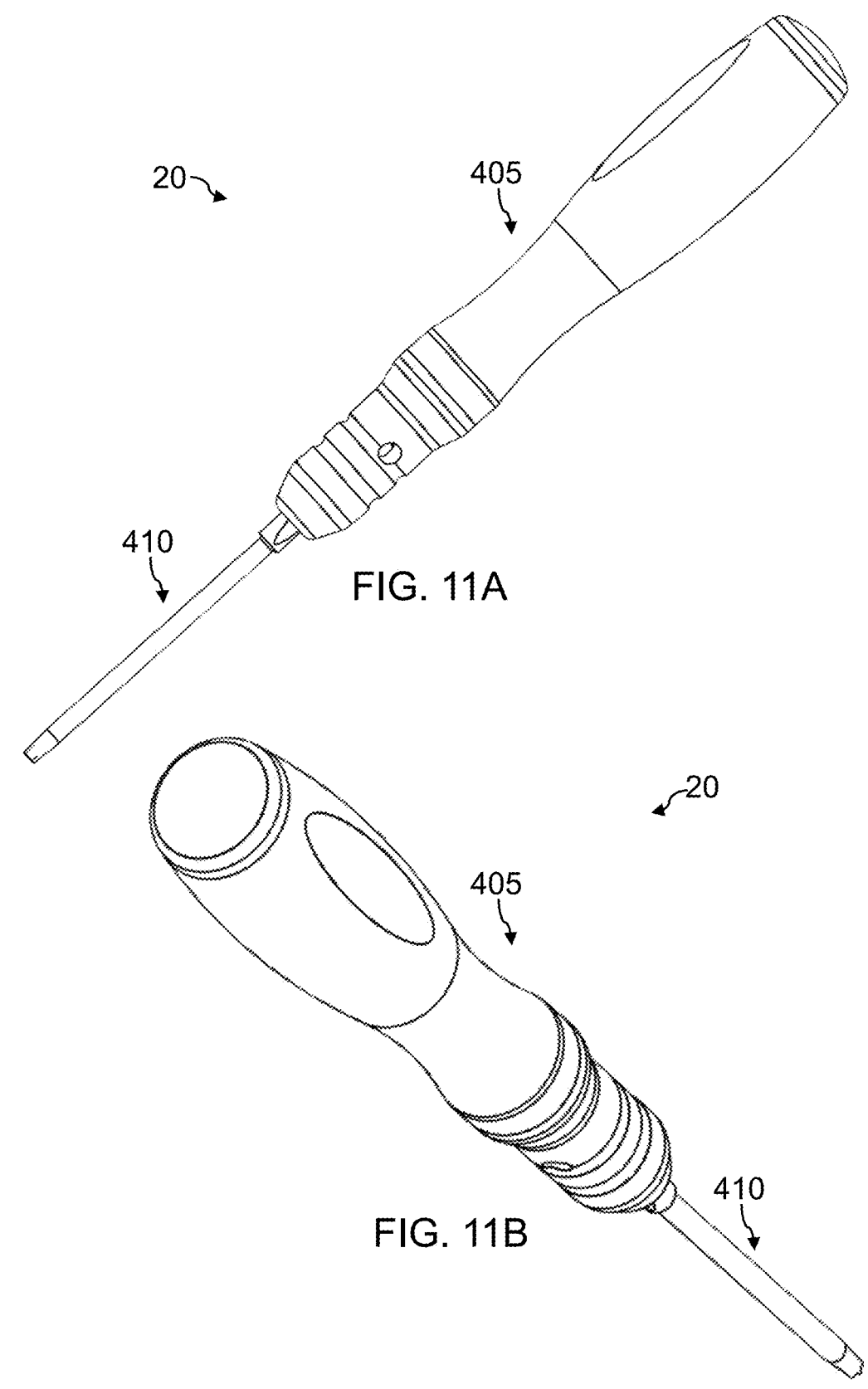
FIGS. 11A-11E depict various plan views of one embodiment of a driving tool.
Figures 11C, 11D, 11E:
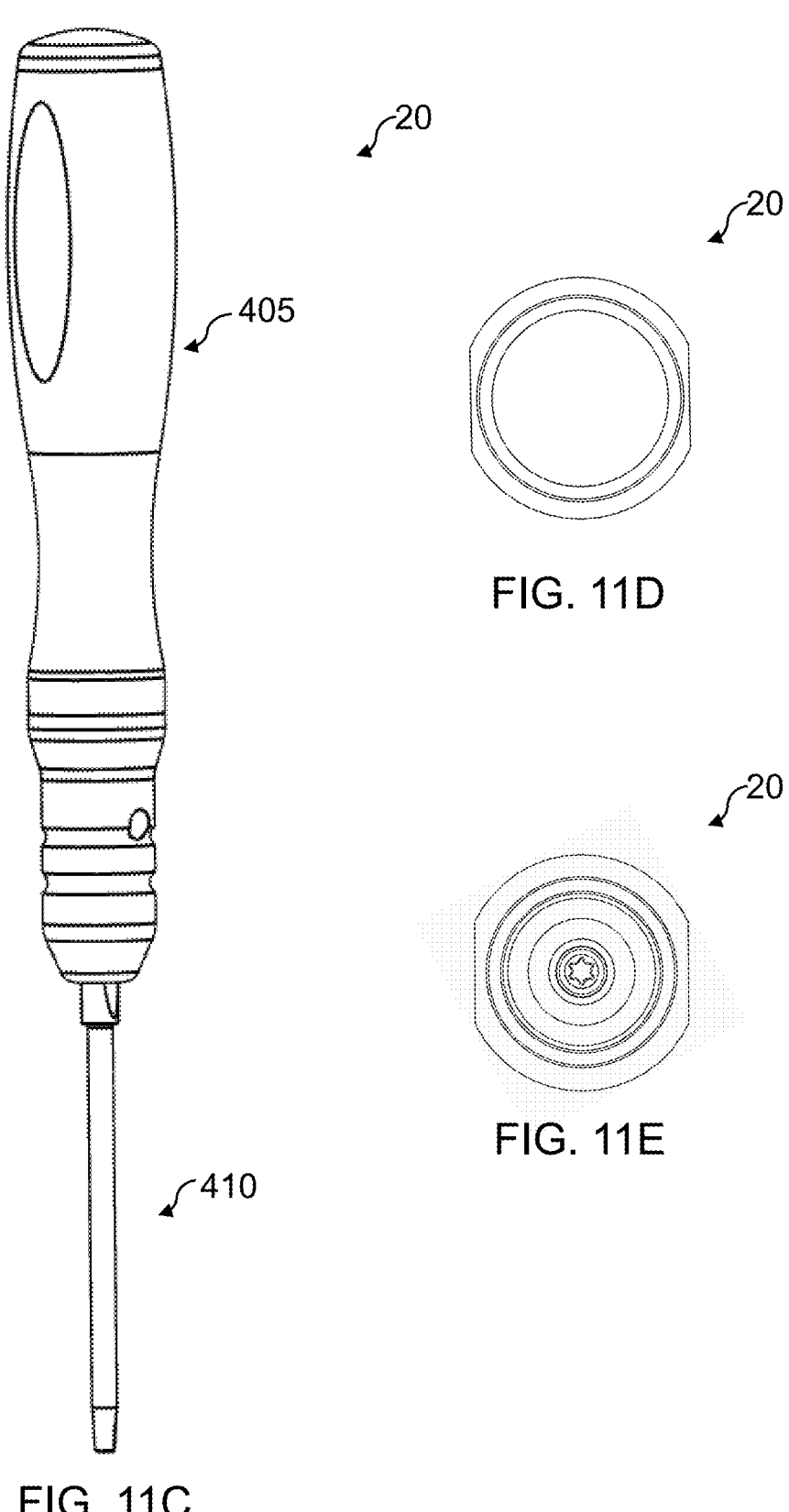
Figures 12D, 12E, 12F:
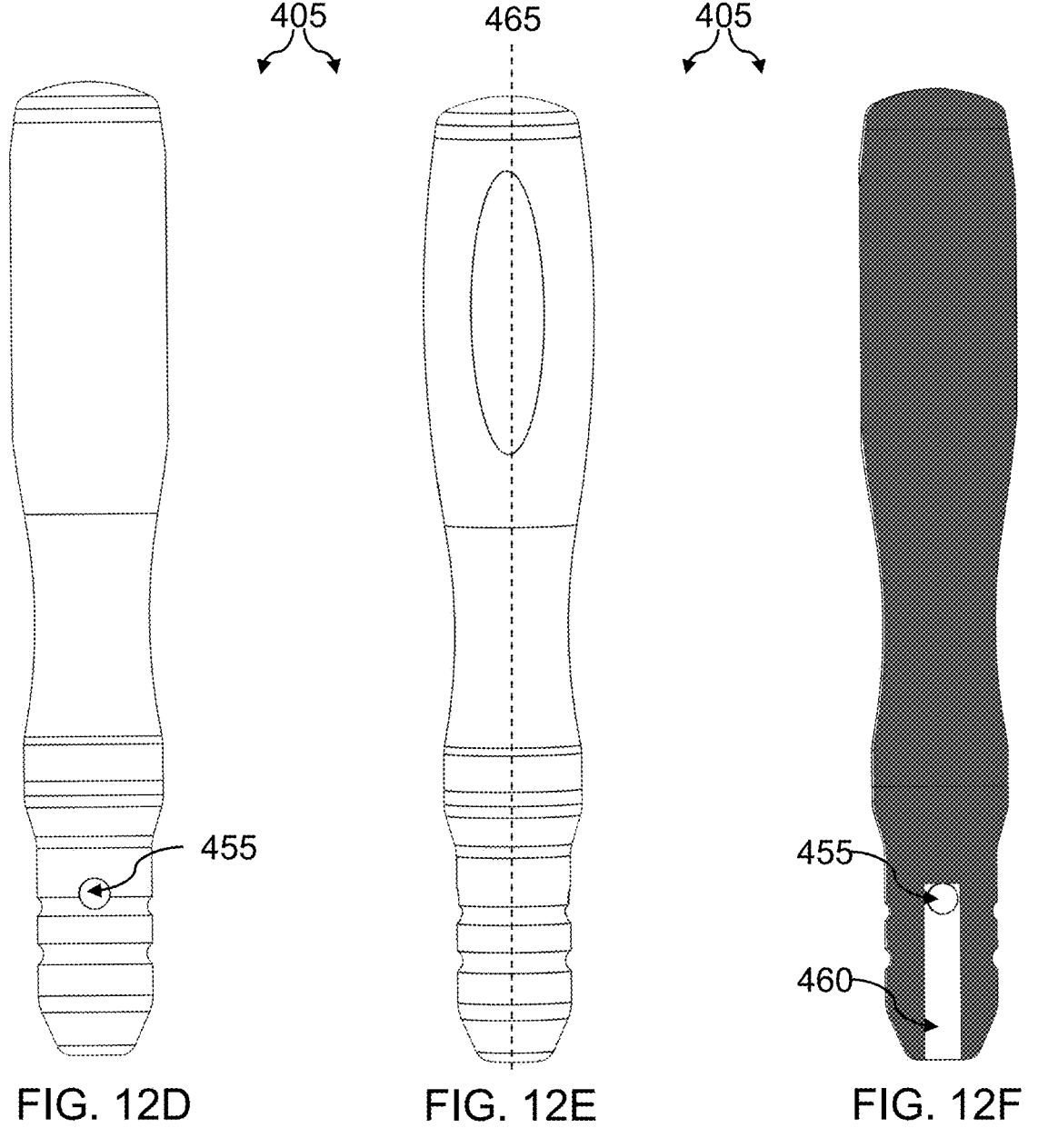
Figures 13A, 13B, 13C, 13D:
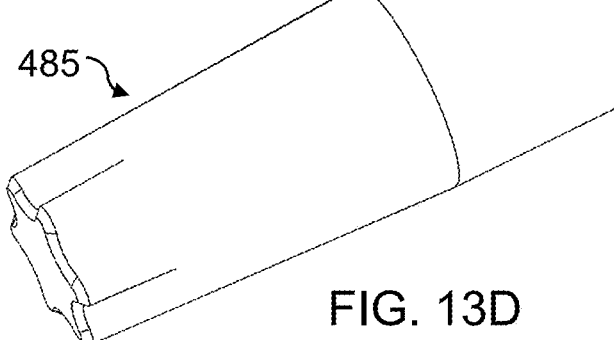
FIGS. 13A-13C depict various plan views of one embodiment of a driving tool bit.
FIG. 13D depicts an exploded view of the driving tool bit of FIGS. 13A-13C.
Figures 14A, 14B, 14C, 14D:
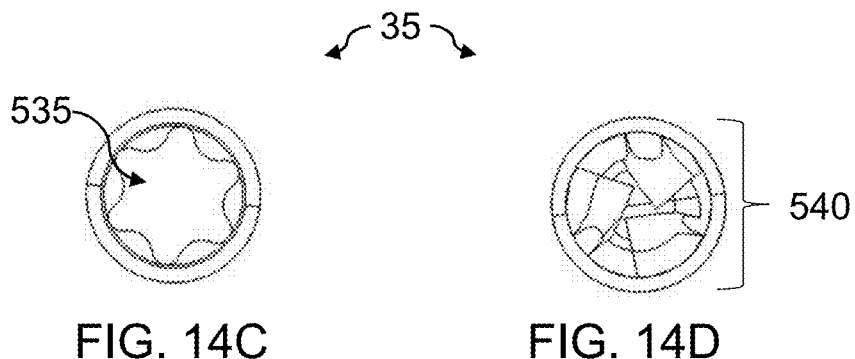
FIGS. 14A-14D depicts various plan views of one embodiment of a fixation screw.
Figures 25A, 25B:
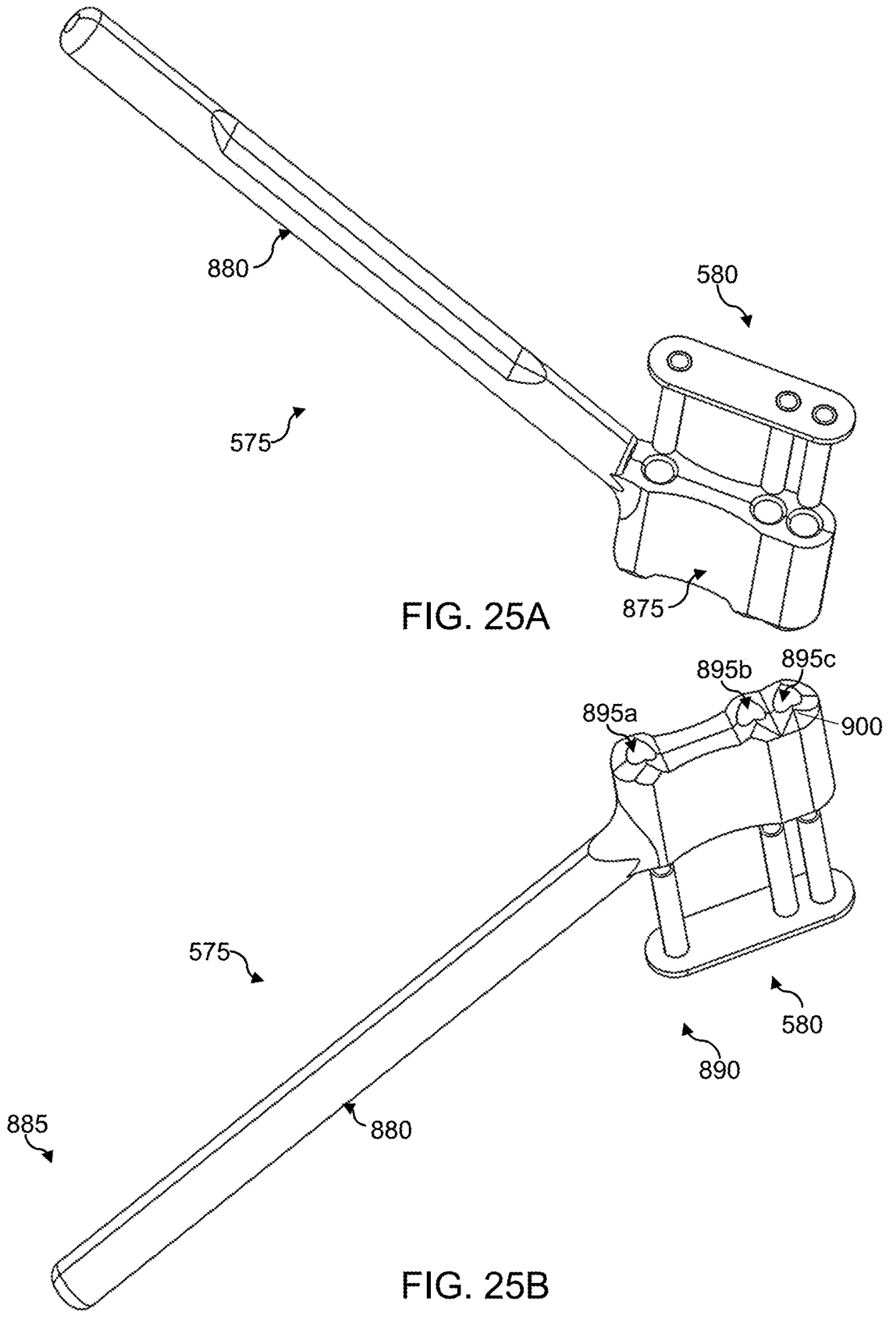
Figures 25G, 25H:
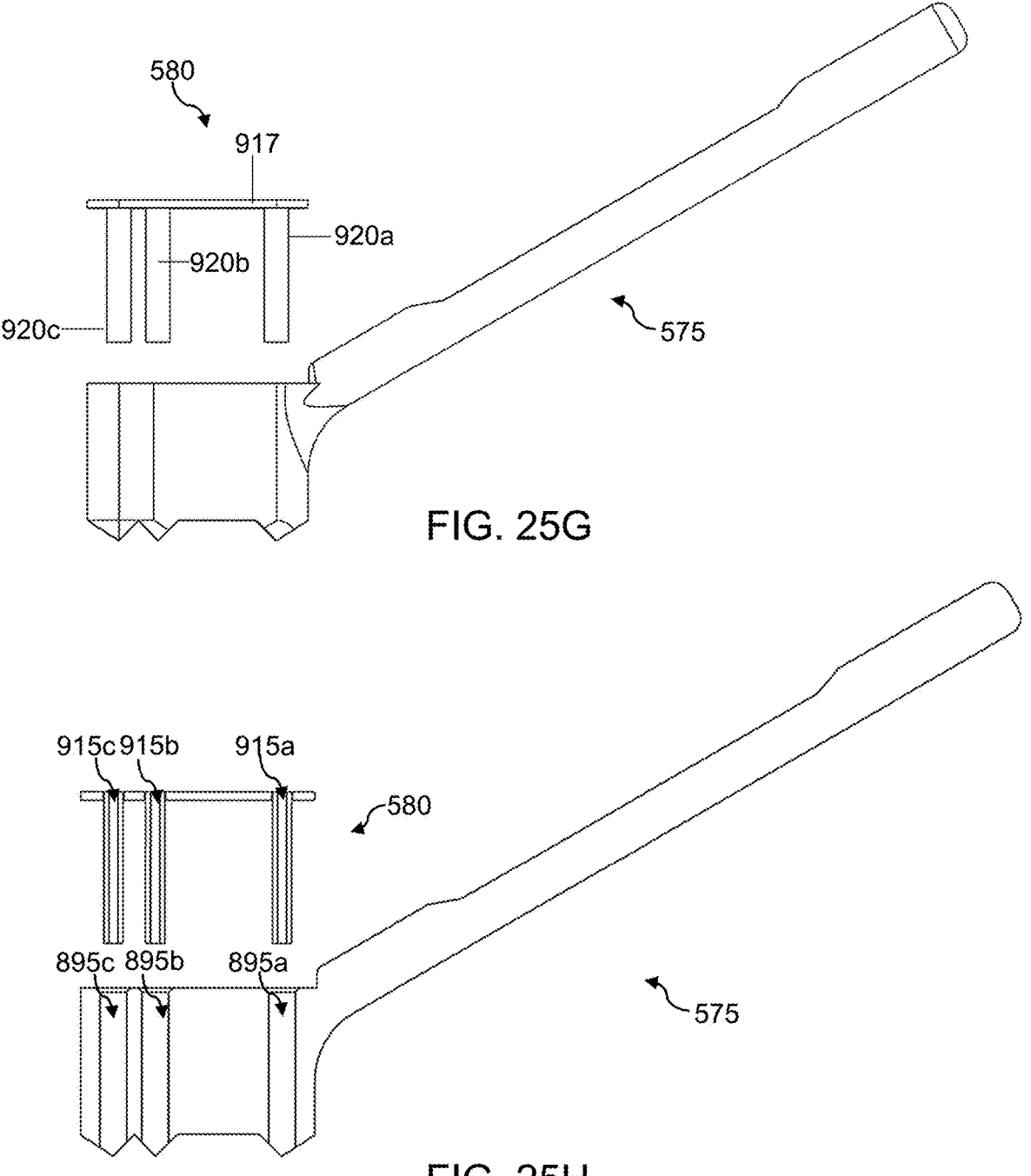

FIGS. 10A-10F and 25A-25G depict various plan views of different embodiments of a guide tool 25, 575 and FIGS. 10G-10H and 25H depict a cross-sectional view and an exploded view of the different embodiments of the guide tool 25, 575. The guide tool 25, 575 comprises a handle 370, 880 and a guide body 375, 875. The guide body 375 comprises one or more members 380a, 380b, 380c and a bridge 387. The guide body 375 comprises a first member 380a, a second member 380b, and a third member 380c. Each of the one or more guide members 380a, 380b, 380c and/or the first member 380a, a second member 380b, and a third member 380c comprises a one or more openings 385a, 385b, 385c. Each of the first member 380a, a second member 380b, and a third member 380c comprises a shape, the shape comprises cylindrical and/or hollow cylindrical shape. Alternatively, the guide body 875 of the guide tool 575 comprises one or more openings 895a, 895b, 895c and a shape. The shape comprises a substantially rectangular or round-rectangular body shape.

The one or more openings 385a, 385b, 385c, 895a, 895b, 895c are sized and configured to receive a drill wire 40 and/or one or more fixation screws 35, 595, 1075. At least one or more of the openings 385a, 385b, 385c, 895a, 895b, 895c are sized and configured to receive a drill wire 40 and/or one or more fixation screws 35, 595, 1075. Alternatively, each of one or more of the openings 385a, 385b, 385c, 895a, 895b, 895c are sized and configured to receive a drill wire 40 and/or one or more fixation screws 35, 595, 1075. The first opening 385a, 895a of the guide body 375,875 is spaced apart from the second opening 385b, 895b and the third opening 385c, 895c. The spacing includes a range of 10 mm to 20 mm. The second opening 385*b*, 895*b* and third opening 380*c*, 895*c* are adjacent or immediately adjacent to each other.

The first member 380*a* of the guide body 375 is spaced apart from the second member 380*b* and the third member 380*c*. The spacing includes a range of 10 mm to 20 mm. Each of the members 380*a*, 380*b*, 380*c* are used as guides to position and/or align the one or more fixation screws 35, 595, 1075 into the one or more prepared holes into the bone through the one or more openings 385*a*, 385*b*, 385*c*, 895*a*, 895*b*, 895*c* of the guide body 375, 875. The second member 380*b* and third member 380*c* are adjacent or immediately adjacent to each other. The bridge 387 extends between the first member 380 and the second member 380*b*. The bridge 387 comprises a length, width and thickness.

Furthermore, the guide body 375, 875 may comprise a top surface 390*a*, 390*b*, 390*c*, 897 and a bottom surface 395*a*, 395*b*, 395*c*, 903. The top surface 390*a*, 390*b*, 390*c*, 897 and/or a bottom surface 395*a*, 395*b*, 395*c*, 903 comprises surface finish (not shown) or protrusions 400*a*, 400*b*, 400*c*, 900*a*, 900*b*, 900*c*. Alternatively, at least a portion of the top surface 390*a*, 390*b*, 390*c*, 897 and/or a portion of the bottom surface 395*a*, 395*b*, 395*c*, 903 comprises surface finish (not shown) or protrusions 400*a*, 400*b*, 400*c*, 900*a*, 900*b*, 900*c*. The protrusions 400*a*, 400*b*, 400*c*, 900*a*, 900*b*, 900*c* may comprise threads, flutes, grooves, and/or teeth that may include various shapes. The various shapes may include tapered, stepped, conical and/or paralleled, flat, pointed, and/or rounded. The surface finishes may further comprise roughened surfaces or porous surfaces, including turned, blasting, sand blasting, acid etching, chemical etching, dual acid etched, plasma sprayed, anodized surfaces, and/or any combination thereof. In another embodiment, at least one of the top surfaces 390*a*, 390*b*, 390*c*, 897 and/or at least one of the bottom surfaces 395*a*, 395*b*, 395*c*, 903 of the guide body 375, 875 comprises a surface finish or protrusions 400*a*, 400*b*, 400*c*, 900*a*, 900*b*, 900*c*. The surface finish and/or protrusions 400*a*, 400*b*, 400*c*, 900*a*, 900*b*, 900*c* engage or dig into the bone to prevent migration while creating holes with one or more drill wires 40.

Figures 25I, 25J, 25K:
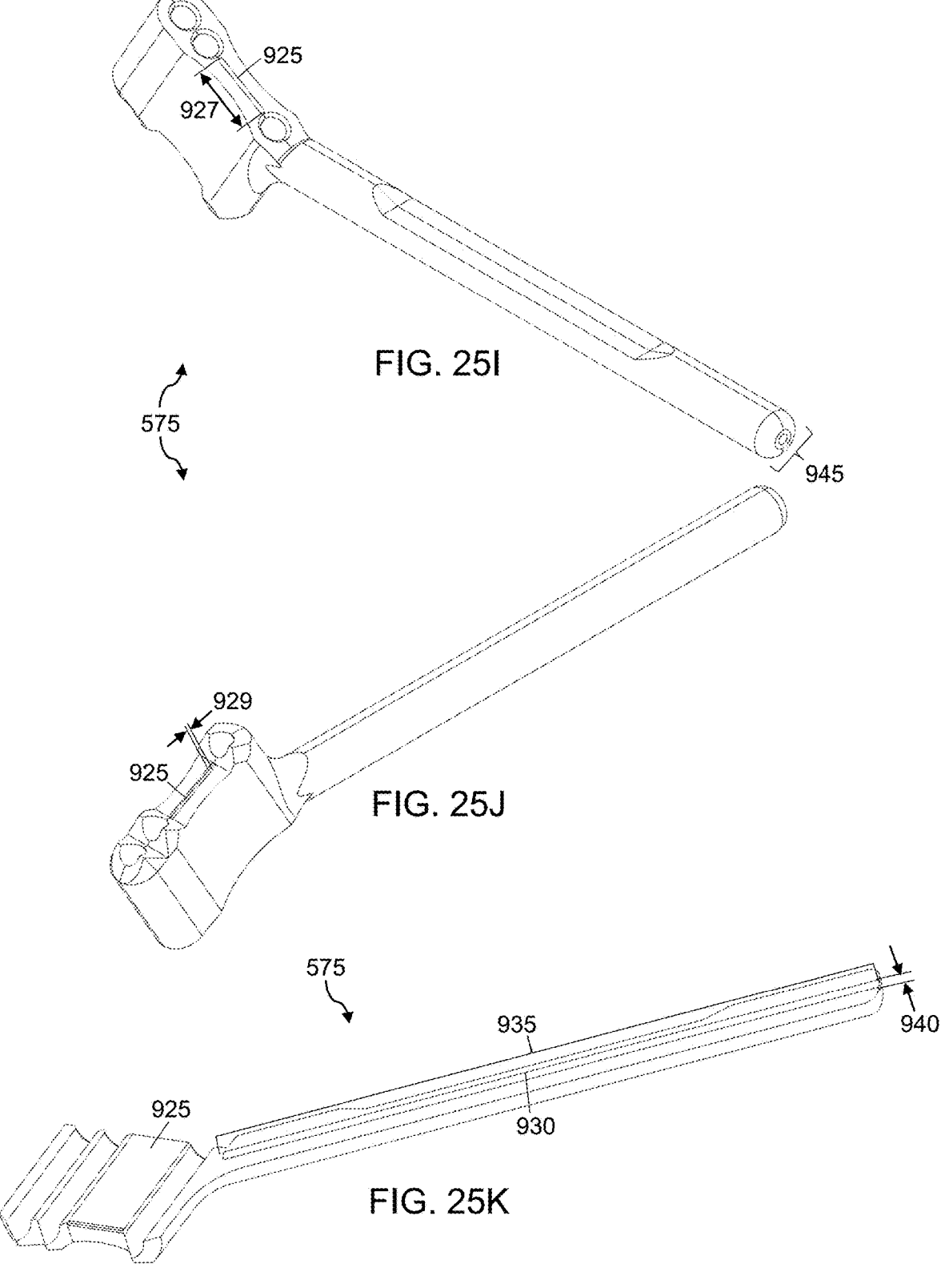
FIGS. 25I-25M depicts various plan views and a cross-sectional view of an alternate embodiment of a guide tool with at least one orientation structure.
Figures 25L, 25M:
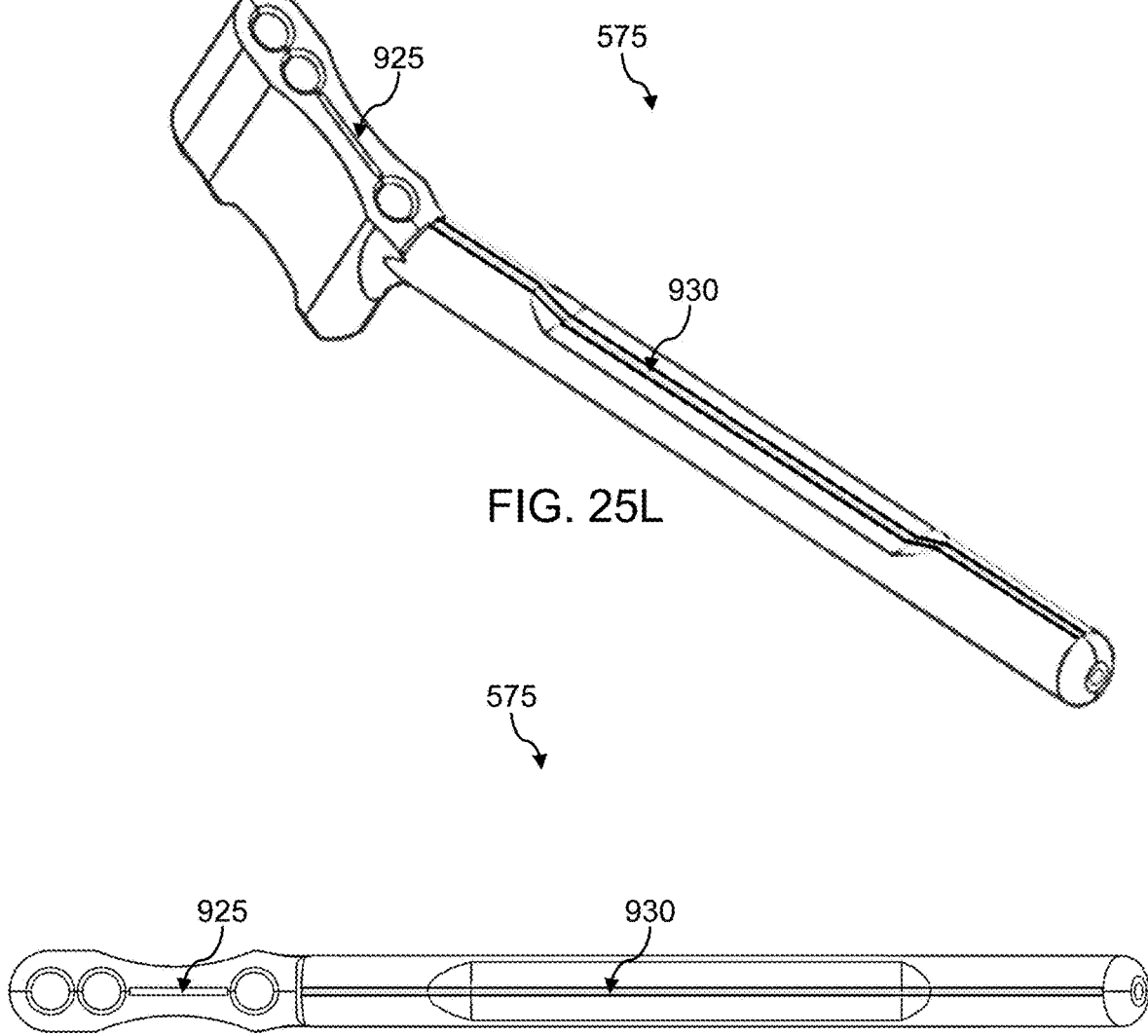

In another embodiment, the guide tool 25, 575 further comprises at least one orientation structure 925, 930 as shown in FIGS. 251-25M. The at least one orientation structure 925, 930 is a structure that will facilitate orientation to the long axis of the bones or arm bones and help guide a more accurate orientation and one or more fixation screw 35, 595, 1075 placement into the bones. The at least one structure 925, 930 may comprise a radiolucent material to be visualized during imaging. With reference to FIGS. 251-25K, the at least one orientation structure 925, 930 may be disposed within the guide body 375, 875 and/or the handle 370, 880 of the guide tool 25, 575. The at least one orientation structure 925, 930 may be disposed within the bridge 387. Each of the orientation structures 925, 930 comprises a length 935, 927 and a width 929, 940. The orientation structures 925, 930 may comprise a flat, rectangular, round, and/or cylindrical shape.

Alternatively, the guide tool 25, 575 may comprise a first orientation structure 925 and a second orientation structure 930. The first orientation structure 925 may be disposed within the bridge 387 and/or the guide body 375, 875. The first orientation structure 925 extends between the first opening 385*a*, 895*a* and the second opening 385*b*, 895*b*, 895. A top surface of the first orientation structure 925 may be flush with the top surface top surface 390*a*, 390*b*, 390*c*, 897 of the guide body 375, 875. A bottom surface of the first orientation structure 925 may be flush with a bottom surface 395*a*, 395*b*, 395*c*, 903 of the guide body 375, 875. The width 929 of the first orientation structure 925 is smaller than the width of the guide body 375, 875. The length 927 of the first orientation structure comprises a smaller length than the length of the guide body 375, 875.

The second orientation structure 930 may be disposed within a portion of the handle 370, 880 of the guide tool 25, 575. The second orientation structure 930 extends along at least a portion of a longitudinal axis of the guide handle 370, 880. The second orientation structure 930 extends parallel and/or aligns along at least a portion of the longitudinal axis of the guide handle 370, 880 of the guide tool 25, 575. The second orientation structure 930 is coaxially aligned with the first orientation structure 930. The first orientation structure 925 comprises a first longitudinal axis (not shown) and the second orientation structure 930 comprises a second longitudinal axis (not shown). The second longitudinal axis of the second orientation structure is coaxially aligned with the first longitudinal axis of the first orientation structure 925. The length 935 of the second orientation structure 930 may match or substantially match the length of the handle 370, 880 of the guide tool 25, 575. The first and/or second orientation structure 925, 930 may be solid or hollow. The width 940 of second orientation structure 930 may match or substantially match the width 945 of the handle 370, 880 of the guide tool 25, 575. Alternatively, the width 940 of second orientation structure 930 may be less than the width 945 of the handle 370, 880 of the guide tool 25, 575.

With reference to FIGS. 25L-25M, the at least one orientation structure 925,930 may be disposed on a surface and/or an outer surface of a guide handle 370, 880 and/or guide body 375, 875 of a guide tool 25, 575. In one embodiment, the guide tool 25, 575 further comprises at least one orientation structure 925, 930. The at least one orientation structure 925, 930 may be disposed on a top surface 390*a*, 390*b*, 390*c*, 897 and a bottom surface 395*a*, 395*b*, 395*c*, 903 of the guide body, 375, 875. The at least one orientation structure 375, 875 may be disposed on an outer surface of the guide handle 370, 880.

In another embodiment, the guide tool 375, 875 further comprises a first orientation structure 925 and a second orientation structure 930. The first orientation structure 925 extends between the first opening 385*a*, 895*a* and the second opening 385*b*, 895*b*, 895. The second orientation structure 930 is disposed onto a portion of the outer surface of the handle 370, 880 and along a portion of the longitudinal axis of the handle 370, 880. The second orientation structure 930 is coaxially aligned with the first orientation structure 930. The first orientation structure 925 comprises a first longitudinal axis (not shown) and the second orientation structure 930 comprises a second longitudinal axis (not shown). The second longitudinal axis of the second orientation structure is coaxially aligned with the first longitudinal axis of the first orientation structure 925.

In another embodiment, the guide tool 25, 575 comprises a material. The material may include metal, polymers or ceramic. The metals may comprise titanium, titanium alloys, cobalt-chrome alloys, platinum, stainless steel and/or any combination thereof. More specifically, the metal includes titanium and/or cobalt-chrome molybdenum (CoCrMo). The polymers may include thermoplastic or thermoset polymers. The polymers may further include composite thermoplastic or thermoset polymers and/or fiber reinforced thermoplastics or thermoset polymers. The polymers may further include carbon fiber, polyether ether ketone (PEEK), polyethylene (PE), ultra-high molecular weight polyethylene (UHMWPE), polycarbonate (PC), polypropylene (PP), polyurethanes (PU), nylon, polyolefins, and/or any combination thereof. The ceramics may include alumina ceramics, Zirconia (ZrO2) ceramics, Calcium phosphate or hydroxyapatite (Ca10(PO46(OH)2) ceramics, titanium dioxide (TiO2), silica (SiO2), Zinc Oxide (ZnO) and/or any combination thereof. The material of the guide tool 25, 575 may be the same or different than each of the materials of the proximal frame assembly 55, 610, 1145, the proximal frame 60, 640, 1210, the proximal compression bracket 65, the distal frame assembly 45, 605, 1160, the distal frame 90, 655, 1175, and/or the distal bracket 95, 660, 1165.

Accordingly, the materials may comprise radiopacity or be radiopaque. Alternatively, each of the materials may further comprise a translucent material and/or radiolucent material. Each of the materials may further comprise a radiolucent fiber reinforced composite polymer material and/or a radiolucent composite polymer material. Each of the materials may further comprise a radiolucent fiber reinforced composite polymer material and/or a radiolucent composite polymer material. The radiopacity may include radiopaque fillers or compounds, including barium sulfate, zirconium dioxide, titanium dioxide, tungsten, gold, bismuth salts, tantalum and/or any combination thereof. In one embodiment, the material may comprise a radiopaque polymer. In another embodiment, the material may comprise a polymer with a radiopaque filler. In an additional embodiment, the materials may further include color fillers.

In another embodiment, the guide tool 25, 575 may comprise a nested guide tool (not shown). The nested guide tool may comprise a first guide tool and a second guide tool. The first guide tool comprises a first handle and a first guide body, the first guide body comprises a first one or more openings and/or a first plurality of openings. The second guide tool comprises a second handle and a second guide body, the second guide body comprises a second one or more openings and/or a second plurality of openings. The first guide tool may comprise a recess, opening and/or channel. The recess, opening and/or channel extends along the length of the first handle and/or the first guide body. The recess, opening and/or channel is sized and configured to receive a portion of the second guide tool. The second guide tool can be slidably coupled to the first guide tool, allowing the second one or more openings of the second guide tool to be concentrically aligned with the first one or more openings of the first guide tool. Each of the first diameter of the first one or more openings is larger than each of the second diameter of the second one or more openings.

In another embodiment, the guide tool 25, 575 comprises an insert 580 as shown in FIGS. 16, 25A-25B and 25G-25H. At least a portion of the insert 580 is disposed into the one or more openings 385a, 385b, 385c, 895a, 895b, 895c of the guide body 375, 875 to accommodate and align the drill wire 40 more accurately. The insert 580 comprises a base plate 917 and one or more tubes 920a, 920b, 920c. The one or more tubes 920a, 920b, 920c extend downwardly from a bottom surface of the base plate 917, 920a, 920b, 920c. The one or more tubes 920a, 920b, 920c extend perpendicular from the base plate 917. Each of the one or more tubes 920a, 920b, 920c comprise a lumen 915a, 915b, 915c. Each of the lumens are sized and configured to receive a drill wire 40. The one or more tubes 920a, 920b, 920c are sized and configured to be disposed into each of the one or more openings 385a, 385b, 385c, 895a, 895b, 895c of the guide body 375, 875. The one or more tubes 920a, 920b, 920c are sized and configured to be disposed into each of the one or more openings 385a, 385b, 385c, 920a, 920b, 920c of the guide body 375, 875 until at least a portion of the bottom surface of the base plate 917 contacts or engages a portion of the top surface 390a, 390b, 390c, 897 of the guide body 375, 875. Each of the one or more tubes 920a, 920b, 920c are spaced to match and/or substantially match the spacing of each of the guide members 380a, 380b, 380c and/or the one or more openings 385a, 385b, 385c, 920a, 920b, 920c of the guide body 375, 875.

FIGS. 1, 11A-11E, 12A-12F, 13A-13D, 16, 26A-26H, 27A-27C and 28A-28F depict various plan views of one embodiment of a driving tool 20, 590. The driving tool 20, 590 may comprise a driving tool handle 405, 955 and the driving tool shaft 410, 950. The driving tool 20, 590 may comprise manual application and/or electrically powered application. The driving tool 20, 590 is used to engage with the one or more fixation screws 35, 595, 1075 and the one or more fasteners 75, 80a, 80b, 620, 625, 1170, 1230 to secure the one or more fixation screws 35, 595, 1075 into the relevant bone and/or secure the one or more fixation screws 35, 595, 1075 to the proximal frame assembly 55, 610, 1145 and/or the distal frame assembly 45, 605, 1160.

The driving tool handle 405, 955 comprises a first end 415 and a second end 420, an outer diameter 470, 963 and a shape. The shape will comprise an ergonomic shape to allow the surgeon to grasp the driving tool handle 405, 955 with ease. The driving tool hand 405, 955 may further comprise one or more colors to assist the surgeon to secure the fixation screws 35, 595, 1075 and/or the fasteners 75, 80a, 80b, 620, 625, 1170, 1230. In one embodiment, the external fixator system 5, 565 may comprise a first driving tool and a second driving tool. The first driving tool comprises a first driving tool handle. The second driving tool comprises a second driving tool handle. The first driving tool handle may comprise a first color and the second driving tool handle comprises a second color. The first color is different than the second color. Each of the first and/or second color can be color coded to the fixation screws 35, 595, 1075 and/or the fasteners 75, 80a, 80b, 620, 625, 1170, 1230.

In one embodiment, the driving handle 405, 955 comprises a fastener opening 455. The fastener opening 455 is positioned at a first end 415 and/or a second end 420. The fastener opening 455 is positioned at the second end 420. Alternatively, the fastener opening 455 is positioned proximate to the second end 420. The fastener opening 455 is perpendicular or substantially perpendicular to the driver shaft opening 460, 970 and/or the driver handle longitudinal axis 465. The fastener opening 455 extends only a portion of the outer diameter 470 of the driving tool handle 405, 955. The fastener opening 455 is sized and configured to receive a fastener (not shown) to secure the driving tool shaft 410 to the driving tool handle to prevent it from migrating and/or loosening.

In another embodiment, the driving handle 405, 955 comprises a shaft opening 460, 970. The shaft opening 460, 970 is sized and configured to receive a portion of the driving tool shaft 410, 950 as shown in the cross-sectional view of FIGS. 12F, 26G-26H and 27C. The driving shaft opening 460, 970 is positioned at the second end 420 and/or proximate to the second end 420. The driving shaft opening 460, 970 is aligned with the longitudinal axis 465 of the driving handle 405, 955. The driving shaft opening 460 is centrally located or centrally positioned. The driving shaft opening 450, 970 extends from the second end 420 towards a portion of the first end 415. The diving shaft opening 450, 970 extends from a bottom surface of the driving handle 405, 955 towards a portion of the top surface of the driving handle 405, 955.

Figures 26A, 26B, 26C, 26D:
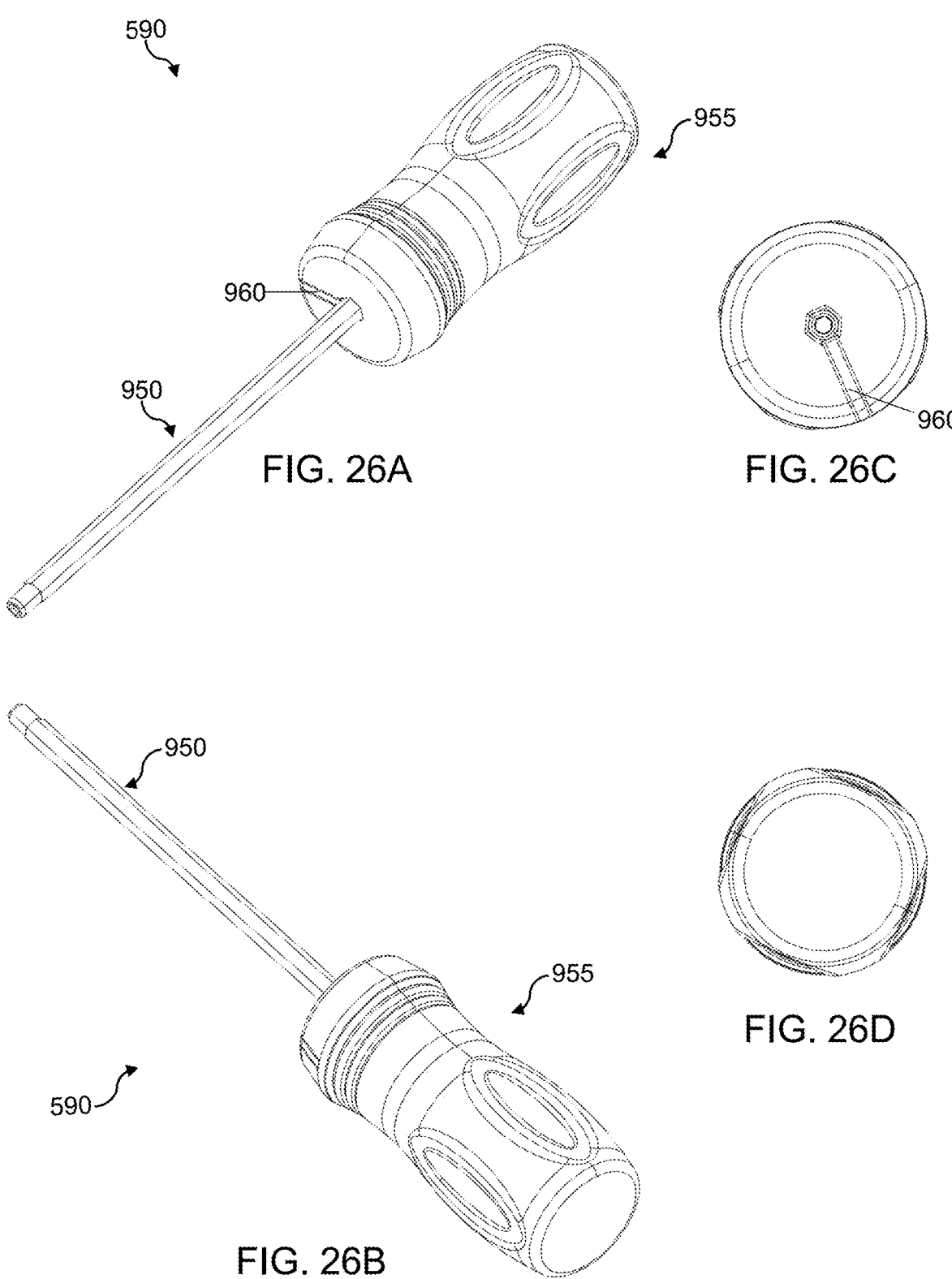
FIGS. 26A-26F depict various plan views of an alternate embodiment of a driving tool.
Figures 26E, 26F, 26G, 26H:
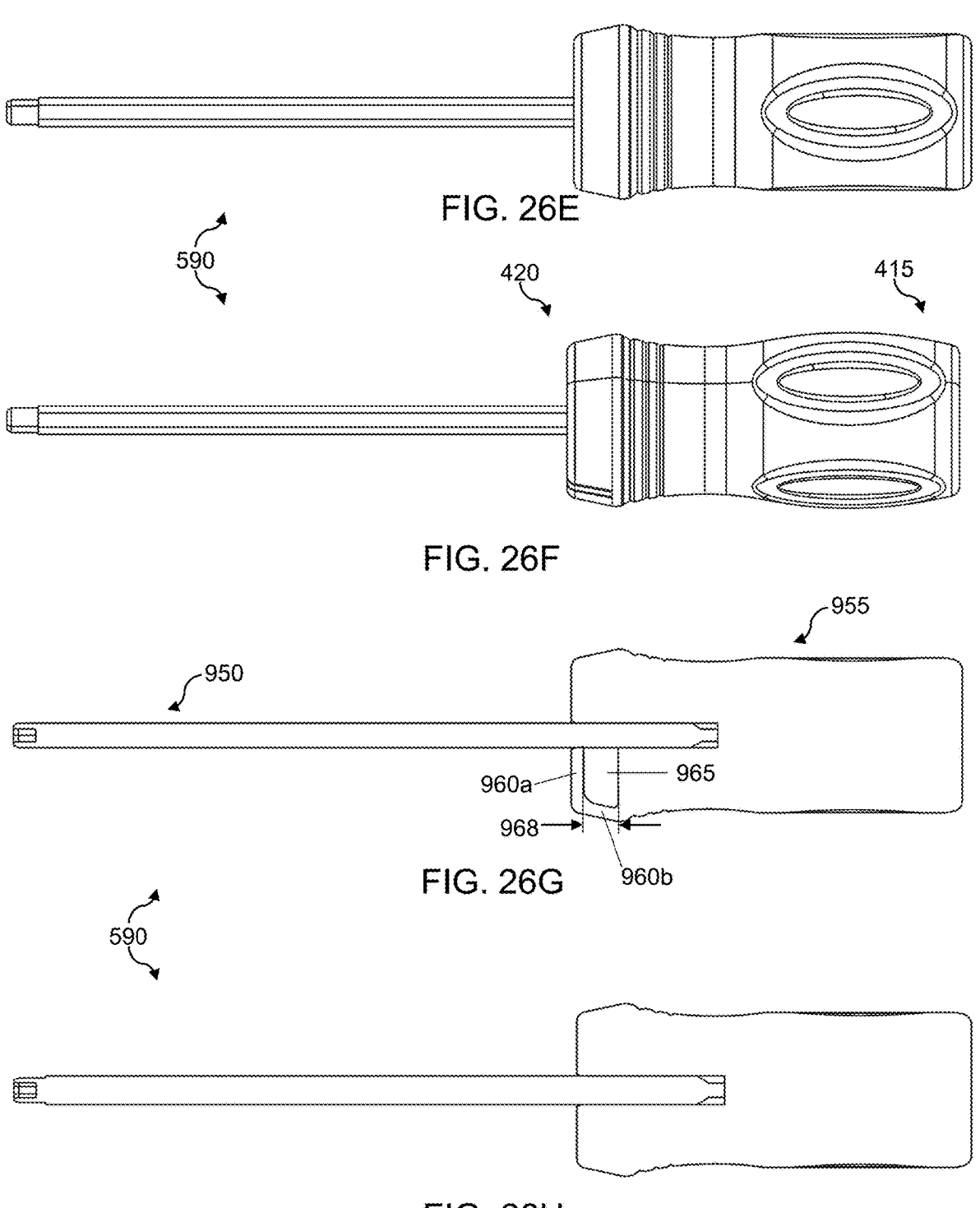
FIGS. 26G-26H depict cross-sectional views of the driving tool of FIGS. 26A-26F.
Figures 27A, 27B, 27C:
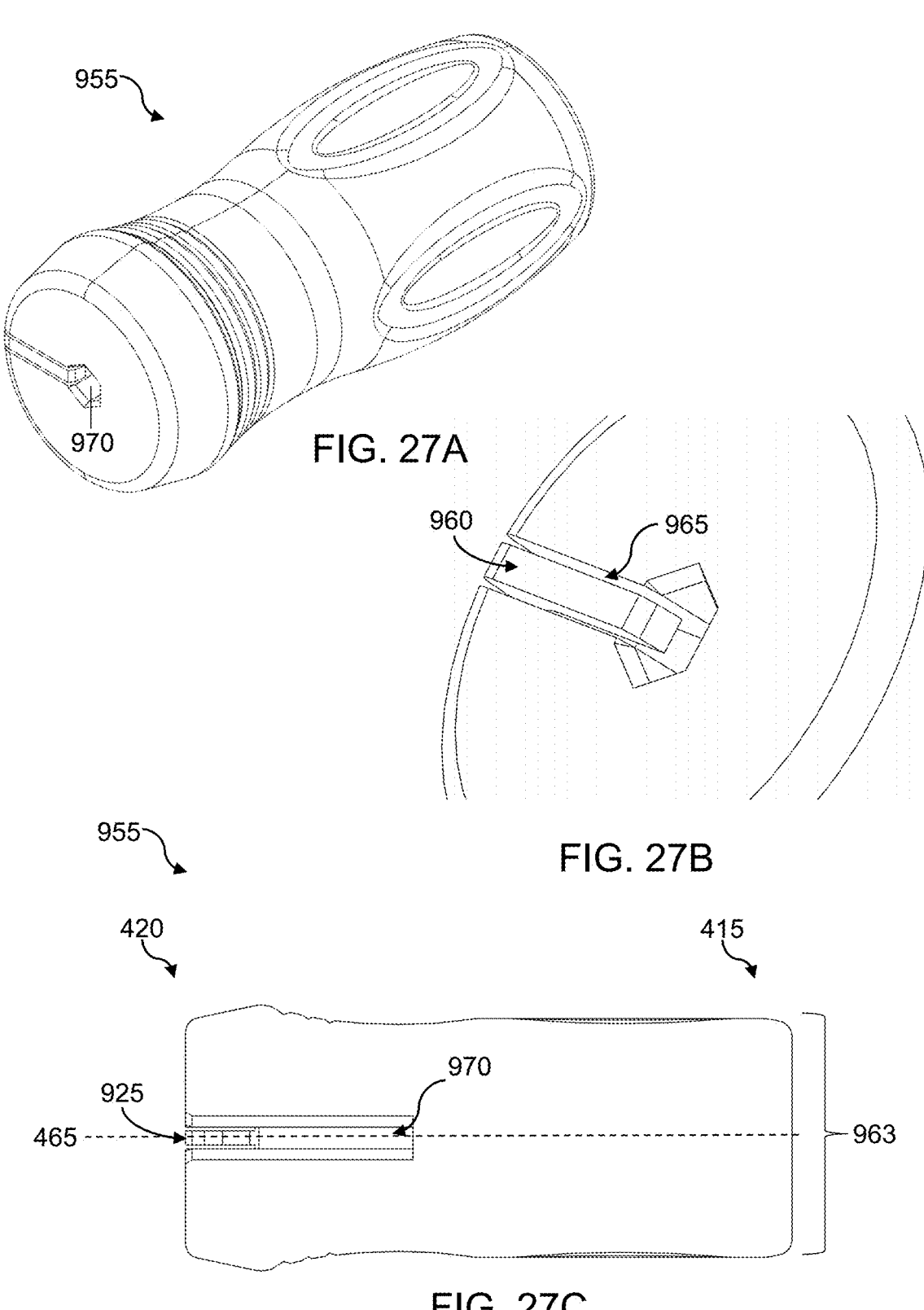
FIGS. 27A-27C depict various plan views of an alternate embodiment of a driving tool handle.
Figures 28A, 28B, 28C, 28D, 28E, 28F:
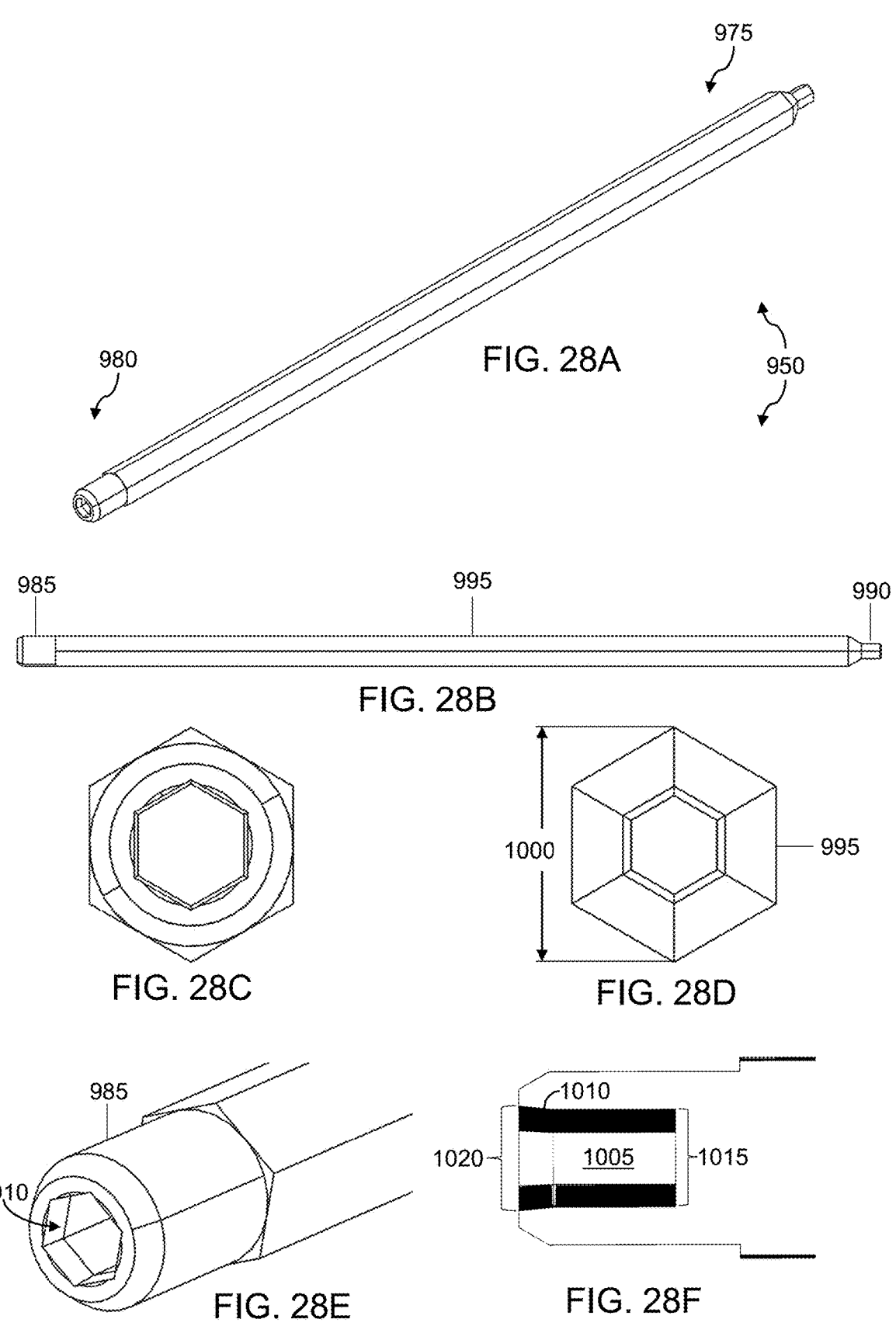
FIGS. 28A-28D depict various plan views of an alternate embodiment of a driving tool bit.
FIG. 28E-28F depicts an exploded view and a cross-sectional view of the alternate embodiment of a driving tool bit of FIGS. 28A-28D.
Figures 31A, 31B:
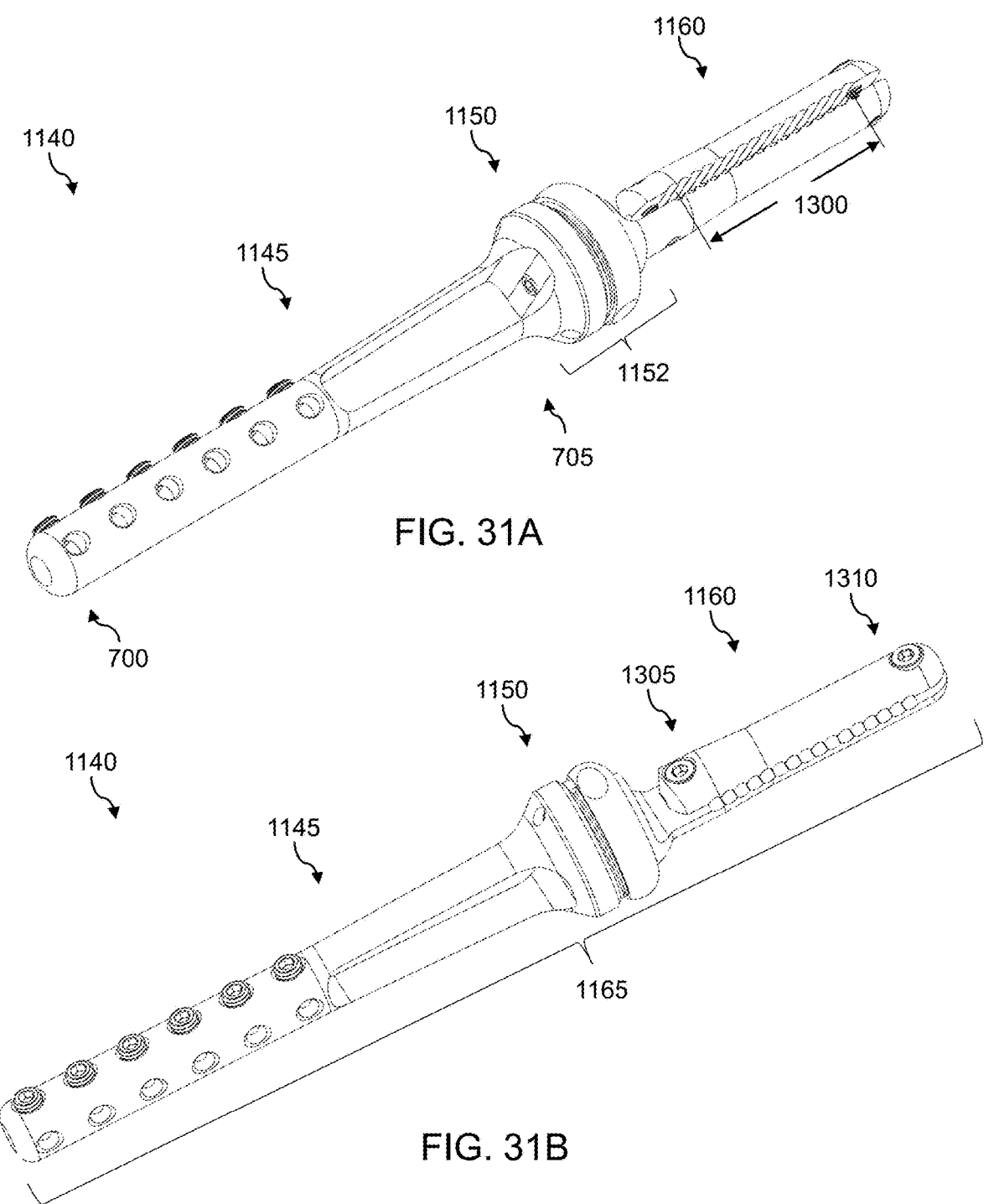
FIGS. 31A-31B depicts isometric views of an alternate embodiment of an external fixator assembly.
Figure 32:
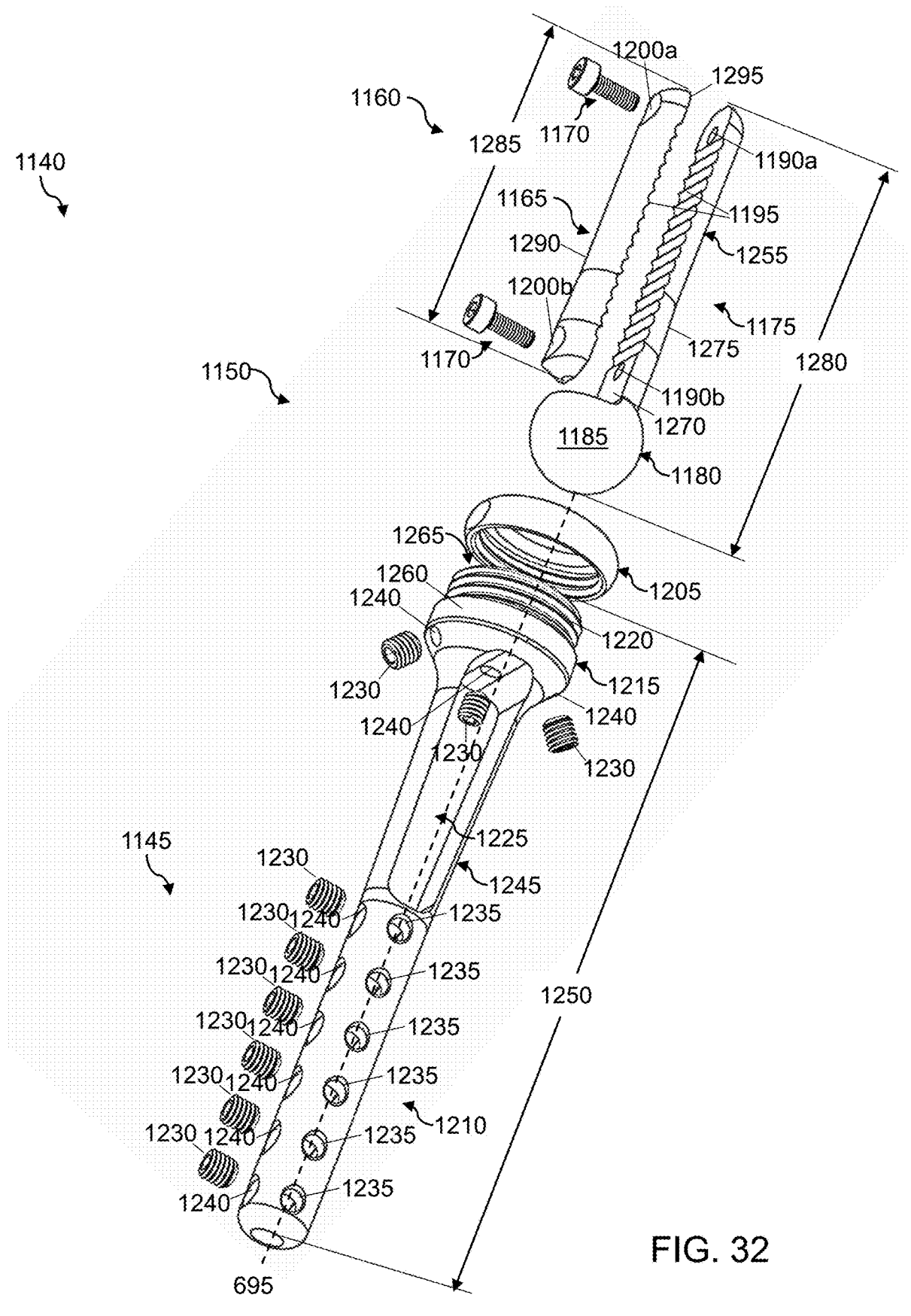
FIG. 32 depicts an exploded view of the alternate embodiment of an external fixator assembly of FIGS. 31A-31B.

In another embodiment, the driving handle 405, 955 may comprise a channel 965 as shown in FIG. 26H. The channel 965 is positioned within or adjacent to the second end 420 of the driving handle 405, 955. The channel 965 extends transverse to the longitudinal axis 465 of the driving handle 405, 955. The channel 965 is sized and configured to receive a portion of a retention mechanism 960*a*, 960*b*. The channel 965 further comprises a channel width 968, the channel width 968 allows sufficient space for the retention mechanism 960*a*, 960*b* to flex inward without interference.

In another embodiment, the driving handle 405, 955 may further comprise a retention mechanism 960. The retention mechanism 960 is configured to secure or retain a portion of the driving tool shaft 410, 950 and prevent sliding or disengagement. The retention mechanism comprises a first arm 960*a* and a second arm 960*b*. The second arm 960*b* extends from the first arm 960*a*. The second arm 960*b* extends perpendicular and/or substantially perpendicular from the first arm 960*a*. At least a portion of the retention mechanism 960*a*, 960*b* is disposed into the channel 965. The second arm 960*b* is parallel and/or substantially parallel to the longitudinal axis 465 of the driving handle 405, 955. The first arm 960*a* is perpendicular and/or transverse to the longitudinal axis 465 of the driving handle 405, 955. The first arm 960*a* is movable relative to the second arm 960*a*. The first arm 960*a* moves from a first neutral position to a second position that allows at least a portion of the first arm 960*a* to flex or bend inwardly within the channel 965 until the first arm 960*a* engages with the outer surface 995 of the driving shaft 410, 950.

The driving tool shaft 410, 950 may comprise a shank 475, a body 480, 995 and at least one tip 485, 985, 990. The shank 475 may comprise a 1-, 2- or 3-sided flat shank, a reduced shank, and/or a tanged shank. If the shank 475 comprises a 1-sided flat shank, the shank includes a flat surface 490 that allows a strong grip from the fastener (not shown) to reduce the possibility of the fastener or the driving shaft 410, 950 slipping within the driving handle 405, 955. In one embodiment, the body 480 is positioned between the shank 475 and the tip 485. In another embodiment, the body 995 is positioned between a first tip 990 and a second tip 985. The body 480, 995 may comprise a shape, the shape is a solid, cylindrical shape and/or a solid polygonal shape. The solid polygonal shape may comprise a hexagon. The at least one tip 485, 985, 990 is positioned at one end of the driving tool shaft 410, 950. The at least one tip 485, 985, 990 may comprise a shape or style to engage with a fixation screw 35, 595, 1075, a fastener 75, 620,625, 1170, 1230 and/or a locking fastener 80*a*, 80*b*. The at least one tip shape or style may include a slotted, a Phillips, a square, a hex or Allen, a hexalobular, Torx, and/or any combination thereof. The at least one tip 485, 985, 990 may comprise a male and/or female receiver or socket tip. The driving tool shaft 410, 955 and the driving handle 405, 955 may comprise a material, the material includes a metal or polymer. The material may also comprise any material known in the art to facilitate the securement of the fixation screws 35, 595, 1075 and/or the fasteners 75, 80*a*, 80*b*, 620, 625, 1170, 1230.

In another embodiment, the driving tool shaft 410, 950 may comprise a dual ended driving tool shaft 410, 950. The dual ended driving tool shaft comprises a body 480, 995, a first bit tip 990 and a second bit tip 985. The body 480,995 may comprise a 1-, 2- or 3-sided flat shank or body, a reduced shank or body, and/or a tanged shank or body. If the shank or body 480, 995 comprises a 1-sided flat shank, the shank or body 480, 995 includes a flat surface that allows a strong grip from the fastener (not shown) to reduce the possibility of the fastener or the drill bit slipping within the driving handle. The shank and/or body 480, 995 comprises a first end 473, 975 and a second end 478, 980. The first bit tip 990 is positioned at the first end of the body 480, 975 and the second bit tip 985 is positioned at the second end 980 of the body 480, 995. The first bit tip 990 and/or the second bit tip 985 may comprise a male and/or a female receiver or socket tip. The first bit tip 990 and/or second tip 985 may comprise a shape or style to engage with a fixation screw, a fastener and/or a locking fastener. The tip shape or style may include a slotted, a Phillips, a square, a slotted, a hex or Allen, a hexalobular, Torx, and/or any combination thereof. The first end 473, 975 is disposed and/or inserted into the shaft opening 460, 970 of the driving tool handle 405, 955.

In one embodiment, the first end or first bit tip 990 may comprise a male hex bit tip and the second end or second bit tip 985 comprises a female socket hex bit tip. The female socket bit tip comprises a recess 1005. The recess 1005 comprises a first portion and a second portion. The second portion extends from the first portion. The second portion is flared or tapered 1010 outwardly from the first portion. Alternatively, the first portion of the recess 1005 comprises a first diameter 1015, the second portion of the recess 1005 comprises a second diameter 1020. The second diameter 1020 is different than the first diameter 1015 and/or the second diameter 1020 is larger than the first diameter 1015.

The driving tool shaft 410, 950 and the driving tool handle 405, 955 may comprise a material, the material includes a metal or polymer. At least a portion of an inner surface of the second portion of the recess may contact and/or engage a portion of the cut or clipped fixation screw. The cut or clipped fixation screw 35, 595, 1075 may comprise a flared end on the shank that may be disposed into second portion of the recess 1005. The material may also comprise any material known in the art to facilitate the securement of fasteners and screws.

FIGS. 1, 14A-14D, 16, 29A-29E and 30A-30D depict various plan views of different embodiments of the fixation screws or Shantz screws 35, 595, 1075. The fixation screws 35, 595, 1075 is specifically designed to optimize the bone to screw interface and have a lower profile compared to commercially available fixation screws. The fixation screw 35, 595, 1075 comprises a shaft or shank 500, 1030, 1100, a body 505, 1035, 1105 and threads 510, 1040, 1110. The shaft or shank 500, 1030, 1100 may further comprise a driver opening 535. The shaft or shank 500, 1030, 1100 comprises a driver opening 535 positioned at a top surface of the fixation screw 35, 595, 1075. The driver opening 535 comprises a shape, the shape is sized and configured to receive a tool bit tip 485, 985, 990 of the driving tool shaft 410, 950 of the driving tool 20, 590. The shape comprises a slotted, a Phillips, a square, a hex or Allen, a hexalobular, Torx, and/or any combination thereof.

The outer diameter or outer surface of the shaft or shank 500, 1030, 1100 may comprise one or more shapes. The outer diameter or outer surface of the shaft or shank 500, 1030, 1100 may comprise a first portion and a second portion. The first portion comprises a first shape and the second portion comprises a second shape. The one or more shapes, first shape and/or the second shape shank 500, 1030, 100 comprises cylindrical, circular, and/or polygonal shapes. The polygonal shape includes a square, a pentagon, and/or a hexagon. The polygonal shape may comprise a male hex. The shank 500, 1030, 100 and/or at least a portion of the shank 500, 1030, 1100 may comprise a surface finish. The surface finish may include a rough or smooth surface finish. The rough surface finish may comprise sandblasting, knurling, tumbled, teeth, and/or any protrusions. The top or bottom end surface finish may also be helpful to a surgeon to determine depth of bone insertion and/or the amount to cut or clip a portion of the shank 500, 1030, 1100.

In one embodiment, the second portion comprises a cylinder or a cylinder shape and the first portion comprises a male hex. The male hex or the first portion may extend from the second portion. The male hex or the first portion may extend upwardly from the second portion or cylinder. The male hex may extend and be aligned with the longitudinal axis of the fixation screw 35, 595, 1075. The male hex may be elongated. The elongated male hex comprises a hex length 1080, 1085. The hex length 1080,1085 may comprise at least fifty percent or greater than a total shank length 528, 1045, 1090. Accordingly, the hex length 1080, 1085 may be substantially the same length and/or smaller than the total shank length 528, 1045, 1090. The elongated male hex may allow the surgeon to cut or clip a portion of the male hex length to adjust to the proper overall length 515, 1025, 1095 of the fixation screws 35, 595, 1075 to prevent the profile of the external fixation assemblies 30, 570, 1140 to be obtrusive and/or generally decrease its overall profile.

Alternatively, the at least a portion of the shank 500, 1030, 1100, the elongated male hex or the first portion may be cut or clipped to reduce the hex length 1080,1085 and/or total shank length 528, 1045, 1090 to allow a portion of the top surface of the fixation screw 35, 595, 1075 to be flush with a top surface of any of the distal frame assembly 45, 605, 1160, distal frame bracket 95, 660, 1165 and/or distal frame 90, 655, 1175, the proximal frame assembly 55, 610, 1145. In another embodiment, at least a portion of the elongated male hex may be cut or clipped to allow a top surface of the fixation screw 35, 595, 1075 to be above or below the at least one surface or top surface of the distal frame assembly 45, 605, 1160, distal frame bracket 95, 660, 1165 and/or distal frame 90, 655, 1175, the proximal frame assembly 55, 610, 1145. The cutting or clipping of the shank 500, 1030, 1100, the extended male hex or the first portion may change the shape slightly, the cut or clipped male hex or shank 500, 1030, 1100 may be disposed into the second portion of the recess 1005 of the female socket tip of the driving shaft 410, 950 of the driving tool 20, 590.

The body 505, 1035, 1105 of the fixation screw 35, 595, 1075 is a solid cylindrical shape. The body 505, 1035, 1105 is positioned between the shaft or shank 500, 1030, 1100 and the threads 510, 1040, 1110. The body 505, 1035, 1105 may further comprise one or more markers 530a, 530b, 1060a, 1060b, 1113a, 1113b. The one or more markers 530a, 530b, 1060a, 1060b, 1113a, 1113b may be positioned along a length and/or longitudinal axis of the body 505, 1035, 1105. Alternatively, the one or more markers 530a, 530b, 1060a, 1060b, 1113a, 1113b may be positioned along the total shank length 528, 1045, 1090. The one or more markers 530a, 530b, 1060a, 1060b, 1113a, 1113b may surround the entire diameter of the body 505, 1030, 1100 and/or at least a portion of the diameter of the body 505, 1030, 1100. The one or more markers 530a, 530b, 1060a, 1060b, 1113a, 1113b may surround the entire diameter of the shank 500, 1030, 1100 and/or at least a portion of the diameter of the shank 500, 1030, 1100.

The one or more markers 530a, 530b, 1060a, 1060b, 1113a, 1113b may include radiopaque markers and/or depth markers. The fixation screw 35, 595, 1075 comprises a total length 515, 1025, 1095. The total length 515, 1025,1095 may be available in a range of 40 mm to 80 mm; it may include a range of 40 to 60 mm; a range of 40 to 70 mm; a range of 50 to 70 mm; and/or a range of 60 to 70 mm. The total length 515, 1025, 1095 may include at least 50 mm; it may include at least 60 mm; it may include at least 65 mm. In an alternative embodiment, the total length 515, 1025, 1095 may comprise only one length. The one or more markers 530a, 530b, 1060a, 1060b, 1113a, 1113b may allow the surgeon to determine the depth (e.g. depth markers) of insertion into the bone and/or the amount of the shank or a portion of the shank 500, 1030, 1100 to be cut or clipped. The one or more markers 530a, 530b, 1060a, 1060b, 1113a, 1113b may be created by laser and/or machining.

The fixation screw 35, 595, 1075 may further comprise threads 510, 1040, 1110. The threads 510, 1040, 1110 may comprise self-tapping, self-drilling, tapered threaded, and/or any combination thereof. The threads 510 may comprise a thread length 525, 1055, 1098. The thread length 525, 1055, 1098 may comprise lengths of 10 mm to 80 mm; it may comprise lengths of 10 mm to 60 mm; it may comprise lengths of 10 mm to 40 mm; and/or it may comprise lengths of 10 mm to 20 mm. The thread length 525, 1055, 1098 may comprise at least 10 mm; the thread length 525, 1055, 1098 may comprise at least 15 mm; the thread length 525, 1055, 1098 may comprise at least 20 mm and/or any combination thereof. the threads 510 may be adapted for cancellous and/or cortical bone. The fixation screw 35, 595, 1075 may further comprise a diameter 540, the diameter 540 may include a range of 2 mm to 6 mm; it may include a range of 2 mm to 4 mm; and/or it may include a range of 2 mm to 3 mm. The diameter 540 may further include a diameter of at least 2 mm; it may include a diameter of at least 3 mm; and/or it may include a diameter of at least 4 mm. The fixation screws 35, 595, 1075 may comprise a material, the material may include a polymer, a metal and/or a ceramic.

FIGS. 15A-15D depicts various plan views of one embodiment of a drill wire 40. The drill wire 40 is used to create successful penetration of the bone for proper fracture fixation using fixation screws 35. The drill wire 40 comprises a solid cylindrical shape. The drill wire 40 may further comprise one or more markers 545a, 545b, a first end 555 and a second end 560. The one or more markers 545a, 545b may be positioned at any location along a length of the drill wire 40. The one or more markers 545a, 545b may be positioned between the first end 555 and the second end 560. The one or more markers 545a, 545b may surround the entire diameter of the drill wire 40 and/or at least a portion of the diameter of the drill wire 40. The one or more markers 545a, 545b may include radiopaque markers and/or laser depth markers. The one or more markers 545a, 545b may match or substantially match the one or more markers 530a, 530b disposed on the fixation screw 35. At least a portion of the first end 555 may be inserted into a driver tool 20.

The drill wire 40 further comprises a bone penetrating tip 550. The bone penetrating tip 550 comprises at least three or four facets. Other bone penetrating tips may be contemplated, including Kirschner wire (K-wire) tips, trocar tips, diamond tips, a fluted-twist tip, and/or any combination thereof. The bone penetrating tip 550 may comprise a rake angle. The rake angle may include a large rake angle decreases the insertional force required to penetrate the bone. The rake angle may include at least 15 degrees or more. In one exemplary embodiment, the drill wire comprises a trocar tip. The trocar tip allows for positive engagement and drilling on the curved outer surfaces of the bones (i.e., metacarpals or radial bones along coronal ridge). The drill wire 40 may include any drill wire known in the art to facilitate and/or produce holes for securing fixation screws 35, 595, 1075 and support the external fixator assembly 30, 570, 1140.

Figure 16:
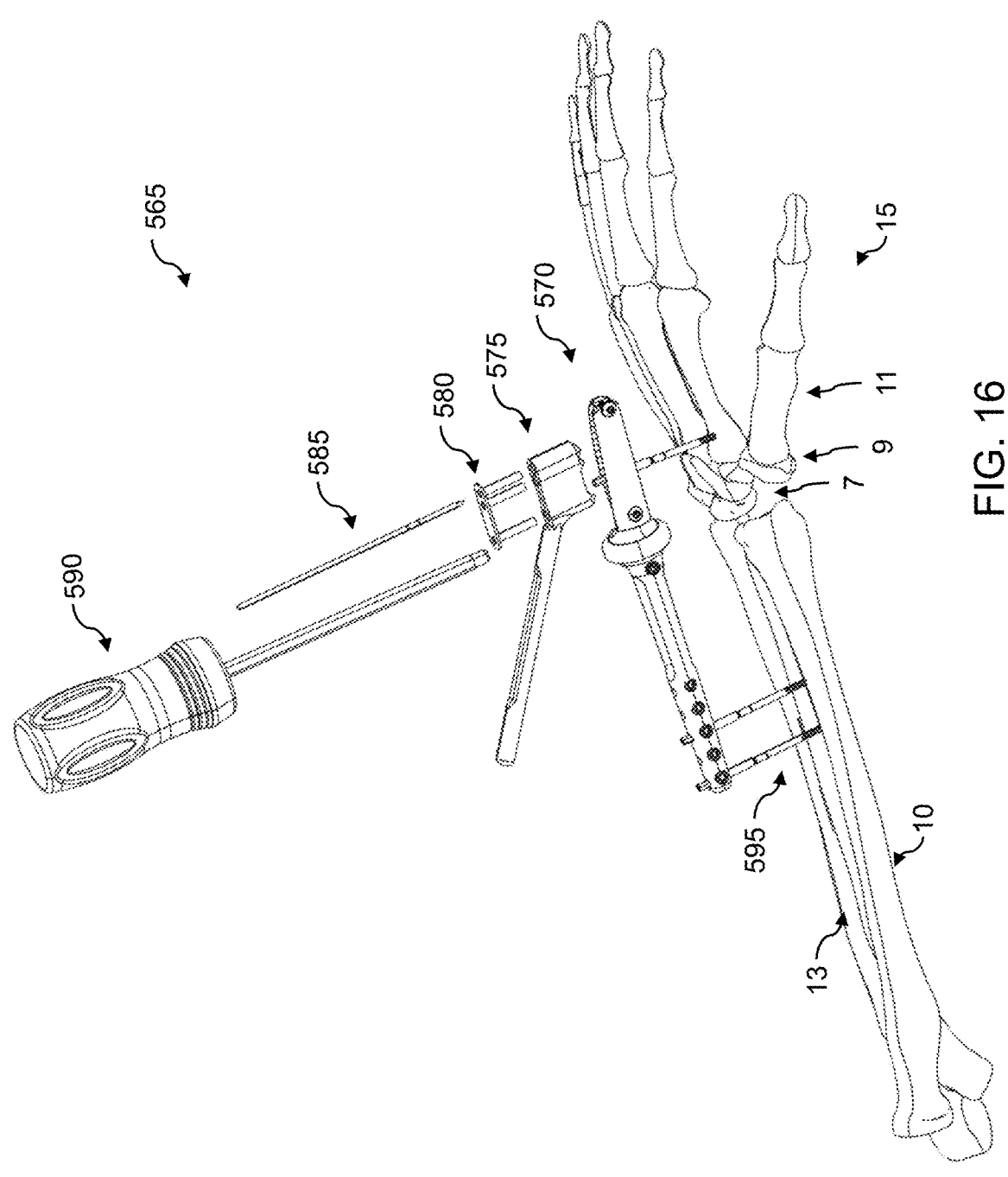
FIG. 16 depicts an isometric view of an alternate embodiment of an external fixator system.

FIG. 16 depicts an isometric view of alternate embodiment of an external fixator system 565. The external fixator system 565 comprises the external fixator assemblies 570, 1140 and at least two fixation screws. The external fixator system 565 may further comprise at least one or more guide tools, driving tools, and drill wires, and/or any combination thereof.

Figures 17A, 17B:
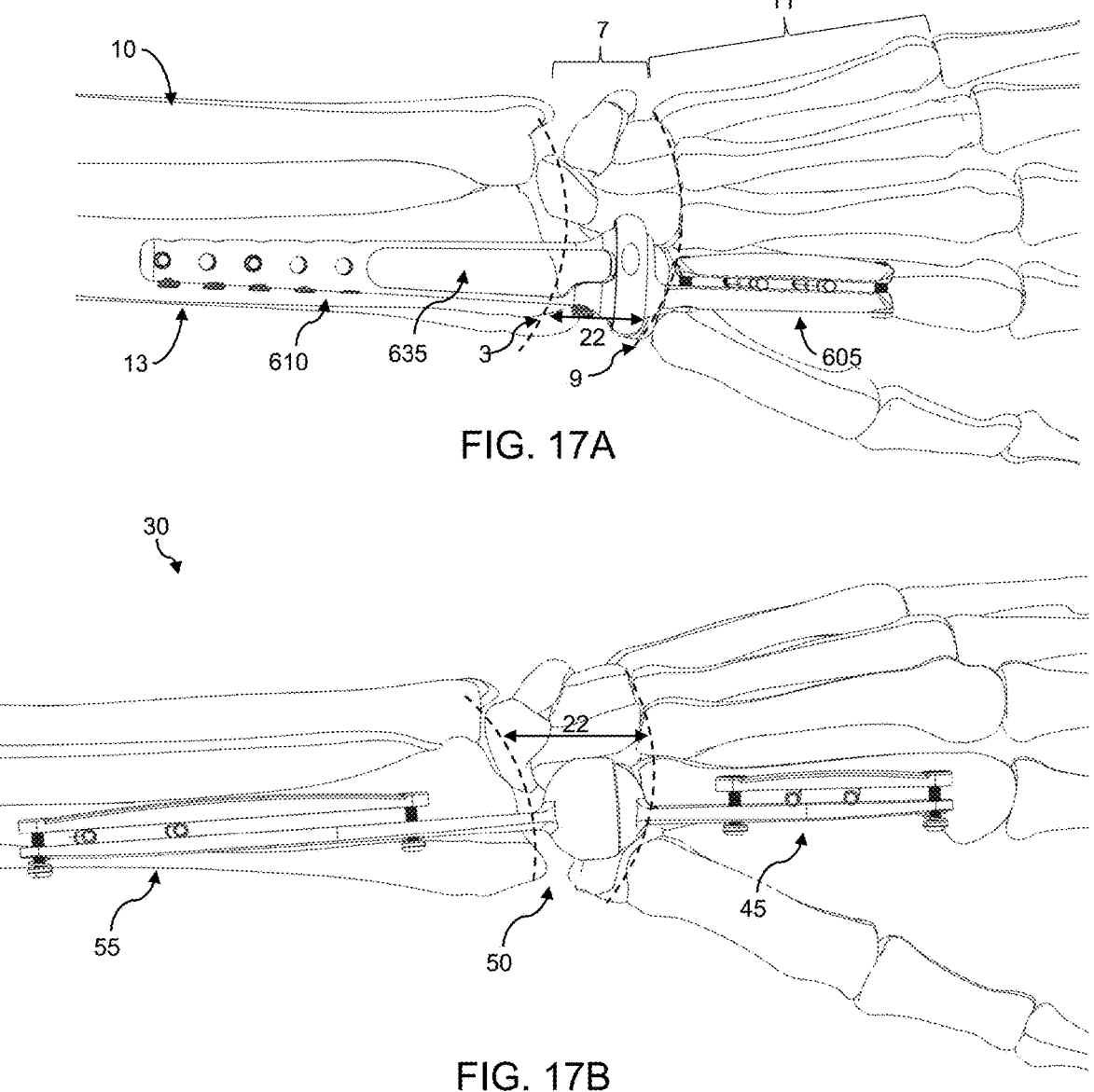
FIGS. 17A-17B depicts two embodiments of the external fixator assembly on a bone model.
Figures 18A, 18B:
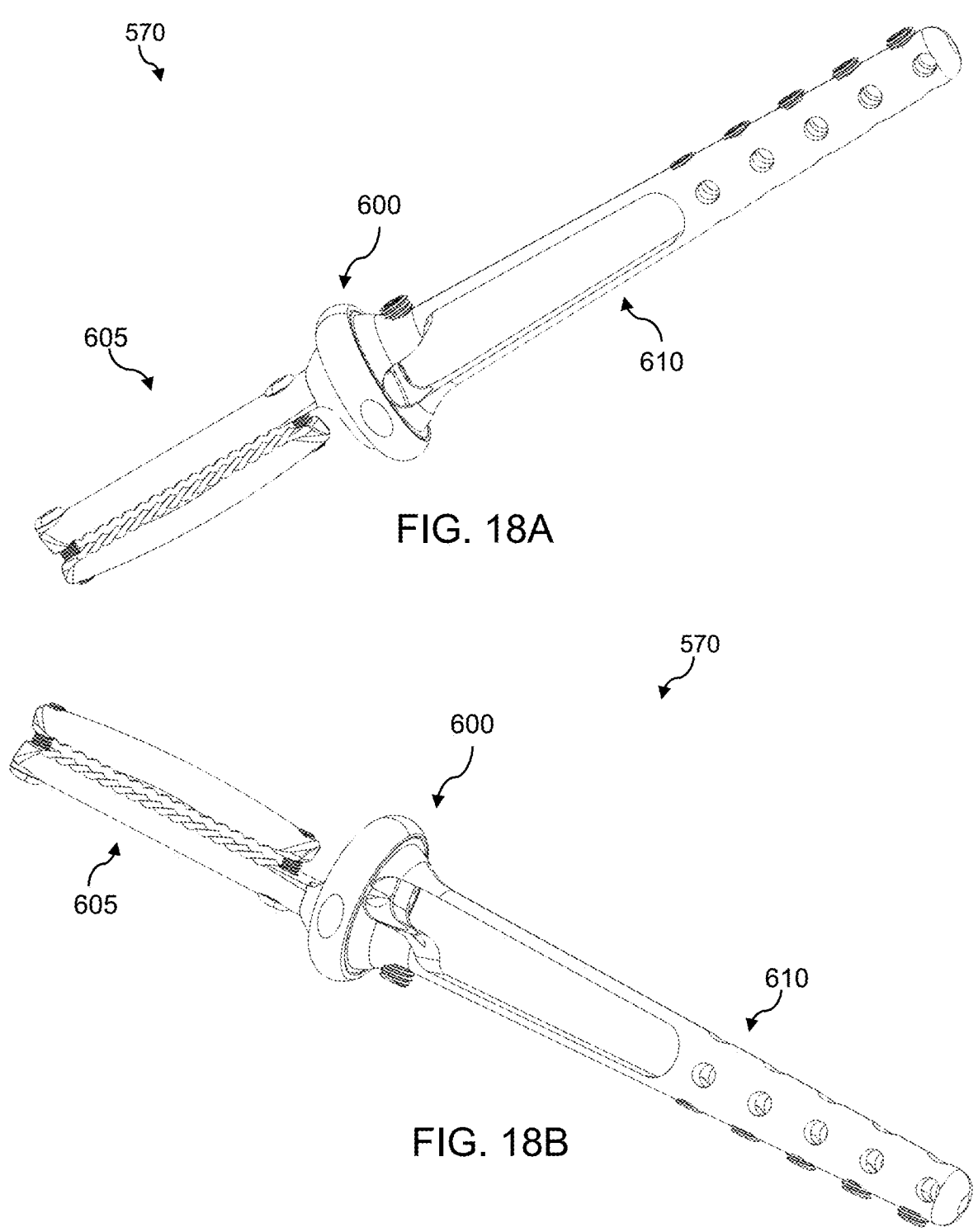
FIGS. 18A-18J depicts various plan views of the alternate embodiment of an external fixator assembly.
Figures 18C, 18D, 18E, 18F:
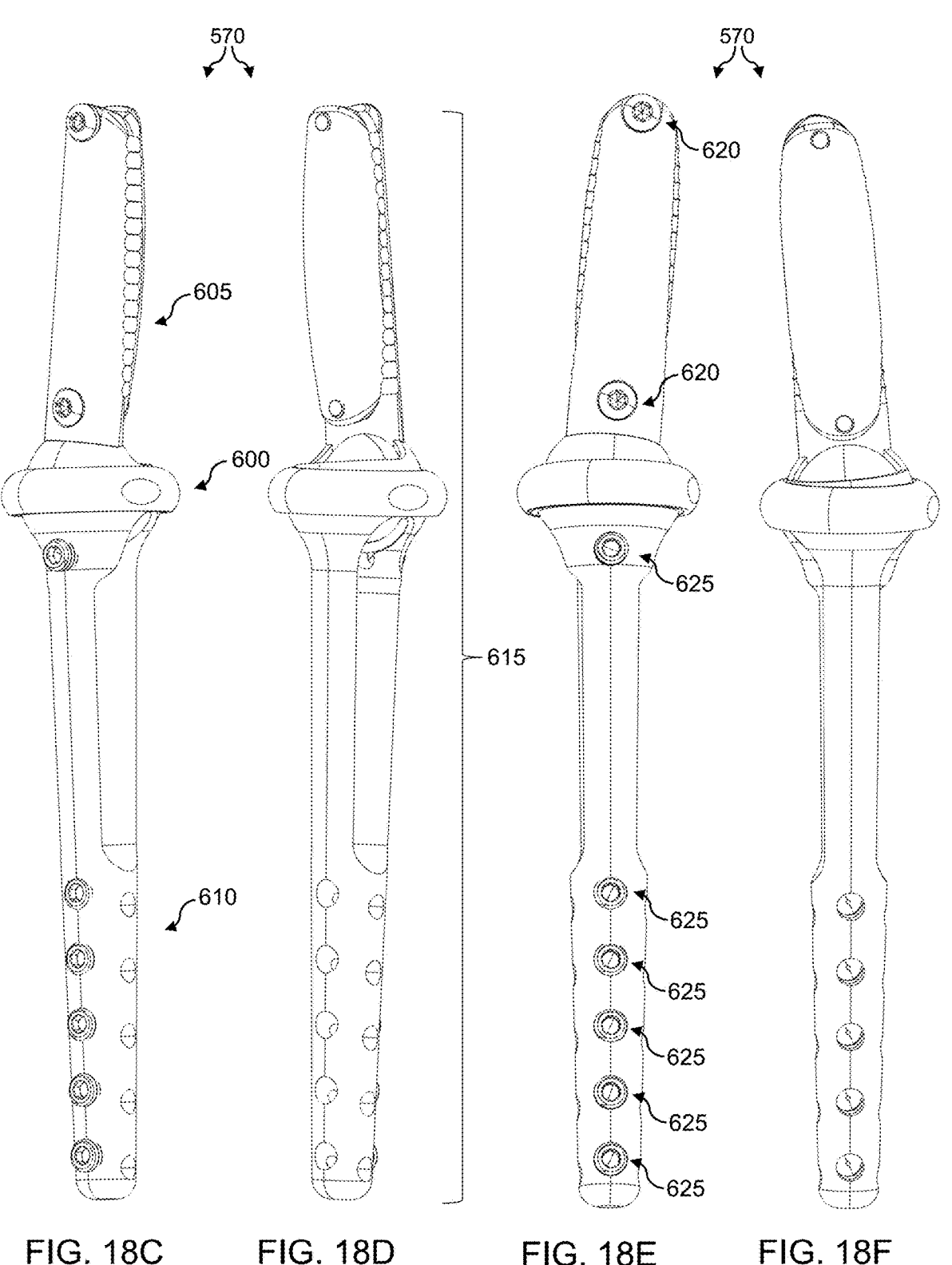
Figures 18G, 18H, 18I, 18J:
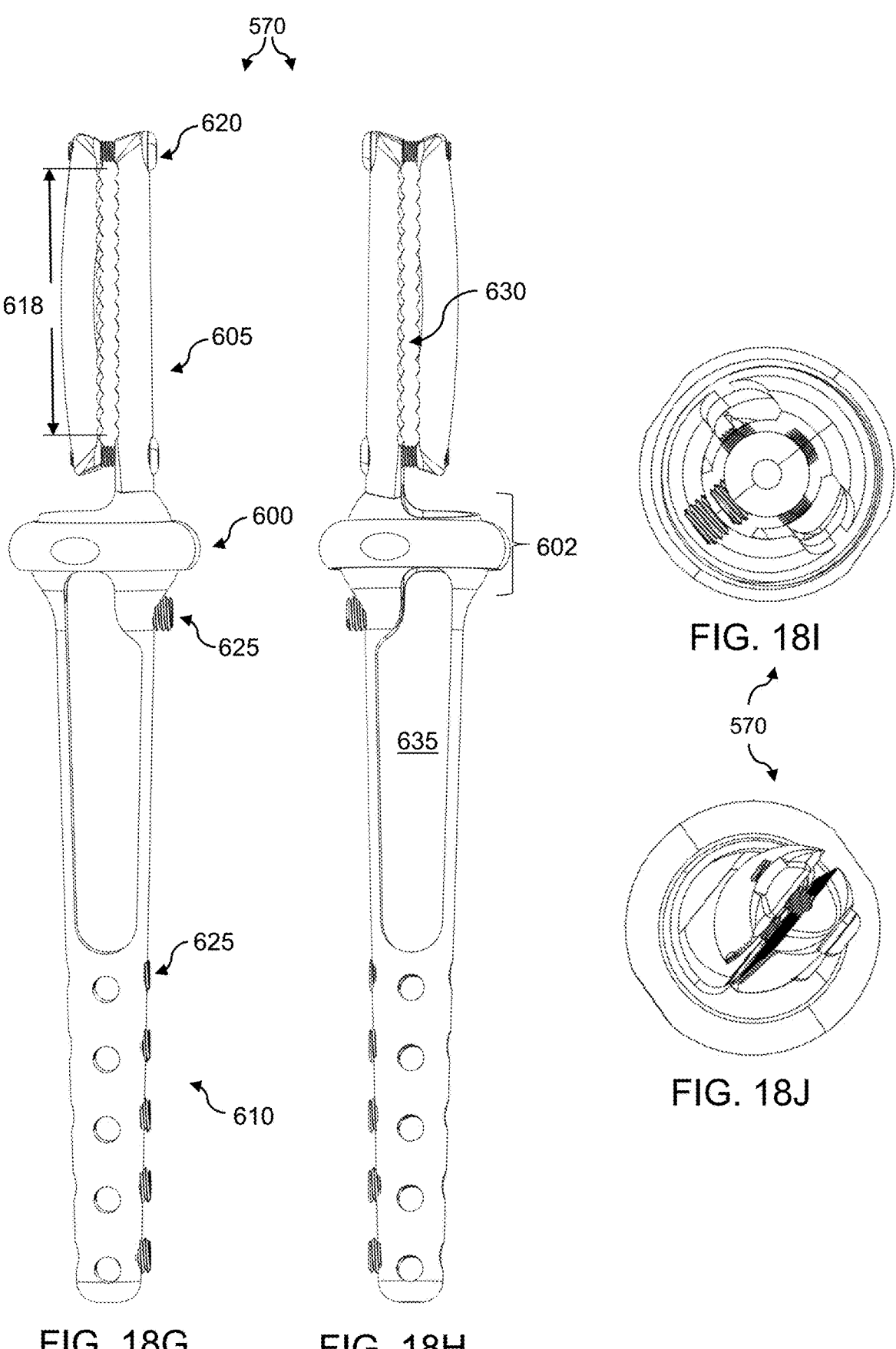
Figure 19:
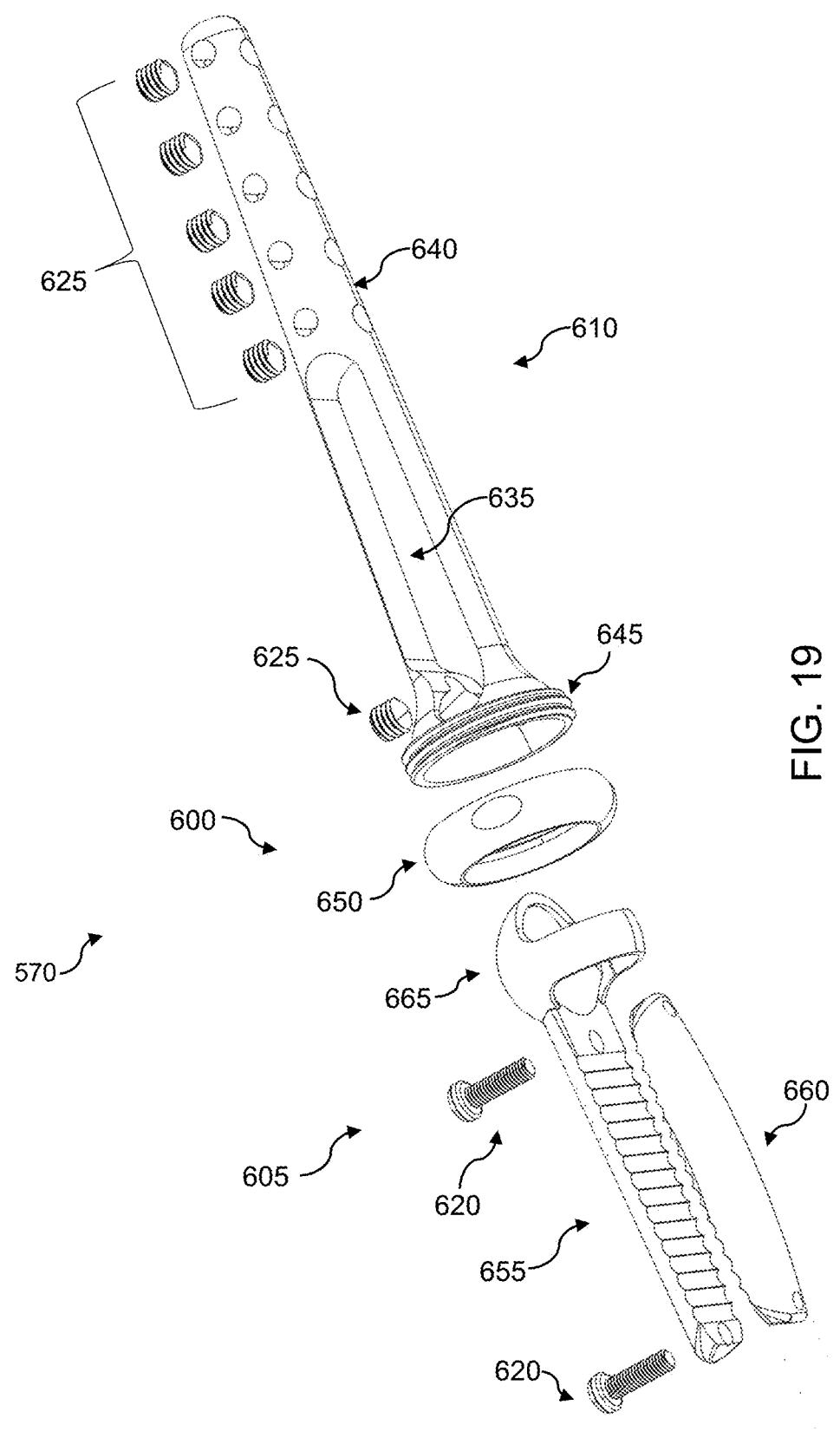
FIG. 19 depicts an exploded view of alternate embodiment of an external fixator assembly.

FIGS. 17A-17B depicts two embodiments of the external fixator assemblies 30, 570 on a bone model to illustrate the low profile and enhanced ergonomics for improved patient comfort. Although, only two embodiments of the external fixator assemblies 30, 570 are shown, the characteristics described below also describe the third embodiment of the external fixator assembly 1140. Each of the external fixator assemblies 30, 570, 1140 is lightweight, compact and without sharp protrusions. Each of the external fixator assemblies further reduces the total number of components needed for the surgical technique.

Furthermore, each of the external fixator assemblies 30, 570, 1140 may comprise enhanced visualization features. The enhanced visualization features allow for visualization of the fracture size, radiocarpal joint 3, the fracture reduction and/or bony alignment during healing. In one embodiment, the enhanced visualization feature may comprise a translucent or radiotransparent material or substantially translucent or radiotransparent material. The translucent or radiotransparent material would allow radiation or X-rays to pass more freely through the external fixator assemblies 30, 570, 1140 during imaging, resulting in the appearance black features on the exposed film. In other words, a translucent or radiotransparent material or substantially translucent or radiotransparent material should not interfere with the X-ray or radiation itself.

Alternatively, at least one of the external fixator assembly's 30, 570, 1140 visualization features may comprise an opening and/or a window 635, 1225 that allows for visualization of at least a portion of the wrist joint 3, carpals 7, the fracture site, the fracture reduction and/or bony alignment during the operative procedure and healing. At least a portion of the window 635, 1225 is disposed over a portion of the wrist joint 3 and/or fracture site.

Furthermore, at least a portion of the polyaxial joint 50, 600, 1150 is positioned over the carpals 7 to further allow enhanced visualization. The polyaxial joint 50, 600, 1150 comprises a polyaxial joint width 82, 602, 1152. The bone model comprises an average joint distance 22, the average joint difference is defined as the distance between the radiocarpal joint 3 and the carpometacarpal joint 9 and/or the trapeziometacarpal joint for the medial and lateral sides. The polyaxial joint width 82, 602, 1152 is disposed between the radiocarpal joint 3 and the carpometacarpal joint 9 and/or the trapeziometacarpal joint. The polyaxial joint width 82, 602, 1152 comprises a smaller width than the average joint distance 22. In another embodiment, at least a portion of the distal frame assembly 45, 605, 1160 is positioned over at least a portion of the metacarpals 11. The entire distal frame assembly 45, 605, 1160 is positioned over the portion of the metacarpals 11. In another embodiment, at least one end, perimeter, and/or edge of the distal frame assembly 45, 605, 1160, the distal frame 90, 655, 1175 and/or distal bracket 95, 660, 1165 is adjacent or near the carpals 7 or one or more joints. The one or more joints comprise the carpometacarpal joint 9 and/or the trapeziometacarpal joint. In another embodiment, at least one end, perimeter, and/or edge of the distal frame assembly 45, 605, 1160, the distal frame 90, 655, 1175 and/or distal bracket 95,

660, 1165 is adjacent or near the fracture site and/or reduction to prevent obstruction of the fracture or reduction site.

FIGS. 18A-18J, 19, 31A-31B and 32 depict various plan views of two alternate embodiments of an external fixator assemblies 570,1140. Each of the alternate external fixator assemblies 570, 1140 comprises a distal frame assembly 605, 1160, a proximal frame assembly 610, 1145 and a polyaxial or multi-axial joint 600, 1150. The distal frame assembly 605, 1160 comprises a distal frame 655, 1175 and a distal compression bracket 660, 1165. The distal frame assembly 605, 1160 may further comprise fasteners 620, 625, 1170. The proximal frame assembly 610, 1145 comprises a proximal frame 640, 1210. The proximal frame assembly 610, 1145 further comprises fasteners 1230. The polyaxial joint 600, 1150 is positioned between the distal frame assembly 605, 1160 and the proximal frame assembly 610, 1145.

FIGS. 21A-211, 31A-31B and 32 depict various plan views of one embodiment of a proximal frame 640, 1210. The proximal frame 640, 1210 comprises an arm or stem 648, 1245 and socket component 645, 1215. The proximal frame 640,1210 further includes a window 635, 1225 and a longitudinal axis 695. The elongated arm or stem 658,1245 includes a first end 705 and a second end 700. The socket component 645,1215 is disposed or positioned at a first end 705. The proximal stem 658,1245 and/or the proximal frame 640,1210 comprises a shape. The shape may be uniform or non-uniform. The shape includes substantially cylindrical. The shape includes a tapered cylinder, the tapered cylinder has a larger outer diameter adjacent to the first end 705, and a smaller outer diameter adjacent to the second end 700. The shape may further include rounded or spherical surfaces to allow manufacturing of the proximal stem 658,1245 and/or the proximal frame 640,1210 in a single machining step and reduce overall manufacturing costs.

In one embodiment, proximal stem 658,1245 and/or the proximal frame 640,1210 further comprises a window 635, 1225 is disposed between the socket component 645,1215 or the polyaxial joint 50,600,1150 and the second end 700. The window 635,1225 may be disposed between the first end 705 and the second end 700. The window 635, 1225 may be disposed adjacent to the first end 705. The window 635, 1225 extends through the proximal stem 658,1245 and/or the proximal frame 640,1210. The window 635,1225 is positioned along a proximal frame length 735,1250 and/or along the longitudinal axis 695 of the proximal frame 640,1210. The window 635,1225 may be positioned between the first end 705 and the second end 700 along the proximal frame length 735,1250 or longitudinal axis 695 of the proximal frame 640,1210. At least a portion of the window 635,1225 is positioned within the socket component 645,1215 and a portion positioned onto the proximal stem 658,1245. At least a portion of the window 635,1225 extends into the socket component 645,1215.

The window 635, 1225 comprises a length and a width. The length of the window 635,1225 may comprise a length of 1.5 inches or greater and/or 1.7 inches or greater; the length may comprise a range of 1.5 inches to 2 inches; the length may comprise a range of 1.5 inches to 1.75 inches. The width of the window may comprise a width of 0.25 inches or greater and/or 0.30 inches or greater. The width of the window may comprise a width of 0.25 inches to 0.5 inches; and/or the width may comprise 0.30 inches to 0.5 inches. The window 635,1225 removes a portion of the material to further reduce the weight of the external fixator assemblies. By placing a window 30,570,1140 in the distal assembly 45, 605, 1160 and/or the proximal assembly 55,610,1145 is counterintuitive due to the required strength that is required to neutralize the magnitude and physiological loads on the distal radius.

The proximal stem 658,1245 and/or the proximal frame 640,1210 further comprises a plurality of holes or passageways 725,740,1230,1235 and an outer diameter or outer surface. The plurality of holes or passageways 725,740, 1230,1235 are sized and configured to receive a portion of one or more fasteners 625,1230. The one or more fasteners 625,1230 may be used to secure the fixation screws 35,595, 1075 and/or the polyaxial joint 600,1150. The plurality of holes or passageways 725,740,1230,1235 extends through the outer diameter or outer surface. The plurality of holes or passageways 725,740,1230,1235 is transverse to the longitudinal axis 695 of the proximal frame 640,1210 and/or oblique to the longitudinal axis 695 of the proximal frame 640,1210. The plurality of holes or passageways 725,740, 1230,1235 are disposed between the perimeter of the window 635, 1225 and the second end 700. Each of the plurality holes or passageways 625,1230 are spaced apart at a set distance along a longitudinal axis 695 of the proximal frame 640,1210. Each of the plurality holes or passageways 625, 1230 spaced apart at a set distance radially and/or around the outer diameter of the proximal frame 640,1210 and/or the proximal stem 648,1245. Each of the plurality holes or passageways 725,740,1230,1235 are coaxial and spaced apart at a set distance along the longitudinal axis 695 of the proximal frame 640,1210 and radially or around the outer diameter of the proximal frame 640,1210 and/or the proximal stem 648,1245. The set distance along the longitudinal axis may comprise a distance of 0.125 inches to 0.50 inches; the set distance may comprise a distance of 0.25 inches to 0.50 inches; may comprise a distance of 0.35 inches to 0.45 inches. The set distance along the longitudinal axis may further comprise a distance of greater than or equal to 0.25 inches and/or 0.35 inches.

The set distance along the length of the longitudinal axis 695 may comprise a distance that is equal to or greater than 5 mm and/or equal to or greater than 10 mm. The set distance radially or around the outer diameter of the proximal frame 640,1210 or proximal stem 648,1245 may be equal to or greater than 10 degrees and/or equal to or greater than 20 degrees. The plurality of holes or passageways 725,740,1230,1235 may be positioned in repeating rows, each of the repeating rows may be parallel or offset. At least a portion of the plurality of passageways may intersect. At least a portion of the plurality of holes or passageways 725,740,1230,1235 comprises chamfers to help align the fixation screws 35,595,1075. At least a portion of the plurality of holes or passageways 725,740,1230,1235 comprises threads.

In another embodiment, the proximal stem 658,1245 and/or the proximal frame 640,1210 further comprises a first plurality of holes or passageways 725,1230 and a second plurality of holes or passageways 740,1235. The first plurality of holes or passageways 725,1230 and a second plurality of holes or passageways 740,1235 are sized and configured to receive a portion of one or more fasteners 625,1230. The one or more fasteners 625,1230 may be used to secure the fixation screws 35,595,1075 and/or the polyaxial joint 600,1150. The first plurality of holes or passageways 725,1230 are disposed onto the proximal frame 640,1210 and/or the proximal stem 648,1245 and align along the longitudinal axis 695. The second plurality of holes or passageways 740,1235 are disposed onto the proximal frame 640,1210 and/or the proximal stem 648,1245 and align along the longitudinal axis 695. The first plurality of holes or passageways 725,1230 comprise a first plurality of holes axis (not shown) and the second plurality of holes or passageways 740,1235 comprise a second plurality of holes axis (not shown). At least one of the first plurality holes axis and at least one of the second plurality of holes axis are transverse to the longitudinal axis 695 of the proximal frame 640,1210. Alternatively, each of the first plurality holes axis and each of the second plurality of holes axis are transverse to the longitudinal axis 695 of the proximal frame 640,1210. At least one of the first plurality holes axis and at least one of the second plurality of holes axis intersect. Each of the first plurality holes axis and each of the second plurality of holes axis intersect. At least portion of the first plurality holes 725,1230 and/or at least a portion of the second plurality of holes 740,1235 comprise a chamfer. At least portion of the first plurality holes 725,1230 and/or at least a portion of the second plurality of holes 740,1235 comprise threads.

In another embodiment, the proximal stem 658,1245 and/or the proximal frame 640,1210 further comprises a first hole or passageway row 725,1230 and a second hole or passageway row 740,1235. The first hole or passageway row 725,1230 comprises a first plurality of holes or passageways and second hole or passageway row 740,1235 comprises a second plurality of holes or passageways. The first holes or passageway row 725,1230 are disposed onto the proximal frame 640,1210 and/or the proximal stem 648,1245 and align along the longitudinal axis 695. The second holes or passageway row 740,1235 is disposed onto the proximal frame 640,1210 and/or the proximal stem 648,1245 and align along the longitudinal axis 695. The first plurality of holes or passageways 725,1230 comprise a first plurality of holes axis (not shown) and the second plurality of holes or passageways 740,1235 comprise a second plurality of holes axis (not shown). At least one of the first plurality holes axis and at least one of the second plurality of holes axis are transverse to the longitudinal axis 695 of the proximal frame 640,1210. Alternatively, each of the first plurality holes axis and each of the second plurality of holes axis are transverse to the longitudinal axis 695 of the proximal frame 640,1210. At least one of the first plurality holes axis and at least one of the second plurality of holes axis intersect. Each of the first plurality holes axis and each of the second plurality of holes axis intersect.

The first plurality of holes or passageways 725,1230 and/or second plurality of holes or passageways 740,1235 are sized and configured to receive a portion of one or more fasteners 35, 595, 1075. The first plurality of holes or passageways 725,1230 and/or second plurality of holes or passageways 740,1235 may be disposed between the perimeter of the window 635,1225 and the second end 700. At least a portion of the first plurality holes 725,1230 and/or at least a portion of the second plurality of holes 740,1235 comprise a chamfer. At least a portion of the first plurality holes 725,1230 and/or at least a portion of the second plurality of holes 740,1235 comprise threads.

In another embodiment, the proximal stem 658,1245 and/or the proximal frame 640,1210 further comprises a locking fastener opening and/or one or more locking fastener openings 720,1240. The one or more locking fastener openings 720,1240 is sized and configured to receive a locking fastener 625,1230. The locking fasteners 625,1230 may comprise set screws. The one or more locking fastener openings 720,1240 are disposed adjacent and/or proximate to the first end 705 of the proximal stem 658,1245 and/or the proximal frame 640,1215. The one or more locking fastener openings 720,1240 is disposed into or onto the socket component 645,1215. The one or more locking fastener openings 720,1240 (see FIGS. 20A-20C, 31A-31B and 32) extend into the socket component 645,1215. The one or more locking fastener openings 720,1240 are transverse and/or oblique to the longitudinal axis 695 of the proximal stem 658,1245 and/or the proximal frame 640,1215. The one or more locking fastener openings 720,1240 is disposed around the socket component 645,1215 symmetrically or asymmetrically. At least a portion of one or more locking fastener openings 720,1240 are disposed diametrically opposite to each other. At least a portion of one or more locking fastener openings 720,1240 are disposed on a bottom surface of the socket component 645,1215 and extends towards the top surface of the socket component 645,1215. At least a portion of the one or more locking fastener openings 720,1240 comprises threads.

Figures 20A, 20B, 20C:
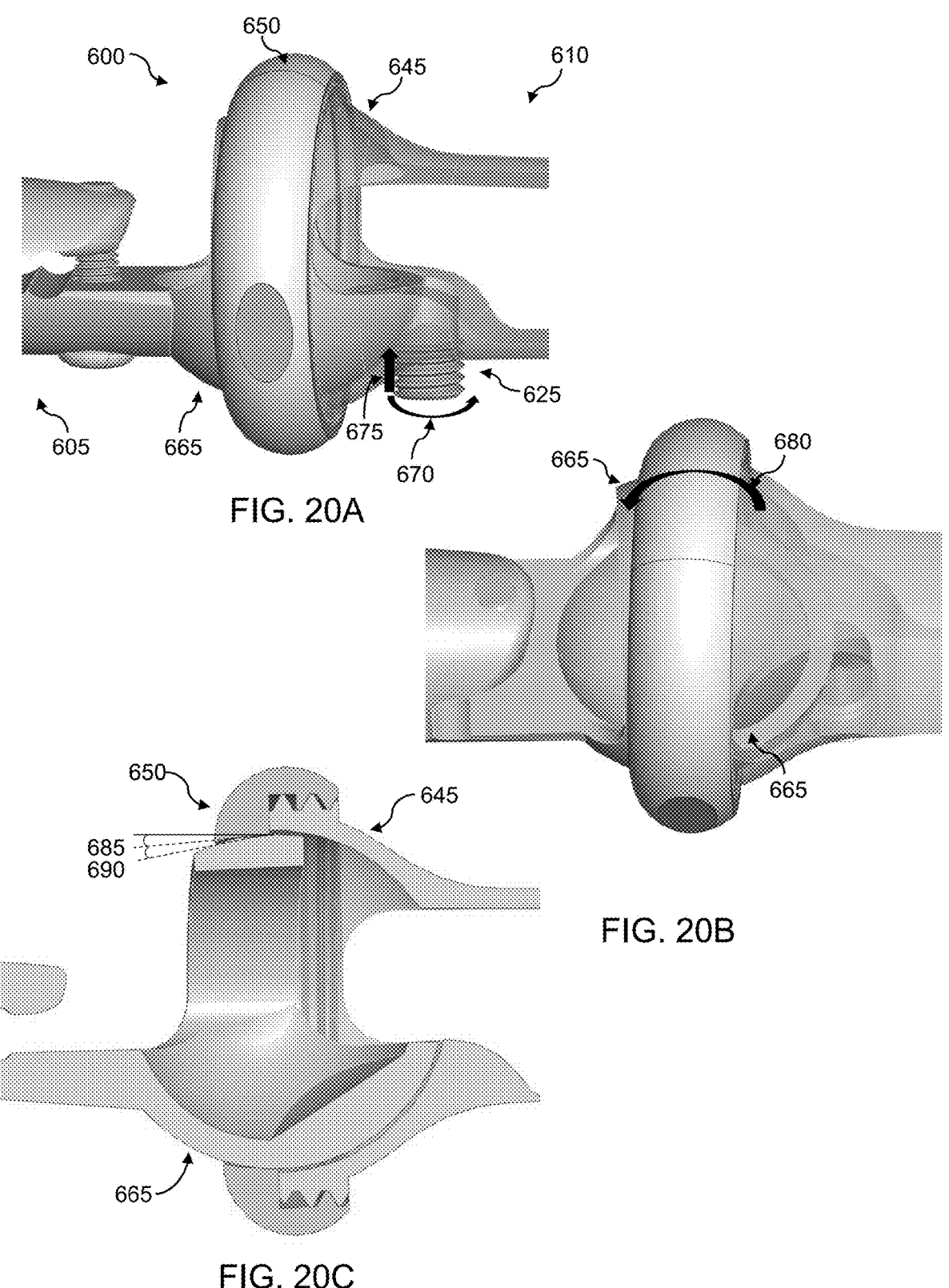
FIGS. 20A-20C depicts isometric views of an alternate embodiment of the lockable polyaxial joint of the external fixator assembly.
Figures 21A, 21B, 21C, 21D:
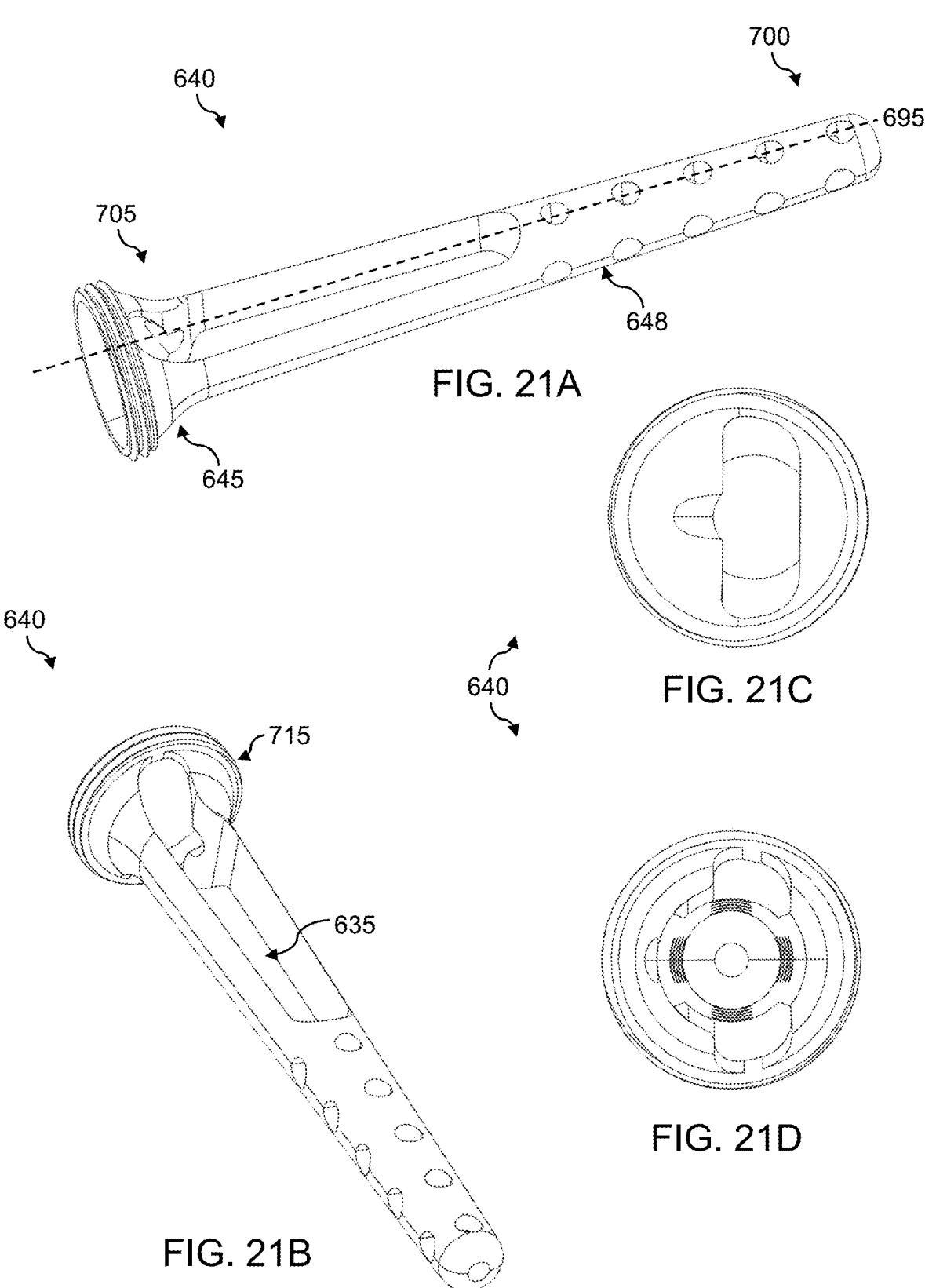
Figures 21E, 21F, 21G:
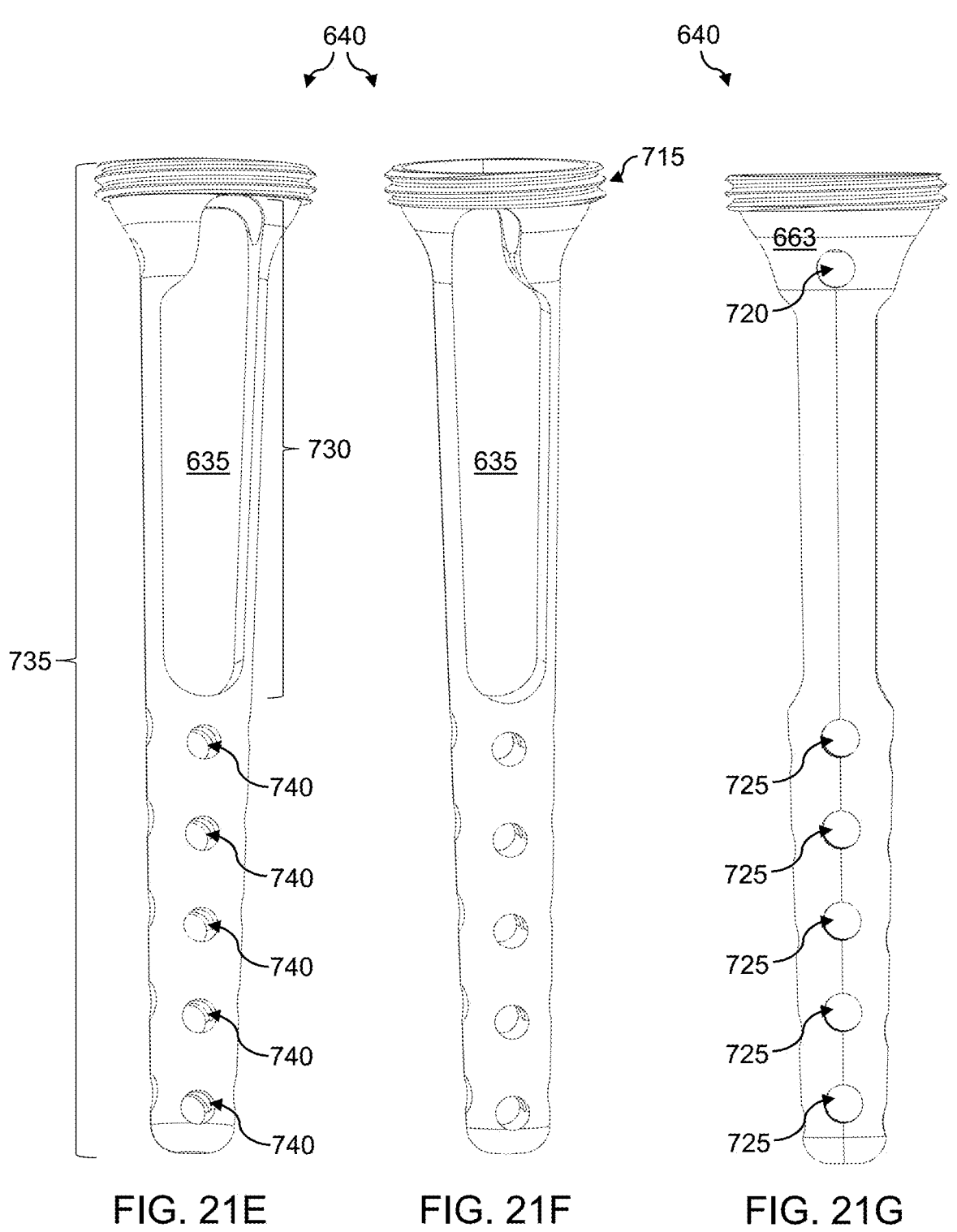
Figure 22E:
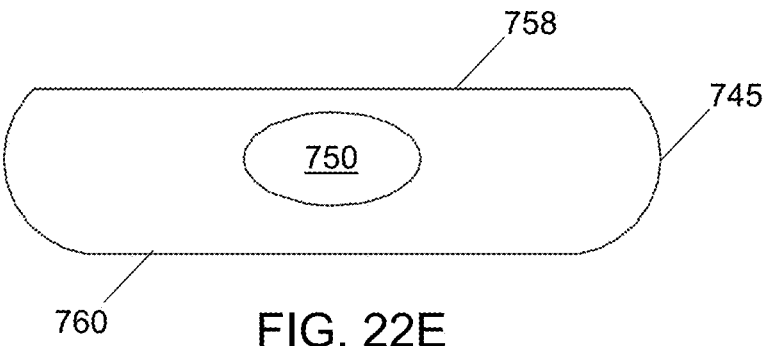
Figure 22F:
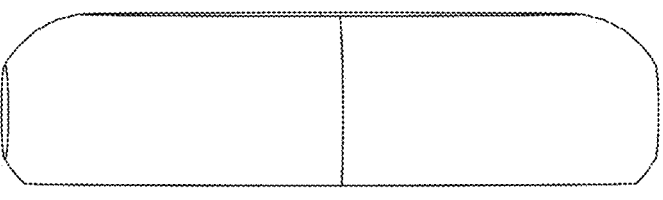
Figure 22G:
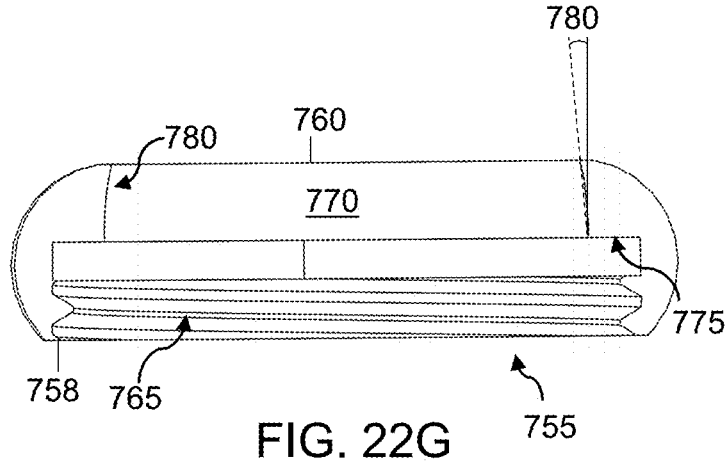
FIG. 22G depicts a cross-section view of the locking collar of FIGS. 22A-22F.
Figures 23A, 23B:
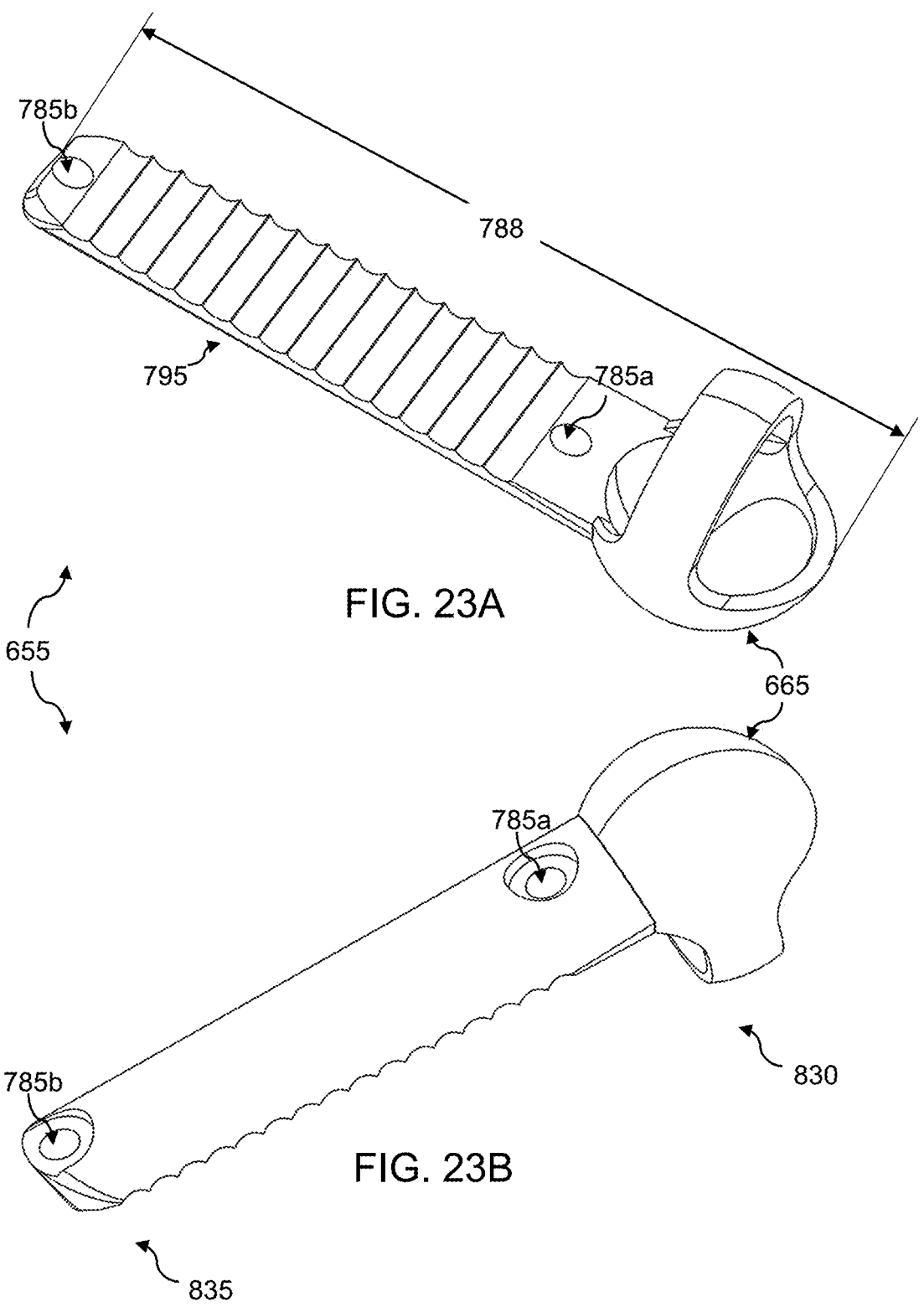
FIGS. 23A-23I depicts various plan views of an alternate embodiment of a distal frame.
Figures 23C, 23D, 23E:
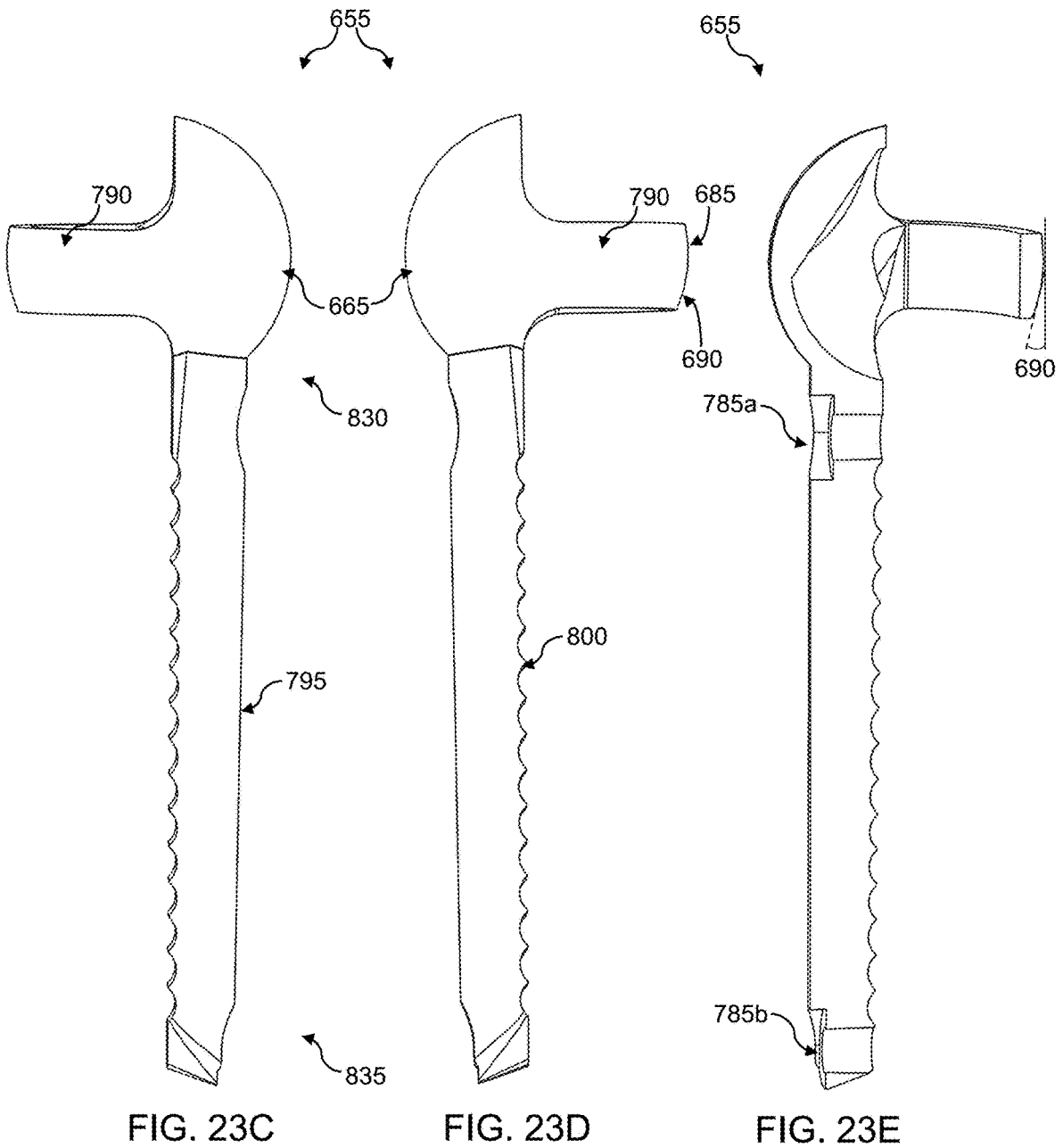
Figures 23F, 23G, 23H, 23I:
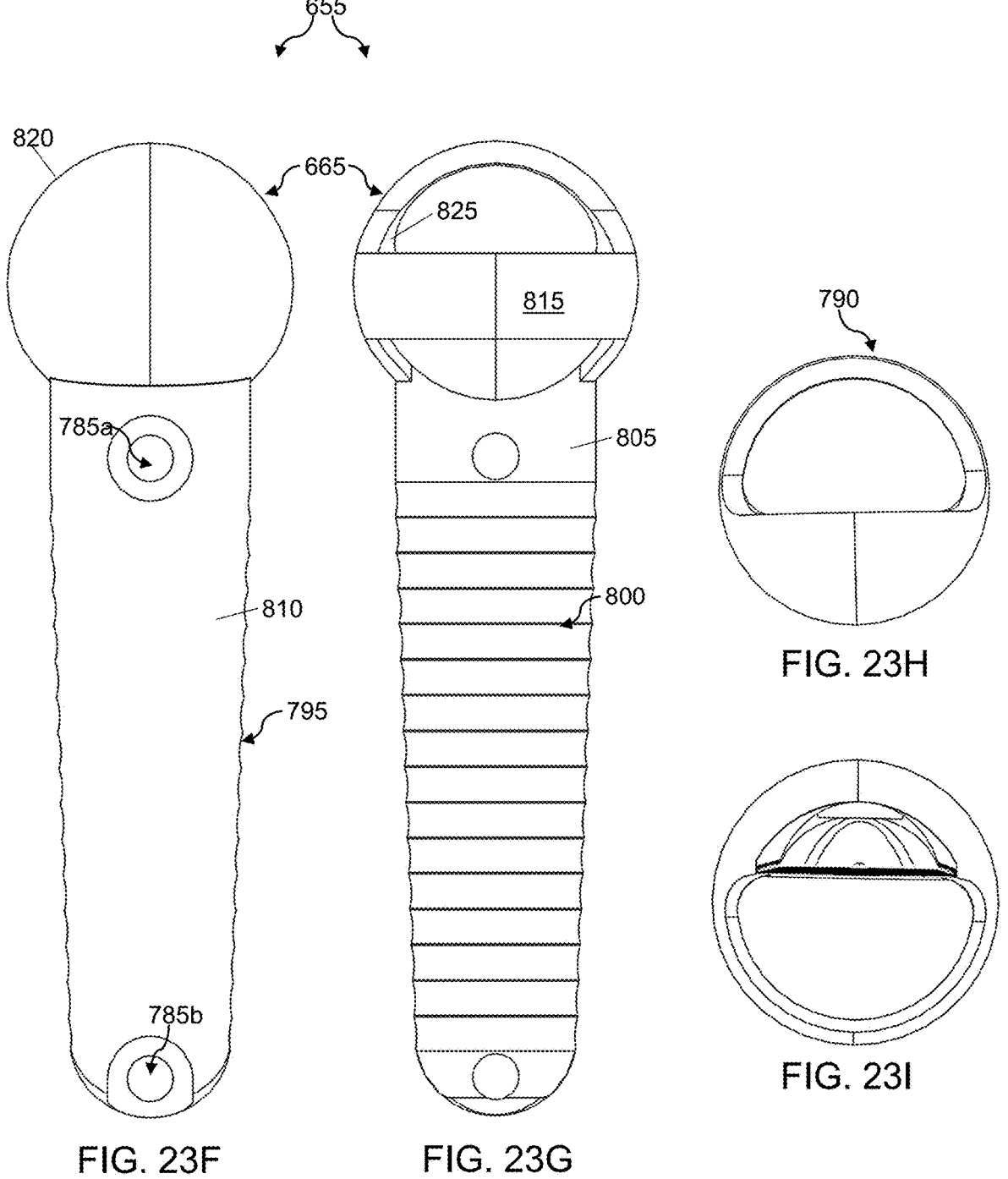
Figures 24A, 24B:
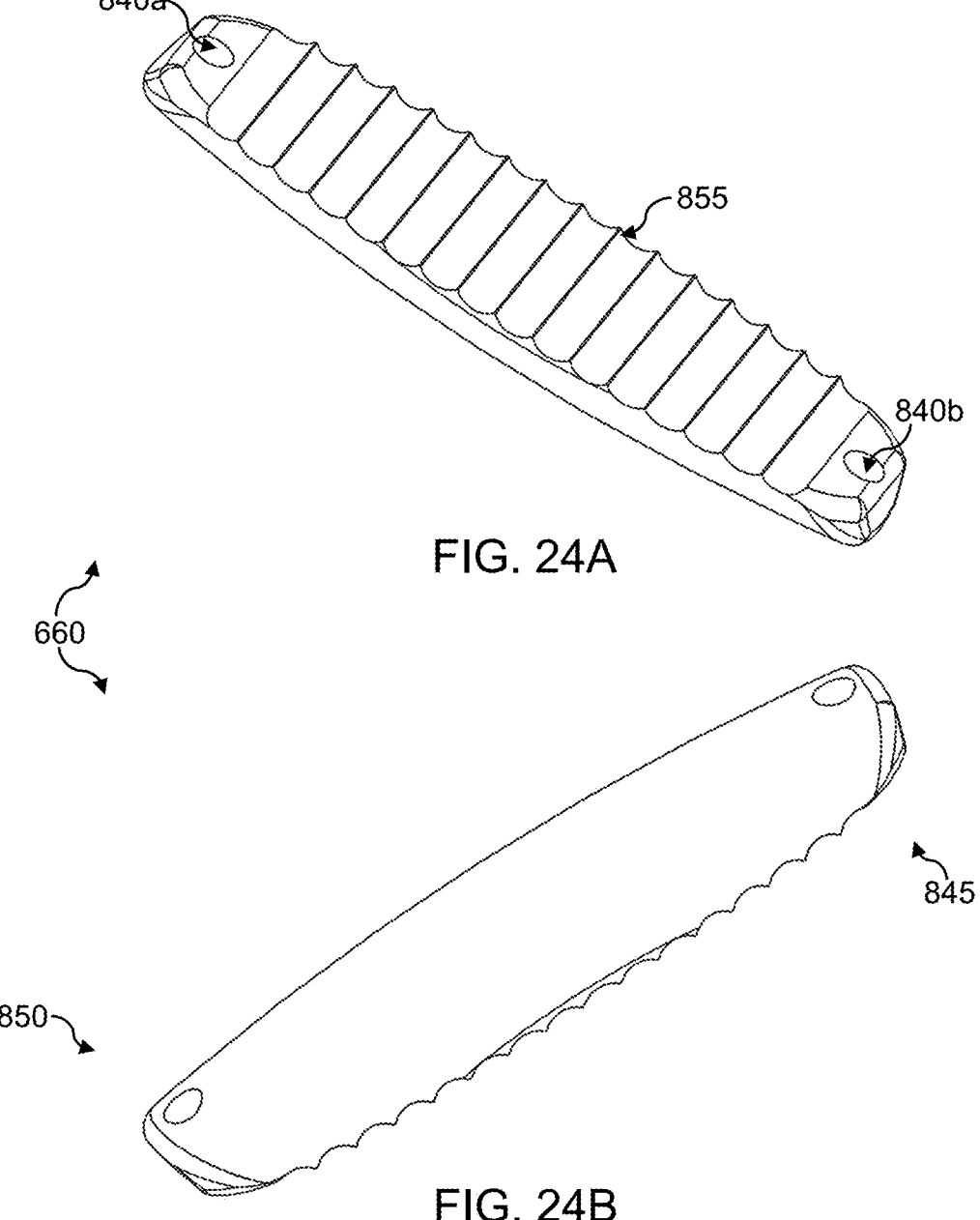
FIGS. 24A-24G depicts various plan views of an alternate embodiment of a distal compression bracket.
Figure 24C:
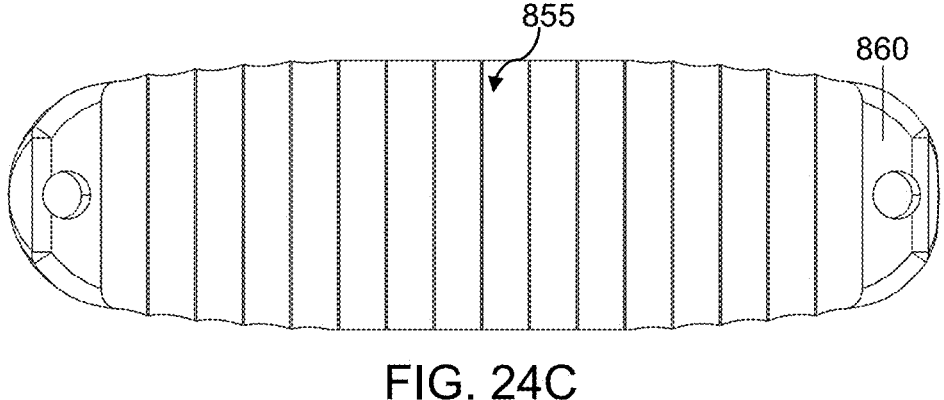
Figure 24D:
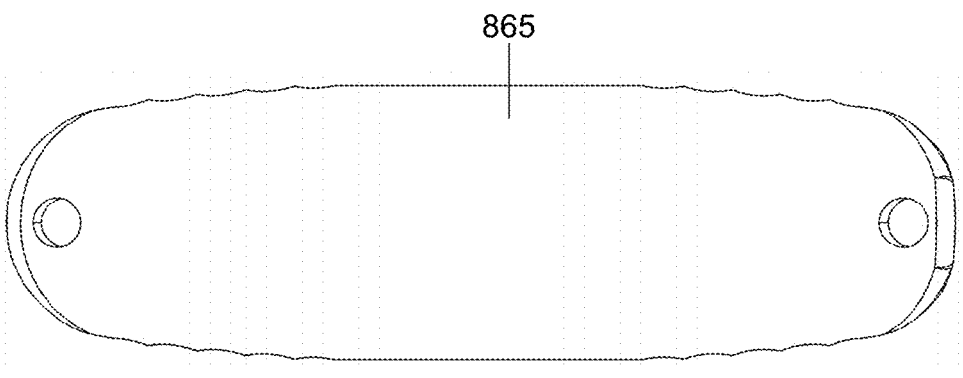
Figure 24E:
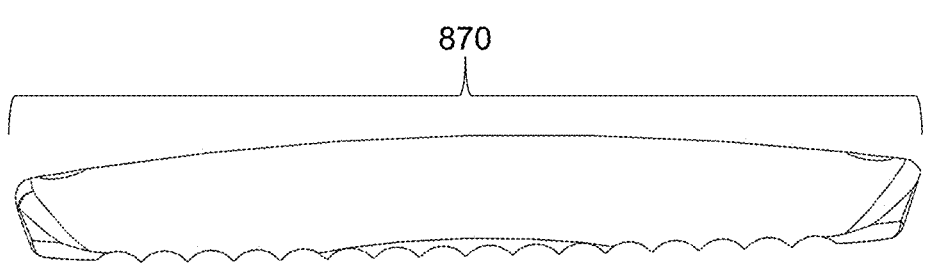
Figure 24F:
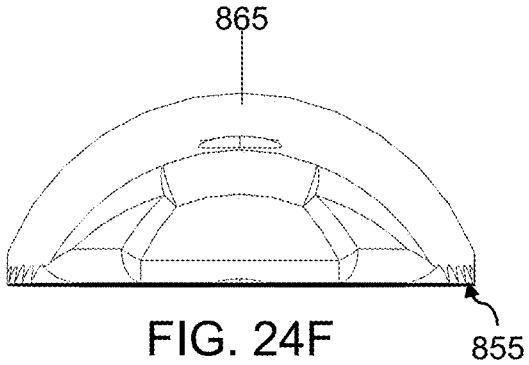
Figure 24G:
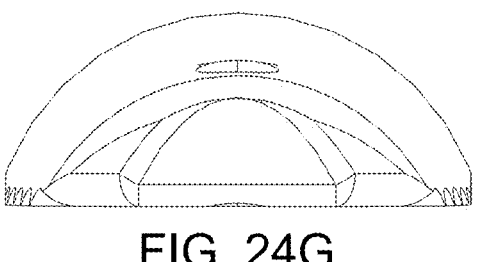
Figure 24H:
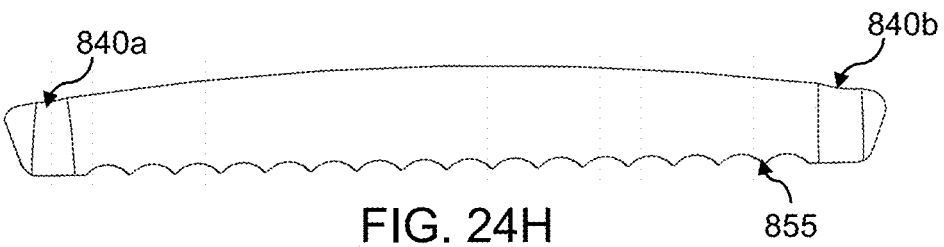
FIG. 24H depicts a cross-sectional view of the distal compression bracket of FIG. 24E.

In one embodiment, the one or more locking fasteners 625,1230 may facilitate the securement of the polyaxial joint 600,1150 by wedging the ball component 665,1180 into the socket component 645,1215 as shown in FIGS. 20A-20C. As the one or more locking fasteners 625,1230 are rotated 670, the one or more locking fasteners 625,1230 vertically translates 675 along the vertical axis of the one or more locking fastener openings 720,1240 and pushes on the outer diameter and/or outer surface 820,1185 of the ball component 665,1180. The pushing of the outer diameter or outer surface 820,1185 of the ball component 665,1180 exerts a force the ball component 665,1180 to rotate, slide or translate radially 680 relative to the socket component 645,1215 until a portion of the ball component 665,1180 and/or at least a portion of the bridge 790 engages a portion of the locking collar 650 and/or an inner surface of the locking collar 650. The locking collar 650 includes an inner surface, at least a portion of the inner surface includes a flat surface and/or a tapered angled surface 685 that interferes with the rotation, sliding or translation 680 of the ball component 665, 1180 relative to the socket component 645,1215 and causes an increase of friction to restrict or eliminate any polyaxial translational motion. Accordingly, the bridge 790 includes an outer surface that comprises an angled surface 690 that also helps interfere with rotation, sliding or translation 680 of the ball component 665,1180 relative to the socket component 645,1215. The tapered angled surfaces 685,690 includes a morse taper angle, the angle includes at least 5 degrees or greater. Alternatively, the angle includes at least 5 degrees to 20 degrees.

The outer diameter or the outer surface of the proximal stem 658,1245 and/or the proximal frame 640,1210 may further comprise a surface finish (not shown) or protrusions. The protrusions may comprise threads, flutes, grooves, and/or teeth that may include various shapes. The various shapes may include tapered, stepped, conical and/or paralleled, flat, pointed, and/or rounded. The surface finishes may further comprise roughened surfaces or porous surfaces, including turned, blasting, sand blasting, acid etching, chemical etching, dual acid etched, plasma sprayed, anodized surfaces, and/or any combination thereof. The surface finishes may further include a polish surface finish or texture. Alternatively, at least a portion of the outer diameter and/or outer surface of the proximal stem 658,1245 and/or the proximal frame 640,1210 may comprise a surface finish or protrusions.

The proximal stem 658,1245 and/or the proximal frame 640,1210 may further comprise a socket component 645, 1215. The socket component 645,1215 is disposed at a first end 705 of the proximal stem 658,1245 and/or the proximal frame 640,1210. The socket component 645,1215 extends outwardly from the first end 705 of the proximal stem 658,1245 and/or the proximal frame 640,1210. The socket component 645,1215 comprises an outer surface 663,1260, and inner surface 653,1265, and one or more notches. The inner surface 653,1265 of the socket component 645,1215 contacts and slidably engages with the outer diameter or outer surface 820,1185 of the ball component 665,1180 to create a polyaxial joint 600, 1150 with polyaxial motion. The one or more notches extends along the inner surface 653, 1265 of the socket component 645,1215. The one or more notches or channels are sized and configured to receive one or more fasteners 625,1230.

The socket component 645,1215 and/or the inner surface 653,1265 of the socket component 645,1215 further comprises a shape. The shape of the socket component 645,1215 and/or inner surface 653,1265 may be uniform or non-uniform. The shape may comprise a hemisphere and/or sphere. The shape may further include a concave or arch shape. Furthermore, at least a portion of the outer surface 663,1260 and inner surface 653,1265 of the socket component 645,1215 may comprise a surface finish (not shown) or protrusions (not shown). The protrusions may comprise threads, flutes, grooves, and/or teeth that may include various shapes. The surface finishes may further comprise roughened surfaces or porous surfaces, including turned, blasting, sand blasting, acid etching, chemical etching, dual acid etched, plasma sprayed, anodized surfaces, and/or any combination thereof. The surface finishes may further include a polish surface finish or texture. Furthermore, the socket component 645,1215 and/or proximal frame 640, 1210 may further comprise threads 715,1220. The threads 715,1220 are disposed on the outer surface 663,1260 of the socket component 645,1215. The threads 715,1220 are designed and configured to receive a locking collar 650, 1205. The threads 715,1220 may be course or fine threads.

FIGS. 22A-22G, 31A-31B and 32 depict various plan views of alternate embodiments of a locking collar 650, 1205. The locking collar 650,1205 comprises an outer diameter or outer surface 745, an inner surface 755, a bottom surface 758 and a top surface 760. The outer diameter or outer surface 745 is generally or substantially cylindrical. The outer diameter or outer surface 745 comprises one or more ergonomic features 750. The one or more ergonomic features 750 allows the surgeon to effectively grip, hold and/or utilize the product properly. The one or more ergonomic features 750 comprises a flat surface and/or a surface finish or surface texture. The surface finish may comprise protrusions, roughened surface or polished surface finish. The protrusions may comprise threads, flutes, grooves, and/or teeth that may include various shapes. The roughened surfaces finishes may comprise turned, blasting, sand blasting, acid etching, chemical etching, dual acid etched, plasma sprayed, anodized surfaces, and/or any combination thereof. The one or more ergonomic features 750 may be disposed onto the outer diameter or outer surface 745 of the locking collar 650,1205. The one or more ergonomic features 750 may be positioned radially around the circumference of the outer diameter and/or outer surface 745 of the locking collar 650,1205 at a set distance. The set distance may be symmetrical or asymmetrical. The set distance may be at least 180 degrees apart.

The locking collar inner surface 755 may further comprise a first portion 770 and a second portion 765. The second portion 765 may comprise threads. The threads are sized and configured to be disposed and engage with the threads 715,1220 of the socket component 645,1215 of the proximal frame 640,1210. The locking collar 650,1205 is rotated over the threads 715,1220 of the socket component 645,1215 of the proximal frame 640,1210. The second portion 765 comprises a second diameter. The first portion 770 may comprise an angled or radiused surface 780. The taper angle, angled surface and/or radiused surface 780 may comprise a morse taper angle. The taper angle includes at least 5 degrees or greater and/or at least a range of 5 degrees to 20 degrees. The first diameter of the first portion 770 is smaller than the second diameter of the second portion 765. The first portion 770 further comprises shelf 775 that contacts and/or engages with a top surface of the socket component 645 of the proximal frame 640,1210 to stop translation—providing tactile feedback to the surgeon for tightening. The first portion 770 may be sized and configured to receive a portion of the ball component 665,1180 of the distal frame 655,1175. Alternatively, the angled and/or tapered surface includes an angle of at least 5 degrees to 20 degrees.

FIGS. 16, 18A-18J, 19, 31A-31B and 32, depict multiple embodiments of a distal frame assembly 605,1160. In one embodiment, the external fixator system 5, 565 comprises a distal frame assembly 605,1160. The distal frame assembly 605,1160 facilitates translation at a translation distance of the one or more fixation screws 35,595,1075 within an elongated opening 618,1300 as shown in FIGS. 5A-5C, 18G. The translation distance may comprise a distance of 1.25 inches or greater and/or 1.5 inches or greater. The distal frame assembly 605,1160 secures the one or more fixation screws 35,595,1075 into a bone position. The distal frame assembly 605,1160 is disposed over the metacarpals 9 and/or portion of the metacarpals. The bone position may comprise the metacarpals 9 and/or a least a portion of the metacarpals 9. The distal frame assembly 605,1160 comprises a distal frame 655,1175 and a distal compression bracket 660,1165. The distal frame assembly 605,1160 further comprises one or more fasteners or screws 620,625, 1170,1230.

FIGS. 23A-231, 31A-31B and 32 depict various plan views of alternate embodiments of a distal frame 655,1175. The distal frame 655,1175 comprises a distal arm or stem 795,1255 and a ball component 665,1180. The elongated distal arm or stem 795,1255 includes a first end 830 and a second end 835. The distal frame 655,1175 comprises a first end 830 and a second end 835. The distal stem 795,1255 and/or the distal frame 655,1175 further comprises a first surface 805,1270 and a second surface 810,1275. The distal frame 655,1175 comprises a material, the material may comprise a polymer, a metal and/or a ceramic.

The distal frame 655,1175 and/or the distal arm or stem 795,1255 further comprises at least one opening and/or it comprises one or more openings 785a,785b,1190a, 1190b. The at least one opening and/or the one or more openings 785a,785b,1190a,1190b extend through the first surface 805,1270 and the second surface 810,1275. The one or more openings 785a,785b,1190a,1190b are sized and configured to receive a portion of one or more fasteners 620,625,1170, 1230. The one or more openings 785a,785b,1190a,1190b are disposed at the first end 830 and the second end 835.

At least a portion of the one or more openings 785a,785b, 1190a,1190b may further comprise a counterbore and/or each of the one or more openings 785a,785b,1190a, 1190b may further comprise a counterbore. The counterbore is concentrically aligned with the at least one opening and/or one or more openings 785a,785b,1190a,1190b. The at least one counterbore and/or one or more counterbores comprises a larger diameter than a diameter of the one or more openings 785a,785b,1190a,1190b. The at least one counterbore and/or one or more counterbores is sized and configured to receive one or more quick release mechanisms and/or the head of the one or more fasteners 620,1170. The at least one counterbore and/or the one or more counterbores extend from a second surface 810,1275 towards a portion of the first surface 805,1270.

At least one of the first 805,1270 and/or second surfaces 810,1275 of distal frame 655,1175 and/or the distal arm or stem 795,1255 may comprise surface finish. At least a portion of the first 805,1270 and/or at least a portion of the second surfaces 810,1275 of distal frame 655,1175 and/or the distal arm or stem 795,1255 may comprise surface finish. The surface finish may comprise protrusions, a roughened surface finish or a polished surface finish. The protrusions may comprise threads, flutes, grooves, and/or teeth that may include various shapes. The various shapes may include tapered, stepped, conical and/or paralleled, flat, pointed, and/or rounded. The surface finishes may further comprise roughened surfaces or porous surfaces, including turned, blasting, sand blasting, acid etching, chemical etching, dual acid etched, plasma sprayed, anodized surfaces, and/or any combination thereof. The surface finishes may further include a polish surface finish. In one embodiment, at least a portion of the second surfaces 810,1275 of distal frame 655,1175 and/or the distal arm or stem 795,1255 comprise protrusions, the protrusions include a plurality of teeth, the plurality of teeth are disposed along a longitudinal axis of the distal frame 655,1175 and/or the distal arm or stem 795,1255. The plurality of teeth is positioned transverse, perpendicular to and/or substantially perpendicular to the longitudinal axis of the distal frame 655,1175 and/or the distal arm or stem 795,1255.

In another embodiment, the distal frame 655,1175 and/or the distal arm or stem 795,1255 comprises a shape and a distal frame length 788,1280. The shape may be uniform or non-uniform. Accordingly, at least a portion of the shape may be uniform or non-uniform. The shape may include a rectangle, an elongated rectangle and/or a rounded, rectangle and/or hemispherical. The shape at the first end 830,1305 and a second end 835,1310 may include a taper. The shape at the first end 830,1305 and a second end 835,1310 may include a substantially rectangular shape and tapered at the opposing end. Accordingly, the first surface 805,1270 and a second surface 810,1275 of the distal frame 655,1175 and/or the distal arm or stem 795,1255 further comprises a curved, arched or hemispherical shape. The proximal frame length 735,1250 is longer or larger than the distal frame length 788,1280. The distal frame 655,1175 and/or the distal arm or stem 795,1255 may be solid or hollow.

In another embodiment, the distal frame 655,1175 and/or the distal arm or stem 795,1255 comprises a ball component 665,1180. The ball component 665,1180 disposed at a first end 830 and/or a second end 835. In one embodiment, the ball component 665,1180 is disposed at a first end 830 of the distal arm 830. The ball component 665,1180 extends outwardly from the first end 830,1305 of the distal arm and/or distal frame. The ball component 665,1180 comprises a ball outer surface 820,1185. The ball component 665,1180 may further comprise, and an inner surface 825. At least a portion of the outer surface 820,1185 of the ball component 665, 1180 contacts and engages with the inner surface 653,1265 of the socket component 645,1215 and/or inner surface 755 of the locking collar 650,1205. The ball component 665, 1180 and/or an outer surface 820,1185 of the ball component 665,1180 comprises a shape, the shape includes a sphere, a hemisphere, arch, domed or convex and/or substantially spherical, hemispherical, arched, domed and/or convex. The ball component 665,1180 may be solid or hollow.

In another embodiment, the ball component 665,1180 further comprises a bridge member, arch member or a handle member 790. The arch or bridge member 790 comprises an arch or convex shape. The arch or bridge member 790 may be integrated with the ball component 665,1180. The arch or bridge member 790 comprises an outer surface 815 and an inner surface 825. At least a portion of the outer surface 815 of the arch or bridge member 790 contacts or engages with a portion of the socket component 645,1215 and/or inner surface 755 of the locking collar 650,1205. At least a portion of the arch or bridge member 790 comprises one or more angled or radiused surfaces 685,690. The one or more angled or radiused surfaces 685,690 may comprise a morse taper angle and/or a morse radius. The morse taper angle comprises an angle of at least 5 degrees or greater. Alternatively, at least a portion of the arch or bridge member 790 of the ball component comprises a first angle or radius 685 and a second angle or radius 690. The first angle or radius 685 is different than the second angle or radius 690. In another embodiment, the first angle or radius may be different than the second angle or radius. The first angle or radius may be larger than the second angle or radius.

In another embodiment, each of the proximal frame 60,640,1210, the proximal arm or stem 150,648,1245, the proximal bracket 65, the socket component 70,645,1215, the distal frame 45,655,1175, the distal bracket 95,660,1165, the distal arm or stem 215,795,1255, the ball component 105, 665,1180, the fixation screws 35,595,1075, the fasteners 75,620,1170, and/or the locking fasteners 80a,80b, 625,1230 comprises a material. The material may include metal, polymers or ceramic. The metals may comprise titanium, titanium alloys, cobalt-chrome alloys, platinum, stainless steel and/or any combination thereof. More specifically, the metal includes titanium and/or cobalt-chrome molybdenum (CoCrMo). The polymers may include thermoplastic or thermoset polymers. The polymers may further include composite thermoplastic or thermoset polymers and/or fiber reinforced composite thermoplastics or thermoset polymers. The polymers may further include carbon fiber, polyether ether ketone (PEEK), polyethylene (PE), ultra-high molecular weight polyethylene (UHMWPE), polycarbonate (PC), polypropylene (PP), polyurethanes (PU), nylon, Teflon, polyolefins and/or any combination thereof. The ceramics may include alumina ceramics, Zirconia (ZrO2) ceramics, Calcium phosphate or hydroxyapatite (Ca10(PO46(OH)2) ceramics, titanium dioxide (TiO2), silica (SiO2), Zinc Oxide (ZnO) and/or any combination thereof. Each of the materials of the proximal frame 60,640,1210, the proximal arm or stem 150,648,1245, the proximal bracket 65, the socket component 70,645,1215, the distal frame 45,655,1175, the distal bracket 95,660,1165, the distal arm or stem 215,795, 1255, the ball component 105,665,1180, the fixation screws 35,595,1075, the fasteners 75,620,1170, and/or the locking fasteners 80a,80b, 625,1230 may be the same or they may be different.

Alternatively, the materials of at least two of the proximal frame 60,640,1210, the proximal arm or stem 150,648,1245, the proximal bracket 65, the socket component 70,645,1215, the distal frame 45,655,1175, the distal bracket 95,660,1165, the distal arm or stem 215,795,1255, the ball component 105,665,1180, the fixation screws 35,595,1075, the fasteners 75,620,1170, and/or the locking fasteners 80a,80b, 625,1230 may be the same or different. In one embodiment, at least one or more of the fixation screws 35,595,1075 and/or the fasteners 75,620,1170, and/or the locking fasteners 80a,80b, 625,1230 comprise a polymer material, the polymer material may comprise Nylon or Teflon.

Accordingly, each of the materials may comprise radiopaque material and/or radiopaque compound. Alternatively, each of the materials may further comprise a translucent material and/or radiolucent material. Each of the materials may further comprise a radiolucent fiber reinforced composite polymer material and/or a radiolucent composite polymer material. Each of the materials may further comprise a radiolucent fiber reinforced composite polymer material and/or a radiolucent composite polymer material. The radiopacity may include radiopaque fillers or compounds, including barium sulfate, zirconium dioxide, titanium dioxide, tungsten, gold, bismuth salts, tantalum and/or any combination thereof. In one embodiment, the material may comprise a radiopaque polymer. In another embodiment, the material may comprise a polymer with a radiopaque filler.

Method of Using the External Fixation System

In one embodiment, the external fixation system 5 comprises the steps of: inserting one or more proximal fixation screws 35 using the guide tool 25 in a first bone position; inserting one or more distal fixation screws 35 in a second bone position; applying the fixation assembly 30 over the proximal and distal fixation screws 35 by having the proximal 65 and distal 95 compression bracket loosely secured to the proximal frame 60 and/or the distal frame 90; securing the fixation assembly 30 over the proximal and distal fixation screws 35 using the driving tool 20; compressing one or more of the fasteners 75 disposed on the proximal frame assembly 55 and/or the distal frame assembly 45 against the quick release mechanisms 85 to release one or more of the proximal and/or distal fixation screws 35; distracting and/or reducing the fracture using controlled, measurable distraction; uncompressing the one or more fasteners 75 and the quick release mechanisms 85 to re-secure the distal frame assembly 45 and the proximal frame assembly 55 against the one or more proximal or distal fixation screws 35 to lock in or fix the distracted bone; performing secondary adjustments of one or more of flexion/extension, supination/pronation, radial/ulnar deviation by loosening the polyaxial ball joint 50.

In another embodiment, the external fixation system 5 comprises the steps of: completing a provisional reduction using longitudinal fraction; marking at one or more positions on a first bone to insert one or more proximal fixation screws 35; performing an incision at the one or more positions on the first bone to spread soft tissue; applying guide tool 25 at the one or more positions and insert the drill wire 40 or drill pin into the guide tool 25; aligning the drill wire 40 or the drill pin at a first laser line with the edge of the guide tool 25 (this indicates a 10 mm length drill pin or drill wire 40 bone insertion at the first bone—the second laser line indicates a 15 mm length drill pin or drill wire 40 to create one or more bone openings on the first bone; applying the one or more proximal fixation screws 35 to the one or more positions on the first bone using the driving tool 20; marking at one or more positions on a second bone to insert one or more distal fixation screws 35; performing an incision at the one or more positions on the second bone to spread soft tissue; applying guide tool 25 at the one or more positions and insert the drill wire 40 or drill pin into the guide tool 25 on the second bone; aligning the drill wire 40 or the drill pin at a first laser line with the edge of the guide tool 25 (this indicates a 10 mm length drill pin or drill wire 40 bone insertion at the first bone—the second laser line indicates a 15 mm length drill pin or drill wire 40 to create one or more bone openings on the second bone; applying the one or more distal fixation screws 35 to the one or more positions on the second bone using the driving tool 20; applying the external fixator assembly 30 over the proximal and distal fixation screws 35 on the first and second bone; compressing one or more of the fasteners 75 disposed on the proximal frame assembly 55 and/or the distal frame assembly 45 against the quick release mechanisms 85 to release one or more of the proximal and/or distal fixation screws 35; distracting and/or reducing the fracture using controlled, measurable distraction or reduction; uncompressing the one or more fasteners 75 and the quick release mechanisms 85 to re-secure the distal frame assembly 45 and the proximal frame assembly 55 against the one or more proximal or distal fixation screws 35 to lock in or fix the distracted bone; performing secondary adjustments of one or more of flexion/extension, supination/pronation, radial/ulnar deviation by loosening the polyaxial ball joint 50; securing the secondary adjustments by tightening or securing the polyaxial ball joint 50.

In another embodiment, the external fixation system 5 comprises the steps of: completing a provisional reduction using longitudinal fraction; marking at one or more positions on a first bone to insert one or more proximal fixation screws 35; performing an incision at the one or more positions on the first bone to spread soft tissue; applying guide tool 25 at the one or more positions and insert the drill wire 40 or drill pin into the guide tool 25; aligning the drill wire 40 or the drill pin at a first laser line with the edge of the guide tool 25 (this indicates a 10 mm length drill pin or drill wire 40 bone insertion at the first bone—the second laser line indicates a 15 mm length drill pin or drill wire 40 to create one or more bone openings on the first bone; applying the one or more proximal fixation screws 35 to the one or more positions on the first bone using the driving tool 20; marking at one or more positions on a second bone to insert one or more distal fixation screws 35; performing an incision at the one or more positions on the second bone to spread soft tissue; applying guide tool 25 at the one or more positions and insert the drill wire 40 or drill pin into the guide tool 25 on the second bone; aligning the drill wire 40 or the drill pin at a first laser line with the edge of the guide tool 25 (this indicates a 10 mm length drill pin or drill wire 40 bone insertion at the first bone—the second laser line indicates a 15 mm length drill pin or drill wire 40 to create one or more bone openings on the second bone; applying the one or more distal fixation screws 35 to the one or more positions on the second bone using the driving tool 20; suturing the skin at the one or more positions on the first bone and the second bone; applying the external fixator assembly 30 over the proximal and distal fixation screws 35 on the first and second bone; compressing one or more of the fasteners 75 disposed on the proximal frame assembly 55 and/or the distal frame assembly 45 against the quick release mechanisms 85 to release one or more of the proximal and/or distal fixation screws 35; distracting and/or reducing the fracture using controlled, measurable distraction or reduction; uncompressing the one or more fasteners 75 and the quick release mechanisms 85 to re-secure the distal frame assembly 45 and the proximal frame assembly 55 against the one or more proximal or distal fixation screws 35 to lock in or fix the distracted bone; performing secondary adjustments of one or more of flexion/extension, supination/pronation, radial/ulnar deviation by loosening the polyaxial ball joint 50; securing the secondary adjustments by tightening or securing the polyaxial ball join 50.

The method of the external fixation system 5 further comprises the steps of: conducting final fluoroscopic images to determine proper fracture reduction and alignment; removing the external fixation assembly 30 and proximal and/or distal fixation screws 35 when the fracture is sufficiently healed using the driving tool 20. In another embodiment, the method of the external fixation system 5 further comprises the steps of: conducting final fluoroscopic images to determine proper fracture reduction and alignment; conducting tertiary adjustments in reduction/distraction, flexion/extension, supination/pronation, radial/ulnar deviation, and/or any combination thereof; removing the external fixation assembly 30 and proximal and/or distal fixation screws 35 when the fracture is sufficiently healed using the driving tool 20.

In another embodiment, the external fixation system comprises the steps of: securing one or more proximal fixation screws to a first bone position using the proximal frame assembly; inserting one or more distal fixation screws in a second bone position; applying the distal frame assembly over the one or more distal fixation screws by having the distal compression bracket loosely secured to the distal frame; distracting and/or reducing the fracture using controlled, measurable distraction; securing the distal frame assembly to the one or more distal fixation screws using the driving tool and tightening the distal compression bracket to the distal frame; performing secondary adjustments of one or more of flexion/extension, supination/pronation, radial/ulnar deviation by loosening the polyaxial ball joint; securing or locking the polyaxial ball joint to prevent or eliminate any movement. The step of applying the distal frame assembly over the one or more distal fixation screws by having the distal compression bracket loosely secured to the distal frame comprises aligning a portion of the distal frame assembly, the distal bracket and/or the distal frame over the metacarpals. Alternatively, aligning an edge or perimeter adjacent to the first end of the distal frame assembly, the distal bracket and/or the distal frame to be proximate or near the metacarpals to carpal bone joint.

Exemplary Embodiments

Embodiment 1. An external fixator system comprising: a distal frame assembly, the distal frame assembly includes a distal frame and a distal compression bracket, the distal compression bracket being spaced apart and secured to the distal frame to create a distal elongated opening; a proximal frame assembly, the proximal frame assembly includes a proximal frame and a proximal compression bracket, the proximate compression bracket being spaced apart and secured to the proximal frame to create a proximal elongated opening; a lockable, multi-axial or polyaxial joint between the distal frame assembly and the proximal frame assembly; and a first fixation screw and a second fixation screw, each of the first and second fixation screws being sized and configured to be disposed within the elongated distal opening and elongated proximal opening, each of the first and second pins engaging a portion of bone on opposing sides of the fracture site; the at least a portion of the distal compression bracket being movable relative to the distal frame to compress the first fixation screw between the distal compression bracket and the distal frame into a fixed or locked position, and the at least a portion of the proximal compression bracket being movable relative to the proximal distal frame to compress the second fixation screw between the proximal compression bracket and the proximal frame into a fixed or locked position.

Embodiment 2. An external fixator system comprising: a distal frame assembly, the distal frame assembly includes a distal frame and a distal compression bracket, the distal compression bracket being spaced apart and secured to the distal frame to create a distal elongated opening; a proximal frame assembly, the proximal frame assembly includes a proximal frame and a proximal compression bracket, the proximate compression bracket being spaced apart and secured to the proximal frame to create a proximal elongated opening; a lockable, multi-axial or polyaxial joint between the distal frame assembly and the proximal frame assembly; and a first fixation screw and a second fixation screw, each of the first and second fixation screws being sized and configured to be disposed within the elongated distal opening and elongated proximal opening, each of the first and second pins engaging a portion of bone on opposing sides of the fracture site; the at least a portion of the distal compression bracket having a first movement relative to the distal frame to uncompress the first fixation screw between the distal compression bracket and the distal frame into a unlocked position, and the at least a portion of the proximal compression bracket having a second movement relative to the proximal distal frame to uncompress the second fixation screw between the proximal compression bracket and the proximal frame into a unlocked position.

Embodiment 3. An external fixator system comprising: a distal frame assembly, the distal frame assembly includes a distal frame and a distal compression bracket, the distal compression bracket being spaced apart and secured to the distal frame to create a distal elongated opening; a proximal frame assembly, the proximal frame assembly includes a proximal frame and a proximal compression bracket, the proximate compression bracket being spaced apart and secured to the proximal frame to create a proximal elongated opening; a lockable, multi-axial or polyaxial joint between the distal frame assembly and the proximal frame assembly; a first fixation screw, the first fixation screw being sized and configured to be disposed within the elongated distal opening, a portion of the distal compression bracket being secured to a portion of the distal frame to compress the first fixation screw between the distal frame and the distal compression bracket and fix the first fixation screw to a first location; and a second fixation screw, the second fixation screw being sized and configured to be disposed within the elongated proximal opening, a portion of the proximal compression bracket being secured to a portion of the proximal frame to compress the second fixation screw between the proximal compression bracket and the proximal frame and fix the second fixation screw to a second location; the at least a portion of the distal compression bracket having a first movement relative to the distal frame from an unlocked position to a locked position, the unlocked position allows the distal compression bracket to release the first fixation screw from compression, and the locked position re-compresses the fixation screw between the distal compression bracket and the distal frame, the at least a portion of the proximal compression bracket having a second movement relative to the proximal frame from an unlocked position to a locked position, the unlocked position allows the proximal compression bracket to release the second fixation screw from compression, and the locked position re-compresses the fixation screw between the proximal compression bracket and the distal frame.

Embodiment 4. An external fixator system comprising: a distal frame assembly, the distal frame assembly includes a distal frame and a distal compression bracket, the distal compression bracket being spaced apart and secured to the distal frame to create a distal elongated opening; a proximal frame assembly, the proximal frame assembly includes a proximal frame and a proximal compression bracket, the proximate compression bracket being spaced apart and secured to the proximal frame to create a proximal elongated opening; a lockable, multi-axial or polyaxial joint between the distal frame assembly and the proximal frame assembly, the polyaxial joint comprises a ball component and a socket component, the ball component is disposed within the socket component to allow poly axial motion, the ball component is movable between an unlocked position and a locked position which the ball component expands within the socket component to restrict polyaxial movement/motion; and a first fixation screw and a second fixation screw, each of the first and second fixation screws being sized and configured to be disposed within the elongated distal opening and elongated proximal opening, each of the first and second pins engaging a portion of bone on opposing sides of the fracture site; the at least a portion of the distal compression bracket being movable relative to the distal frame to compress the first fixation screw between the distal compression bracket and the distal frame into a fixed or locked position, and the at least a portion of the proximal compression bracket being movable relative to the proximal distal frame to compress the second fixation screw between the proximal compression bracket and the proximal frame into a fixed or locked position.

Embodiment 5. An external fixator system comprising: a first or distal frame assembly, the distal frame assembly comprises a distal frame, a ball component and first or distal bracket, the ball component is disposed at one end of the distal frame, the first or distal bracket being spaced apart and secured to a portion of the distal frame that creates an elongated distal opening; a second or proximal frame assembly, the proximal frame assembly comprises a proximal frame, a socket component and second or proximal bracket, the socket component disposed at one end of the proximal frame, the second or proximal bracket being spaced apart and secured to a portion of the proximal frame to create an elongated proximal opening; the ball component of the distal frame assembly is disposed within the socket component of the proximal frame assembly to allow multi-axial or polyaxial translational motion of the distal frame assembly relative to the proximal frame assembly; and a plurality of fixation screws, each of the plurality of fixation screws being sized and configured to be disposed within the elongated distal opening and elongated proximal opening, the plurality of fixation screws engaging a portion of bone on opposing sides of the fracture site.

Embodiment 6. An external fixator system comprising: a first or distal frame assembly, the distal frame assembly comprises a distal frame, a ball component and first or distal bracket, the ball component is disposed at one end of the distal frame, the first or distal bracket being spaced apart and secured to a portion of the distal frame that creates an elongated distal opening; a second or proximal frame assembly, the proximal frame assembly comprises a proximal frame, a socket component and second or proximal bracket, the socket component disposed at one end of the proximal frame, the second or proximal bracket being spaced apart and secured to a portion of the proximal frame to create an elongated proximal opening; the ball component of the distal frame assembly is disposed within the socket component of the proximal frame assembly to create a multi-axial or polyaxial joint that is movable from a first position that is unlocked to allow polyaxial motion of the distal frame assembly relative to the proximal frame assembly, to a second position that is a locked position which restricts the polyaxial motion of the proximal frame assembly relative to the distal frame assembly; and a plurality of fixation screws, the plurality of fixation screws being sized and configured to be disposed within the elongated distal opening and elongated proximal opening, the plurality of fixation screws engaging a portion of bone on opposing sides of the fracture site.

Embodiment 7. An external fixator system comprising: a first or distal frame assembly, the distal frame assembly comprises a distal frame, a ball component and first or distal bracket, the ball component is disposed at one end of the distal frame, the first or distal bracket being spaced apart and secured to a portion of the distal frame that creates an elongated distal opening; a second or proximal frame assembly, the proximal frame assembly comprises a proximal frame, a socket component and second or proximal bracket, the socket component disposed at one end of the proximal frame, at least a portion of the socket component includes a notch that is positioned to be substantially aligned with the through-hole, the second or proximal bracket being spaced apart and secured to a portion of the proximal frame to create an elongated proximal opening; the ball component of the distal frame assembly is disposed within the socket component of the proximal frame assembly to create a multi-axial or polyaxial joint that is movable from a first position that is unlocked to allow polyaxial motion of the distal frame assembly relative to the proximal frame assembly, to a second position that is a locked position which restricts the polyaxial motion of the proximal frame assembly relative to the distal frame assembly; and a first fixation screw and a second fixation screw, each of the first and second fixation screws being sized and configured to be disposed within the elongated distal opening and elongated proximal opening, each of the first and second pins engaging a portion of bone on opposing sides of the fracture site; the at least a portion of the distal bracket being movable relative to the distal frame to compress the first fixation screw between the distal bracket and the distal frame into a fixed or locked position, and the at least a portion of the proximal bracket being movable relative to the proximal distal frame to compress the second fixation screw between the proximal bracket and the proximal frame into a fixed or locked position.

Embodiment 8. An external fixator system comprising: a first or distal frame assembly, the distal frame assembly comprises a distal frame, a ball component and first or distal bracket, the ball component is disposed at one end of the distal frame, the first or distal bracket being secured to a portion of the frame to leave an elongated distal opening, the distal bracket slidably moves relative to the distal frame; a second or proximal frame assembly, the proximal frame assembly comprises a proximal frame, a socket component and second or proximal bracket, the socket component disposed at one end of the proximal frame, the second or proximal bracket being secured to a portion of the proximal frame to leave an elongated proximal opening, the second or proximal bracket slidably moves relative to the proximal frame; the ball component of the distal frame assembly is disposed within the socket component of the proximal frame assembly to create a multi-axial or polyaxial joint that is movable from a first position that is unlocked to allow polyaxial motion of the distal frame assembly relative to the proximal frame assembly, to a second position that is a locked position which restricts the polyaxial motion of the proximal frame assembly relative to the distal frame assembly; a first fixation screw, the first fixation screw being sized and configured to be disposed within the elongated distal opening, a portion of the distal compression bracket being coupled to a portion of the distal frame to compress the first fixation screw between the distal frame and the distal compression bracket and fix the first fixation screw to a first location; and a second fixation screw, the second fixation screw being sized and configured to be disposed within the elongated proximal opening, a portion of the proximal bracket being coupled to a portion of the proximal frame to compress the second fixation screw between the proximal bracket and the proximal frame and fix the second fixation screw to a second location; the at least a portion of the distal bracket including a first quick release movement relative to the distal frame from an unlocked position to a locked position, the unlocked position allows the distal bracket to release the first fixation screw from compression, and the locked position re-compresses the fixation screw between the distal compression bracket and the distal frame, the at least a portion of the proximal bracket including a second quick release movement relative to the proximal frame from an unlocked position to a locked position, the unlocked position allows the proximal bracket to release the second fixation screw from compression, and the locked position re-compresses the fixation screw between the proximal bracket and the proximal frame.

Embodiment 9. The external fixator system of Embodiment 1, 2, 3, or 8 wherein the first and second locations are different.

Embodiment 10. The external fixator system of Embodiment 1, 2, 3 or 8, wherein the first location comprises at least a portion of a metacarpal and the second location comprises a portion of the radius.

Embodiment 11. The external fixator system of Embodiment 1, 2, 3, 4, 5, 6, 7 or 8, wherein the proximal frame assembly and the distal frame assembly comprises a material, the material includes a polymer or metal.

Embodiment 12. The external fixator system of Embodiment 11, wherein the polymer comprises a radiopaque polymer.

Embodiment 13. The external fixator system of Embodiment 12, wherein the radiopaque polymer comprises a radiopaque compound.

Embodiment 14. The external fixator system of Embodiment 13, wherein the radiopaque compound comprises barium sulfate, bismuth trioxide, tungsten, titanium dioxide, and/or any combination thereof.

Embodiment 15. The external fixator system of Embodiment 1, 2 or 3, wherein the polyaxial joint comprises a ball component and a socket component, the ball component is disposed within the socket component to allow polyaxial motion.

Embodiment 16. The external fixator system of Embodiment 15, wherein the ball component is movable from a first position which the ball component is not expanded and allows polyaxial motion relative to the socket component, to a second position which the ball component is expanded within the socket component to create friction that restricts or prevents polyaxial motion relative to the socket component.

Embodiment 17. The external fixator system of Embodiment 1, 2, 3 or 8 wherein the first movement (or first quick release movement) and the second movement (second quick release movement) occur independent of each other (or do not occur at the same time).

Embodiment 18. The external fixator system of Embodiment 1, 2, 3, 4, 5, 6, 7, or 8, wherein the external fixator system is disposable.

Embodiment 19. The external fixator system of Embodiment 1, 2, 3, 4, 5, 6, 7, or 8, wherein the external fixator system is disposable and sterilizable.

Embodiment 20. The external fixator system of Embodiment 1, 2, 3, 4, 5, 6, 7, or 8, wherein the external fixator system further comprises a drill guide.

Embodiment 21. The external fixator system of Embodiment 1, 2, 3, 4, 5, 6, 7, or 8, wherein the external fixator system further comprises a drill guide and a driver tool.

Embodiment 22. The external fixator system of Embodiment 1, 2, 3, 4, 5, 6, 7, or 8, wherein the external fixator system further comprises a drill guide, a drill wire, and a driver tool.

Embodiment 23. The external fixator system of Embodiments 1, 2, 3, 4, 5, 6, 7 or 8, wherein the fixation screw comprises a first marker and a second marker.

Embodiment 24. The external fixator system of Embodiment 23, wherein the first marker is at least at a 10 mm depth marker and the second marker is at least at a 15 mm depth marker.

Embodiment 25. The external fixator system of Embodiment 22, wherein the drill wire comprises a first marker and a second marker.

Embodiment 26. The external fixator system of Embodiment 23, wherein the first and second marker of the drill wire matches the first and second marker of the fixation screw.

Embodiment 27. The external fixator system of Embodiment 11, wherein the polymer comprises a radiolucent polymer or a radiolucent composite polymer.

Embodiment 28. The external fixator system of Embodiment 27, wherein the radiolucent composite polymer is a fiber-reinforced composite polymer.

Embodiment 29. The external fixator system of Embodiment 27, wherein the radiolucent polymer comprises Nylon, PEEK or Carbon Fiber.

Embodiment 30. The external fixator system of Embodiment 28, wherein the fiber-reinforced composite polymer comprises carbon or PEEK.

Embodiment 31. An external fixator system comprising: a distal frame assembly, the distal frame assembly includes a distal frame and a distal compression bracket, the distal compression bracket being spaced apart and secured to the distal frame to create a distal elongated opening, the distal frame comprises a distal frame length; a proximal frame assembly, the proximal frame assembly includes a proximal frame, the proximal frame comprises a proximal frame length, an window and a plurality of bores, the window extends along a portion of the proximal frame length, each of the plurality of bores are spaced apart at a set distance; a lockable, multi-axial or polyaxial joint between the distal frame assembly and the proximal frame assembly, the polyaxial joint comprises a ball component, a socket component and a locking collar, the polyaxial joint is movable from an unlocked position to a locked position, the unlocked position allows the ball component to be movable relative to the socket component to create polyaxial motion and a locked position that rotates the ball component within the socket component to contact or engage a portion of an inner diameter surface of the locking collar to create an interference fit that locks the ball component to the socket component.

Embodiment 32. An external fixator system comprising: a first or distal frame assembly, the distal frame assembly comprises a distal frame, a distal frame length, a ball component and first or distal bracket, the ball component is disposed at one end of the distal frame, the first or distal bracket being spaced apart and secured to a portion of the distal frame that creates an elongated distal opening; a second or proximal frame assembly, the proximal frame assembly comprises a proximal frame and a socket component, the socket component disposed at one end of the proximal frame, the proximal frame comprises a proximal frame length, a window and a plurality of bores, the window extends along a portion of the proximal frame length, each of the plurality of bores are spaced apart at a set distance; the ball component of the distal frame assembly is disposed within the socket component of the proximal frame assembly to create a multi-axial or polyaxial joint that is movable from an unlocked position to a locked position, the unlocked position allows the ball component to be movable relative to the socket component to create polyaxial motion and the locked position that rotates the ball component within the socket component to contact or engage a portion of an inner diameter surface of the locking collar to create an interference fit that locks the ball component to the socket component.

Embodiment 33. The external fixator system of Embodiment 31 or 32, wherein the external fixator system further comprises a plurality of fixation screws.

Embodiment 34. The external fixator system of Embodiment 33, wherein each of the plurality of fixation screws comprises a first marker at a first depth and a second marker at a second depth.

Embodiment 35. The external fixator system of Embodiment 34, wherein the first depth of the first marker is different than the second depth of the second marker.

Embodiment 36. The external fixator system of Embodiment 31 or 32, wherein the external fixator system is disposable.

Embodiment 37. The external fixator system of Embodiment 31 or 32, wherein the external fixator system is disposable and sterilizable.

Embodiment 38. The external fixator system of Embodiment 31 or 32, wherein the external fixator system further comprises a drill guide or guide tool.

Embodiment 39. The external fixator system of Embodiment 31 or 32, wherein the external fixator system further comprises a drill guide and a driver tool.

Embodiment 40. The external fixator system of Embodiment 31 or 32, wherein the external fixator system further comprises a drill guide or guide tool, a drill wire, and a driver tool.

Embodiment 41. The external fixator system of Embodiment 38, 39 or 40, wherein the guide tool further comprises an insert, the insert is disposed into a plurality of bores or openings of the guide tool, the insert includes a plurality of lumens, the plurality of lumens of the insert are smaller than the plurality of bores or openings of the guide tool.

Embodiment 42. The external fixator system of Embodiment 41, wherein the plurality of lumens of the insert is sized and configured to receive at least a portion of the drill wire.

Embodiment 43. The external fixator system of Embodiment 38, 39 or 40, wherein the guide tool further comprises a first orientation structure and a second orientation structure, the first orientation structure extends between at least two of the plurality of bores or openings of a guide body, and the second orientation structure extends along a portion of the longitudinal axis of the handle.

Embodiment 44. The external fixator system of Embodiment 43, wherein the first orientation structure is coaxially aligned with the second orientation structure.

Embodiment 45. The external fixator system of Embodiment 39 or 40, wherein the driver tool comprises a driver handle and a shaft, the shaft includes a first end and a second end, the first end comprises a first drive tip and the second end comprises a second drive tip, the first drive tip is different than the first tool bit tip.

Embodiment 46. The external fixator system of Embodiment 45, wherein the first or second drive tip comprises a male drive tip.

Embodiment 47. The external fixator system of Embodiment 45, wherein the first or second tool bit comprises a female socket drive tip.

Embodiment 48. The external fixator system of Embodiment 47, wherein the female socket drive tip comprises a socket or recess, the socket or recess includes a first end and a second end.

Embodiment 49. The external fixator system of Embodiment 48, wherein the first end of the recess of the female socket drive tip comprises a flared end, Embodiment 50. The external fixator system of Embodiment 48, wherein the first end of the socket of the female socket drive tip comprises a first diameter and the second end of the socket of the female socket drive tip comprises a second diameter, the first diameter of the first end is greater than the second diameter of the second end.

Embodiment 51. The external fixator system of Embodiment 31 or 32, wherein the external fixator proximal frame assembly or the distal frame assembly comprises a radiolucent material or a radiolucent composite material.

Embodiment 52. The external fixator system of Embodiment 51, wherein the radiolucent composite polymer is a fiber-reinforced composite polymer.

Embodiment 53. The external fixator system of Embodiment 51, wherein the radiolucent polymer comprises Nylon, PEEK or Carbon Fiber.

Embodiment 54. The external fixator system of Embodiment 52, wherein the fiber-reinforced composite polymer comprises carbon or PEEK.

Embodiment 55. The external fixator system of Embodiment 31 or 32, wherein the polyaxial motion comprises greater than 90 degrees.

Embodiment 56. The external fixator system of Embodiment 31 or 32, wherein the interference fit comprises a morse taper lock.

Embodiment 57. The external fixator system of Embodiment 31 or 32, wherein the portion of the inner diameter surface of the locking collar comprises a morse taper angle, the morse taper angle includes an angle of greater than 5 degrees.

Embodiment 58. The external fixator system of Embodiment 31 or 32, wherein the portion of the inner diameter surface of the locking collar comprises a morse taper angle, the morse taper angle includes an angle range of 5 degrees to 18 degrees.

Embodiment 59. The external fixator system of Embodiment 31 or 32, wherein the set distance of each of the plurality of bores comprise at least 10 mm.

Embodiment 60. The external fixator system of Embodiment 31 or 32, wherein each of the plurality of bores are a positioned in a plurality of repeating rows.

Embodiment 61. The external fixator system of Embodiment 31 or 32, wherein the proximal frame length is different than the distal frame length.

Embodiment 62. The external fixator system of Embodiment 31 or 32, wherein the proximal frame length is greater than the distal frame length.

We claim:

1. An external fixator system comprising:
a distal frame assembly, the distal frame assembly comprises a distal frame member, a distal compression bracket, the distal compression bracket is movable relative to the distal frame member;

a proximal frame assembly, the proximal frame assembly comprises a proximal frame member, the proximal frame member includes longitudinal axis, a first end, a second end, a first row of openings, a second row of openings, and a window opening, the window opening extending through the proximal frame member, the first row of openings and the second row of openings extending through the proximal frame member, the first row of openings comprises a first plurality of openings, each of the first plurality of openings are spaced apart along the longitudinal axis of the proximal frame, the second row of openings comprises a second plurality of openings, each of the second plurality of openings are spaced apart along the longitudinal axis of the proximal frame member; and a polyaxial joint positioned between the distal frame assembly and the proximal frame assembly, the polyaxial joint comprises a ball component, a socket component and a locking collar, the ball component engages with the socket component to create the polyaxial joint, the polyaxial joint is movable from an unlocked position to a locked position, the unlocked position allows the ball component to be movable relative to the socket component to create polyaxial motion, and the locked position prevents the ball component to be movable relative to the socket component.

2. The external fixator system of claim 1, wherein the external fixator system comprises a disposable external fixator system.

3. The external fixator system of claim 1, wherein the external fixator system comprises a radiolucent material or a radiolucent composite material.

4. The external fixator system of claim 1, wherein the locked position comprises locking the ball component relative to socket component with at least one set screw or the locking collar.

5. The external fixator system of claim 1, wherein at least a portion of the window opening extends into a portion of the socket component.

6. The external fixator system of claim 1, wherein each of the first plurality of openings of the first row of openings comprises a first plurality of opening axis and each of the second plurality of openings of the second row of openings comprises a second plurality of opening axis, at least one of the first plurality of opening axis of the first plurality of openings intersects with at least one of the second plurality of opening axis of the second plurality of openings.

7. The external fixator of claim 1, wherein the first row of openings or the second row of openings comprises threads.

8. The external fixator of claim 1, wherein the first row of openings is spaced apart at 90 degrees from the second row of openings.

9. The external fixator of claim 1, wherein the ball component comprises a substantially hemispherical shape.

10. The external fixator of claim 1, wherein ball component is coupled to a portion of the distal frame member of the distal frame assembly, and the socket component is coupled to a portion of the proximal frame member of the proximal frame assembly.

11. The external fixator of claim 1, wherein the distal frame member comprises a distal frame member length and the distal compression bracket comprises a distal compression bracket length, the distal compression bracket length substantially matches the distal frame member length.

12. The external fixator of claim 1, wherein the proximal frame member of the proximal frame assembly comprises a tapered cylinder.

13. A method to reduce distal radius fractures comprises the steps of:

obtaining an external fixation system, the external fixation system comprises a proximal frame assembly, a distal frame assembly, and a polyaxial joint between the proximal frame assembly and the distal frame assembly, one or more proximal fixation screws and one or more distal fixation screws, the proximal frame assembly comprises a proximal frame member, the proximal frame member includes a window opening extending through the proximal frame member, the distal frame assembly comprising a distal frame member and a distal compression bracket;

securing the one or more proximal fixation screws into a first bone position;

securing one or more distal fixation screws into a second bone position;

applying the proximal frame assembly over the secured one or more proximal fixation screws at the first bone position, and the distal frame assembly over the secured one or more distal fixation screws at the second bone position;

performing one or more adjustments of at least one fracture;

securing the one or more distal fixation screws to the distal frame assembly and the one or more proximal fixation screws to the proximal frame assembly; and locking the polyaxial joint of the external fixator assembly at an optimal wrist position.

14. The method to reduce distal radius fractures of claim 13, wherein the step of performing one or more adjustments of the at least one fracture comprises reducing the at least one fracture.

15. The method to reduce distal radius fractures of claim 13, wherein at least a portion of the window opening is disposed over a portion of the radiocarpal joint.

16. The method to reduce distal radius fractures of claim 13, wherein at least a portion of the proximal frame assembly or at least a portion of the distal frame assembly comprises a radiolucent material.

17. The method to reduce the distal radius fractures of claim 13, wherein the method further comprises the step of positioning the external fixator system on top of a portion of a hand.

18. The method to reduce the distal radius fractures of claim 17, wherein the step of positioning comprises the steps of:

Aligning the distal frame assembly over a portion of a second metacarpal;

Aligning the polyaxial joint over a portion of a wrist joint; and

Aligning at least a portion of the window opening of the proximal frame assembly over a portion of a distal radius.

19. The method to reduce the distal radius fractures of claim 18, wherein the step of positioning further comprises the step of: marking a first bone position from the aligned proximal frame assembly and a second bone position from the aligned distal frame assembly.

20. The method to reduce distal radius fractures of claim 18, wherein the step of aligning the polyaxial joint over a portion of the wrist joint comprises positioning the polyaxial joint adjacent to the at least one fracture to prevent obstruction of the at least one fracture.

* * * * *